(12) United States Patent
Kim et al.

(10) Patent No.: US 11,572,341 B2
(45) Date of Patent: *Feb. 7, 2023

(54) BIGUANIDE COMPOUND AND USE THEREOF

(71) Applicant: ImmunoMet Therapeutics Inc., Houston, TX (US)

(72) Inventors: Hong Woo Kim, Daejeon (KR); Jae Kap Jeong, Daejeon (KR); Ji Sun Lee, Daejeon (KR); Hye Jin Heo, Daejeon (KR); Hong Bum Lee, Daejeon (KR); Ji Ae Kook, Daejeon (KR); Sung Wuk Kim, Gyeonggi-do (KR)

(73) Assignee: ImmunoMet Therapeutics Inc., Houston, TX (US)

(*) Notice: Subject to any disclaimer, the term of this patent is extended or adjusted under 35 U.S.C. 154(b) by 100 days.

This patent is subject to a terminal disclaimer.

(21) Appl. No.: 16/820,860

(22) Filed: Mar. 17, 2020

(65) Prior Publication Data

US 2020/0277255 A1  Sep. 3, 2020

Related U.S. Application Data

(63) Continuation of application No. 15/527,621, filed as application No. PCT/KR2015/012561 on Nov. 20, 2015, now Pat. No. 10,626,085.

(30) Foreign Application Priority Data

Nov. 20, 2014  (KR) .................. 10-2014-0162966

(51) Int. Cl.
*C07C 279/26* (2006.01)
*C07D 211/10* (2006.01)
*C07D 211/34* (2006.01)
*A61K 31/155* (2006.01)
*A61P 35/00* (2006.01)

(52) U.S. Cl.
CPC .......... *C07C 279/26* (2013.01); *A61K 31/155* (2013.01); *A61P 35/00* (2018.01); *C07D 211/10* (2013.01); *C07D 211/34* (2013.01)

(58) Field of Classification Search
CPC ................................................ C07C 279/26
See application file for complete search history.

(56) References Cited

U.S. PATENT DOCUMENTS

| | | |
|---|---|---|
| 3,331,499 A | 7/1967 | Jost |
| 3,366,650 A | 1/1968 | Bernstein et al. |
| 3,960,949 A | 6/1976 | Ahrens et al. |
| 8,642,647 B2 | 2/2014 | Kim et al. |
| 8,796,338 B2 | 8/2014 | Baron et al. |
| 9,050,292 B2 | 6/2015 | Baron et al. |
| 9,133,110 B2 | 9/2015 | Kim et al. |
| 9,211,263 B2 | 12/2015 | Baron et al. |
| 9,416,098 B2 | 8/2016 | Kim et al. |
| 10,626,085 B2* | 4/2020 | Kim .................. A61P 35/00 |
| 2006/0089316 A1 | 4/2006 | Brown et al. |
| 2011/0207810 A1 | 8/2011 | Kim et al. |
| 2012/0177730 A1 | 7/2012 | Baron et al. |
| 2012/0283299 A1 | 11/2012 | Kim et al. |
| 2012/0309799 A1 | 12/2012 | Kim et al. |
| 2013/0059916 A1 | 3/2013 | Rocchi et al. |
| 2013/0095140 A1* | 4/2013 | Baron .................. A61K 9/209 424/400 |
| 2013/0177604 A1 | 7/2013 | Baron et al. |
| 2013/0281387 A1 | 10/2013 | Baron et al. |
| 2013/0281394 A1 | 10/2013 | Baron et al. |
| 2013/0303466 A1 | 11/2013 | Brown et al. |
| 2013/0338095 A1 | 12/2013 | Baron et al. |
| 2014/0030332 A1 | 1/2014 | Baron et al. |
| 2014/0341986 A1 | 11/2014 | Baron et al. |
| 2014/0348749 A1 | 11/2014 | Birsoy et al. |
| 2015/0064223 A1 | 3/2015 | Baron et al. |
| 2015/0065578 A1 | 3/2015 | Baron et al. |
| 2015/0158832 A1 | 6/2015 | Pietras et al. |

(Continued)

FOREIGN PATENT DOCUMENTS

| | | |
|---|---|---|
| CN | 1846694 A | 10/2006 |
| DE | 833959 C | 3/1952 |

(Continued)

OTHER PUBLICATIONS

Pinedo et al (2000).*
McMahon et al (2000).*
Rikimaru et al., "Relationship Between Tissue Culture Cytotoxicity and Acute Toxicity in Mice of Biguanide Derivatives," J Antibiot (Tokyo).18(4):196-199 (1965).
Chen et al., "High yielding microwave-assisted synthesis of 2-(arylmethyl)amino-4-arylamino-6-alkyl-1,3,5-triazines," Tetrahedron Letters. 51(24):3174-3176 (2010).
Mayer et al., "An expedient and facile one-step synthesis of a biguanide library by microwave irradiation coupled with simple product filtration. Inhibitors of dihydrofolate reductase," J Comb Chem. 6(5):776-82 (2004).
Roberts et al., "The effects of biguanides on the reactions of thrombin and on the one-stage prothrombin time of standard human plasma," Ann N Y Acad Sci. 148(3):714-23 (1968).

(Continued)

*Primary Examiner* — Paul V Ward
(74) *Attorney, Agent, or Firm* — Clark & Elbing LLP

(57) ABSTRACT

The present invention relates to a guanidine compound and a use thereof, and more specifically, to a guanidine derivative showing excellent effects of inhibiting cancer cell proliferation, cancer metastasis, and cancer recurrence; a preparation method thereof; and a pharmaceutical composition containing the same as an active ingredient. Compared to existing drugs, the guanidine derivative according to the present invention shows excellent effects of inhibiting cancer cell proliferation, cancer metastasis, and cancer recurrence even with small doses, and may thus be effectively used in preventing or treating various cancers such as uterine cancer, breast cancer, stomach cancer, brain cancer, rectal cancer, colorectal cancer, lung cancer, skin cancer, blood cancer, liver cancer, etc., inhibiting cancer cell proliferation and cancer metastasis.

5 Claims, No Drawings

(56) References Cited

U.S. PATENT DOCUMENTS

| | | | |
|---|---|---|---|
| 2015/0196509 A1 | 7/2015 | Baron et al. |
| 2015/0368198 A1 | 12/2015 | Min et al. |
| 2015/0376123 A1 | 12/2015 | Kim et al. |
| 2016/0317478 A1 | 11/2016 | Kim et al. |
| 2018/0093953 A1 | 4/2018 | Kim et al. |
| 2018/0105494 A1 | 4/2018 | Min et al. |

FOREIGN PATENT DOCUMENTS

| | | | |
|---|---|---|---|
| DE | 1023757 B | 2/1958 |
| EP | 0507317 A2 | 10/1992 |
| GB | 587907 A | 5/1947 |
| GB | 607720 A | 9/1948 |
| JP | S445218 Y1 | 2/1969 |
| KR | 20110081093 A | 7/2011 |
| WO | WO-95/20950 A1 | 8/1995 |
| WO | WO-01/91696 A2 | 12/2001 |
| WO | WO-02/074740 A1 | 9/2002 |
| WO | WO-2004/054989 A1 | 7/2004 |
| WO | WO-2009/113092 A2 | 9/2009 |
| WO | WO-2009/148623 A2 | 12/2009 |
| WO | WO-2011/083998 A2 | 7/2011 |
| WO | WO-2011/147528 A1 | 12/2011 |
| WO | WO-2013/022280 A2 | 2/2013 |
| WO | WO-2013/188452 A1 | 12/2013 |
| WO | WO-2014/123364 A1 | 8/2014 |
| WO | WO-2016/175357 A1 | 11/2016 |

OTHER PUBLICATIONS

Singh et al., "Design, synthesis, biological evaluation and toxicity studies of N,N-disubstituted biguanides as quorum sensing inhibitors," Med Chem Res. 24:1974-1987 (2015).
Haroyan et al., "Synthesis of Biguanide Derivatives," Armyanskii Kimicheskii Zhurnal. 24(9):822-827 (1971) (9 pages).
Lugaro et al., "Studies on the antitumoral activity of the biguanides. V," Arch Ital Patol Clin Tumori. 10(3):211-22 (1967).
Database Registry RN 222729-18-2, created May 1999 (1 page). (Database CA [Online]. Columbus, Ohio, US: Chemical Abstracts Service [compiled on Jul. 8, 1989], searched from STN International, Columbus, USA. AN:111:545. Abstract, RN 65968-06-1, 793614-44-5).
Carrington et al., "Synthetic antimalarials, Part XLIX. The structure and synthesis of the dihydrotriazine metabolite of proguanil," J Chem Soc. pp. 1017-1031 (1954).
Extended European Search Report for European Patent Application No. 15860894.3, dated Sep. 13, 2018 (11 pages).
Indian Office Action for Application No. 1904/MUMNP/2012, dated Oct. 14, 2015 (2 pages).
International Preliminary Report on Patentability for International Application No. PCT/KR2015/004423, dated Oct. 31, 2017 (7 pages).
International Preliminary Report on Patentability for International Patent Application No. PCT/KR2015/012561, dated May 23, 2017 (English language translation provided) (32 pages).
International Search Report for International Application No. PCT/KR2015/004423, dated Jan. 13, 2016 (5 pages).
International Search Report for International Patent Application No. PCT/KR2011/000097, dated Sep. 2, 2011.
International Search Report for International Patent Application No. PCT/KR2015/012561, dated Aug. 19, 2016 (English language translation provided) (13 pages).
James et al., The synthesis of some heterocyclic derivatives of biguanide with antibacterial activity, J Med Chem. 11(5):942-5 (1968).
McMahon, G., "VEGF receptor signaling in tumor angiogenesis," Oncologist. 5 Suppl 1:3-10 (2000).
Neelakantan, "Preparation of Some 1,5-Diaryl Biguanides", Dec. 1957, [ Contribution from the Organic Chemistry Department, Indian Institute of Science] pp. 1587-1588.
Neidle, Failure Modes in the Discovery Process. *Cancer Drug Design and Discovery.* Elsevier/Academic Press, pp. 427-431 (2008).
Notice of Preliminary Rejection for Korean Patent Application No. 10-2014-0162966, dated Oct. 27, 2020 (8 pages) (English language translation provided).
Office Action and English Translation for Chinese Patent Application No. 201580070763.6, dated Sep. 25, 2019 (14 pages).
Office Action for Japanese Patent Application No. 2017-545842, dated Aug. 27, 2019 (8 pages).
Partial Supplementary European Search Report for European Patent Application No. 15860894.3, dated Jun. 4, 2018 (14 pages).
Pinedo et al., "Translational research: the role of VEGF in tumor angiogenesis," The Oncologist. 5:1-2 (2000).
Shapiro et al., "Hypoglycemic Agents. III. 1-3 N1-Alkyl-and Aralkylbiguanides", Jul. 20, 1959, [Contribution from the Research Laboratories of the U.S. Vitamin Corporation], vol. 81:3728-3736.
Shapiro et al., "Hypoglycemic Agents. IV. N1,N5-Alkyl- and Aralkylbiguanides," J Am Chem Soc. 81:4635-9 (1959).
Sharma et al., "Piperazino biguanides as cysticidal agents," Indian Journal of Pharmacy 39(5):113-14 (1977) (abstract only, 1 page).
Shaw et al., "The preparation of certain amino-substituted perfluoroalkyl-s-triazines," J Org Chem. 24:1809-1811 (1959).
Written Opinion of the International Searching Authority for International Application No. PCT/KR2015/004423, dated Jan. 13, 2016 (6 pages).
Written Opinion of the International Searching Authority for International Patent Application No. PCT/KR2015/012561, dated Aug. 19, 2016 (English language translation provided) (30 pages).
Office Action for Japanese Patent Application No. 2020-044497, dated Apr. 20, 2021 (8 pages).

\* cited by examiner

BIGUANIDE COMPOUND AND USE THEREOF

TECHNICAL FIELD

The present invention relates to a guanidine compound and a use thereof, and more specifically, to a guanidine derivative showing excellent effects of inhibiting cancer cell proliferation, cancer metastasis, and cancer recurrence; a preparation method thereof; and a pharmaceutical composition containing the same as an active ingredient.

BACKGROUND ART

While normal cells produce ATP via oxidative phosphorylation and rarely produce lactic acid, cancer cells produce ATP via glycolysis and lactic acid fermentation. Accordingly, unlike normal cells, cancer cells require a higher amount of glucose, and glucose is converted by a pro-oncogenic metabolism which prefers glycolysis even in an aerobic environment (Warburg effect). Cancer cells utilize such a metabolic pathway as a major source of energy supply for producing energy sources, and as such, cancer cells create an environment in which survival, proliferation, angiogenesis, and metastasis can occur actively, and progress into a malignant tumor. Therefore, the inhibition of the energy metabolism by cancer cells will increase the likelihood of solving the narrow therapeutic ranges of existing targeted cancer drugs and resistance thereof, and interests have recently been focused on the development of anticancer drugs targeting the metabolic characteristics of these cancer cells (*Nature Review cancer* 2011; 11: 85-95).

The biguanide-based drugs such as phenformin and metformin are known as mitochondrial complex 1 inhibitor, and these drugs are known to inhibit differentiation and survival of cancer cells by increasing the energy stress of the cancer cells via inhibition of their oxidative phosphorylation. However, the efficacies of these drugs are not strong enough and thus it is difficult for them to be developed into anticancer drugs. In the case of phenforrmin, a biguanide-based drug, its use has been fully prohibited since the late 1970s due to the side-effect of severe lactic acidosis. Accordingly, there is a need to develop a biguanide-based material with improved physicochemical properties exhibiting excellent pharmacological actions compared to the existing metformin while not exhibiting any side-effects, as in phenformin.

DISCLOSURE

Technical Problem

The present invention provides a novel guanidine derivative or a pharmaceutically acceptable salt thereof which exhibits excellent effects of inhibiting cancer cell proliferation, cancer metastasis, and cancer recurrence even with small doses compared to existing drugs, and a preparation method thereof.

Additionally, the present invention provides a pharmaceutical composition for preventing or treating cancer containing the above compound or a pharmaceutically acceptable salt thereof as an active ingredient, and specifically, the cancer may be a disease selected from the group consisting of uterine cancer, breast cancer, stomach cancer, brain cancer, rectal cancer, colorectal cancer, lung cancer, skin cancer, blood cancer, and liver cancer.

Technical Solution

An object of the present invention provides a novel guanidine derivative compound or a pharmaceutically acceptable salt thereof selected from the group consisting of Compounds 1) to 165) described below.

Another object of the present invention provides a pharmaceutical composition for preventing or treating cancer containing the above compound or a pharmaceutically acceptable salt thereof as an active ingredient.

Still another object of the present invention provides a use of the above compound or a pharmaceutically acceptable salt thereof in the preparation of a drug for treating cancer.

Still another object of the present invention provides a method for preventing or treating cancer including administering a therapeutically effective amount of the above compound or a pharmaceutically acceptable salt thereof to a subject in need thereof.

Advantageous Effects of the Invention

Compared to existing drugs, the guanidine derivative according to the present invention shows excellent effects of inhibiting cancer cell proliferation, cancer metastasis, and cancer recurrence even with small doses, and may thus be effectively used in treating various cancers such as uterine cancer, breast cancer, stomach cancer, brain cancer, rectal cancer, colorectal cancer, lung cancer, skin cancer, blood cancer, liver cancer, etc., inhibiting cancer cell proliferation and cancer metastasis.

BEST MODE

In an aspect, the present invention provides a novel guanidine derivative compound selected from the group consisting of the following Compounds 1) to 165) and a pharmaceutically acceptable salt thereof:
1) N1,N1-dimethyl-N5-piperidine biguanide,
2) N1-piperidin-N5-piperidine biguanide,
3) N1,N1-dimethyl-N5-methyl-N5-1-(naphthalen-1-yl)methyl biguanide,
4) N1,N1-dimethyl-N5-(benzo[d][1,3]dioxol-5-yl)methyl biguanide,
5) N1-piperidin-N5-pyrrolidine biguanide,
6) N1-isopropyl-N5-1-(pyridin-3-vi)methyl biguanide,
7) N1,N1-dipropyl-N5-propyl-N5-ethyl biguanide,
8) N1,N1-dipropyl-N5-piperidine biguanide,
9) N1-piperidin-N5-(benzo[d][1,3]dioxol-5-yl)methyl biguanide,
10) N1-(4-chloro)phenyl-N5-t-butyl-N5-benzyl biguanide,
11) N1-(3-bromo)phenyl-N5-(3-bromo)phenyl biguanide,
12) N1-piperidin-N5-(2-chloro)benzyl biguanide,
13) N1-piperidin-N5-(4-chloro)phenethyl biguanide,
14) N1-piperidin-N5-(2-chloro)phenethyl biguanide,
15) N1,N1-dipropyl-N5,N5-dicyclohexyl biguanide,
16) N1,N1-dipropyl-N5,N5-dipropyl biguanide,
17) N1-isopropyl-N5-(4-chloro)phenyl biguanide,
18) N1-(4-methyl)piperazin-N5-(4-trifluoromethyl)benzyl biguanide,
19) N1-(4-methyl)piperazin-N5-(4-trifluoromethyl)phenyl biguanide,
20) N1-(4-methyl)piperazin-N5-(3-trifluoromethyl)benzyl biguanide,
21) N1-(4-methyl)piperazin-N5-(3-trifluoromethyl)phenyl biguanide,
22) N1-(4-methyl)piperazin-N5-(3-trifluoromethoxy)phenyl biguanide,
23) N1-(4-ethoxy)piperidin-N5-(4-trifluoromethyl)phenyl biguanide,
24) N1-(4-ethoxy)piperidin-N5-(3-trifluoromethyl)phenyl biguanide, 25) N1-(4-ethoxy)piperidin-N5-(3-trifluoromethoxy)phenyl biguanide,
26) N1-(4-ethoxy)piperidin-N5-(4-trifluoromethoxy)phenyl biguanide,
27) N1-(4-methyl)piperazin-N5-(4-chloro)phenyl biguanide,
28) N1-(4-methyl)piperazin-N5-(3-fluoro)phenyl biguanide,
29) N1-(4-methyl)piperazin-N5-(3-chloro)phenyl biguanide,
30) N1-(4-methyl)piperazin-N5-(2-chloro)phenyl biguanide,
31) N1-(4-methyl)piperazin-N5-(4-chloro)benzyl biguanide,
32) N1-(4-methyl)piperazin-N5-(2-chloro)benzyl biguanide,
33) N1-(4-methyl)piperazin-N5-(4-fluoro)phenyl biguanide,
34) N1-(4-methyl)piperazin-N5-(2-fluoro)phenyl biguanide,
35) N1-(4-methyl)piperazin-N5-(3-chloro)benzyl biguanide,
36) N1-(4-methyl)piperazin-N5-butyl biguanide,
37) N1-(4-methyl)piperazin-N5-(3,4-dichloro)phenyl biguanide,
38) N1-(4-methyl)piperazin-N5-(3,4-difluoro)phenyl biguanide,
39) N1-(4-methyl)piperazin-N5-(3,5-difluoro)phenyl biguanide,
40) N1-(4-methyl)piperazin-N5-(3,4,5-trifluoro)phenyl biguanide,
41) N1-(3-pyridine)-N5-(3-trifluoromethyl)phenyl biguanide,
42) N1-3-pyridin-N5-(3-trifluoromethoxy)benzyl biguanide,
43) N1-3-pyridin-N5-(3-trifluoromethyl)benzyl biguanide,
44) N1-(3-methyl)piperidin-N5-cyclopentyl biguanide,
45) N1-(3-methyl)piperidin-N5-(4-methoxy)piperidine biguanide,
46) N1-(3-methyl)piperidin-N5-(4-ethoxy)piperidine biguanide,
47) N1-(3-methyl)piperidin-N5-pyrazin-2yl biguanide,
48) N1-(4-methyl)piperidin-N5-(4-bromo)phenyl biguanide hydrochloride,
49) N1-(4-methyl)piperidin-N5-(3-trifluoromethoxy)phenyl biguanide,
50) N1-(4-methyl)piperidin-N5-(3-trifluoromethyl)phenyl biguanide,
51) N1-(3-methyl)piperidin-N5-(3-trifluoromethyl)phenyl biguanide,
52) N1-(4-methyl)piperidin-N5-(4-trifluoromethoxy)phenyl biguanide,
53) N1-(4-methyl)piperidin-N5-(4-trifluoromethyl)phenyl biguanide,
54) N1-(4-methyl)piperidin-N5-(3-trifluoromethyl)-4-fluoro)phenyl biguanide,
55) N1-(4-methyl)piperidin-N5-(4-chloro)phenyl biguanide,
56) N1-(4-methyl)piperidin-N5-(4-fluoro)phenyl biguanide,
57) N1-(4-methyl)piperidin-N5-(3-fluoro-4-trifluoromethyl)phenyl biguanide,
58) N1-(4-methyl)piperidin-N5-(3-trifluoromethyl-4-chloro)phenyl biguanide,
59) N1-(4-methyl)piperidin-N5-(3-fluoro-4-trifluoromethyl)phenyl biguanide,
60) N1-(4-methyl)piperidin-N5-(3-trifluoromethoxy)benzyl biguanide,
61) N1-(4-methyl)piperidin-N5-(3-trifluoromethyl)benzyl biguanide,
62) N1-(3,5-dimethyl)piperidin-N5 (4-trifluoromethoxy) phenyl biguanide,
63) N1-(3,5-dimethyl)piperidin-N5-(4-trifluoromethyl)phenyl biguanide,
64) N1-(3,5-dimethyl)piperidin-N5-(4-fluoro)phenyl biguanide,
65) N1-(3,5-dimethyl)piperidin-N5-(3-trifluoromethyl-4-fluoro)phenyl biguanide,
66) N1-2,5-dihydro-1H-pyrrol-N5-pyridin-3-yl biguanide,
67) N1-2,5-dihydro-1H-pyrrol-N5-2,5-dihydro-1H-pyrrole biguanide,
68) N1-1,2,3,6-tetrahydropyridin-N5-1,2,3,6-tetrahydropyridine biguanide,
69) N1-(4-methyl)piperidin-N5-(4-aminoethyl)phenyl biguanide,
70) N1-pyrrolidin-N5-(4-acetyl)phenyl biguanide,
71) N1-piperidin-N5-(4-morpholin-4-yl)phenyl biguanide,
72) N1-pyrrolidin-N5-(4-bromo)phenyl biguanide,
73) N1-piperidin-N5-(4-methoxy)phenyl biguanide,
74) N1-piperidin-N5-(2-propyl)phenyl biguanide,
75) N1-pyrrolidin-N5-(2-trifluoromethyl)phenyl biguanide,
76) N1-pyrrolidin-N5-(2-chloro-5-trifluoromethyl)phenyl biguanide,
77) N1-pyrrolidin-N5-(2-chloro-4-fluoro)phenyl biguanide,
78) N1-pyrrolidin-N5-(2,3-dichloro)phenyl biguanide,
79) N1-pyrrolidin-N5-(4-trifluoromethylthio)phenyl biguanide,
80) N1-pyrrolidin-N5-(2,6-difluoro)phenyl biguanide,
81) (3-(3-(imino(piperidin-1-yl)methyl)guanidino)benzyl) triphenylphosphonium chloride,
82) N1-pyrrolidin-N5-methyl-N5-(4-trifluoromethoxy)phenyl biguanide,
83+) N1-pyrrolidin-N5-(4-phenoxy)phenyl biguanide,
84) N1,N1-dimethyl-N5-(4-trifluoromethoxy)phenyl biguanide,
85) N1,N1-dimethyl-N5-methyl-N5-(4-trifluoromethoxy) phenyl biguanide,
86) N1-2-(benzo[d][1,3]dioxol-5-yl)ethyl-N5-(2-thiophen-2-yl)ethyl biguanide,
87) N1-(N-acetyl)piperazin-N5-(4-trifluoromethoxy)phenyl biguanide,
88) N1-2-(benzo[d][1,3]dioxol-5-yl)ethyl-N5-butyl biguanide,
89) N1-2-(benzo[d][1,3]dioxol-5-yl)ethyl-N5-phenethyl biguanide,
90) N1-(4,4-difluoro)piperidin-N5-(3,4-dichloro)phenyl biguanide,
91) N1-(4,4-difluoro)piperidin-N5-5,6,7,8-tetrahydronaphthalen-2-yl biguanide,
92) N1-butyl-N2-cycloheptyl biguanide,
93) N1,N1-dimethyl-N2-(4-fluoro)benzyl-N5-piperidine biguanide,
94) N1-phenyl-N2-phenethyl biguanide,
95) N1-phenethyl-N2-(4-bromo)phenyl biguanide,
96) N1-benzyl-N2-methyl-N5,N5-dimethyl biguanide,
97) N1-phenethyl-N2-methyl-N5,N5-dimethyl biguanide,
98) N1-(4-chloro)benzyl-N2-cycloheptyl biguanide,
99) N1-piperidin-N2-(2-thiophen-2-yl)ethyl biguanide,
100) N1-(benzo[d][1,3]dioxol-5-yl)methyl-N2-ethyl biguanide,
101) N1-2-(benzo[d][1,3]dioxol-5-yl)ethyl-N2-ethyl biguanide,
102) N1-2-(benzo[d][1,3]dioxol-5-yl)ethyl-N2-methyl biguanide,
103) N1-(2-thiophen-2-yl)ethyl-N2-phenethyl biguanide,
104) N1-(2-thiophen-2-yl)ethyl-N2-2-(benzo[d][1,3]dioxol-5-yl)ethyl biguanide, 105) N1-(4-trifluoromethoxy)phenyl-N2-methyl-N5-pyrrolidine biguanide,
106) N1-methyl-N1-(4-trifluoromethoxy)phenyl-N2-methyl-N5-pyrrolidine biguanide,
107) N1-(benzo[d][1,3]dioxol-5-yl)methyl-N2-cyclopentyl biguanide,
108) N1-methyl biguanide,
109) N1-hexyl biguanide,
110) N1-(4-chloro)phenyl biguanide,
111) N1-(2-propene) biguanide,
112) N1-(benzo[d][1,3]dioxol-5-yl)methyl biguanide,
113) N1-phenyl biguanide,
114) N1-propyl biguanide,
115) N1,N1-diisopropyl biguanide,
116) N1-(4-bromo)phenyl biguanide,
117) N1-(4-acetyl)phenyl biguanide,
118) N1-morpholin-4-yl biguanide,
119) N1-(2-trifluoromethyl)phenyl biguanide,
120) N1-(4-methoxy)phenyl biguanide,
121) N1-(2-propyl)phenyl biguanide,
122) N1-(4-morpholin-4-yl)phenyl biguanide,
123) N1-piperidine biguanide,
124) N1-benzyl biguanide,
125) N1-4-(N-acetylamino)phenyl biguanide,
126) N1-pyrrolidine biguanide,
127) N1-4-(pyridin-2-yl)piperazine biguanide,
128) N1-(4-trifluoromethyl)phenyl biguanide,
129) N1-(4-chloro)benzyl biguanide,
130) N1,N1-dibenzyl biguanide,
131) N1-(4-methoxy)benzyl biguanide,
132) N1-(4-fluoro)benzyl biguanide,
133) N1,N1-dihexyl biguanide,
134) N1-methyl-N1-butyl biguanide,
135) N1-methyl-N1-cyclohexyl biguanide,
136) N1,N1-dicyclohexyl biguanide,
137) N1-(4-chloro)phenethyl biguanide,
138) N1-(4-hydroxy)phenethyl biguanide,
139) N1-azepane biguanide,
140) N1-(4-trifluoromethoxy)phenyl biguanide,
141) N1-(4-trifluoromethyl)benzyl biguanide,
142) N1-(4-trifluoromethoxy)benzyl biguanide,
143) N1-2-(benzo[d][1,3]dioxol-5-yl)ethyl biguanide,
144) N1-(furan-2-yl)methyl biguanide,
145) N1-(2-thiophen-2-yl)ethyl biguanide,
146) N1-(2-fluoro-4-hydroxy)benzyl biguanide,
147) N1-(4-fluoro)phenylpropyl biguanide,
148) N1-(4-methoxy)phenylpropyl biguanide,
149) N1-(2-iodo)benzyl biguanide,
150) N1-(3-iodo)benzyl biguanide,
151) N-(6,6-dimethyl-4-oxo-1,4,5,6-tetrahydropyrimidin-2-yl)piperidin-1-carboximidamide,
152) 1-(6,6-dimethyl-4-oxo-1,4,5,6-tetrahydropyrimidin-3-yl)guanidine,
153) N-(1,4,5,6-tetrahydropyrimidin-2-yl)piperidin-1-carboximidamide,
154) N-(6-methyl-4-oxo-1,4,5,6-tetrahydropyrimidin-2-yl)piperidin-1-carboximidamide,
155) N-(5-methyl-4-oxo-1,4,5,6-tetrahydropyrimidin-2-yl)piperidin-1-carboximidamide,
156) N-(4-oxo-1,4,5,6-tetrahydropyrimidin-2-yl)piperidin-1-carboximidamide,
157) N-(6-cyclopropyl-4-oxo-1,4,5,6-tetrahydropyrimidin-2-yl)piperidin-1-carboximidamide hydrochloride,
158) N-(5-methyl-1,4,5,6-tetrahydropyrimidin-2-yl)piperidin-1-carboximidamide,
159) N-(6-isopropyl-4-oxo-1,4,5,6-tetrahydropyrimidin-2-yl)piperidin-1-carboximidamide,
160) 1-(5-methyl-4-oxo-1,4,5,6-tetrahydropyrimidin-3-yl)guanidine,
161) N-(6-isobutyl-4-oxo-1,4,5,6-tetrahydropyrimidin-2-yl)piperidin-1-carboximidamide,
162) N-(4-methyl-1,4,5,6-tetrahydropyrimidin-2-yl)piperidin-1-carboximidamide,
163) N-(6-propyl-4-oxo-1,4,5,6-tetrahydropyrimidin-2-yl)piperidin-1-carboximidamide,
164) 1-(6-methyl-4-oxo-1,4,5,6-tetrahydropyrimidin-3-yl)guanidine, and
165) N-(4-ethyl-1,4,5,6-tetrahydropyrimidin-2-yl)piperidin-1-carboximidamide;

The N1,N1-dimethyl-N5-piperidine biguanide compound according to the present invention may be prepared by an illustrative method shown in Reaction Scheme 1 below. Furthermore, among the compounds according to the present invention, the compounds with a biguanide structure having substituents at N1 and N5 may be prepared by a method varying only the cyanoguanidine and amine compounds in Reaction Scheme 1 below.

[Reaction Scheme 1]

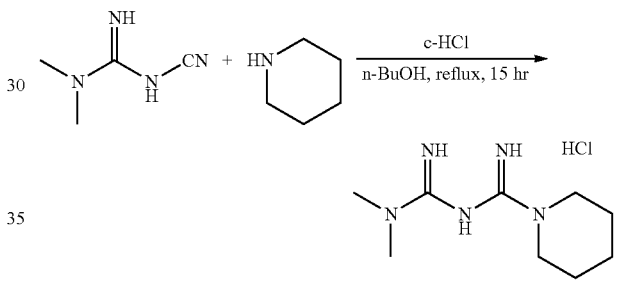

Specifically, piperidine was dissolved in n-butanol and then 1 equivalent of the cyanoguanidine compound and 1 equivalent of concentrated hydrochloric acid were added thereto and the mixture was stirred under reflux for 15 hours. Once the reaction is completed, a compound can be obtained by solvent evaporation under reduced pressure and purification.

The N1-butyl-N2-cycloheptyl biguanide hydrochloride compound according to the present invention may be prepared by an illustrative method shown in Reaction Scheme 2 below. Furthermore, among the compounds according to the present invention, the compounds with a biguanide structure having substituents at N1 and N2 may be prepared by a method varying only the thiourea and guanidine compounds in Reaction Scheme 2 below.

[Reaction Scheme 2]

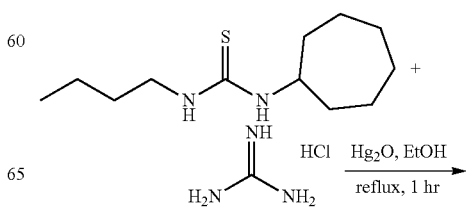

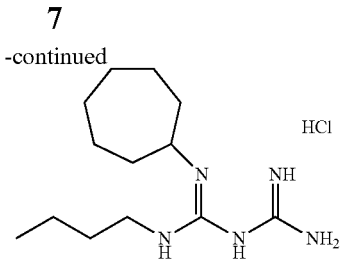

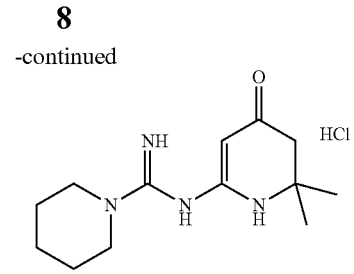

Specifically, the thiourea compound was dissolved in ethanol and then 3 equivalents of guanidine hydrochloride and 2 equivalents of mercury oxide were added thereto and the mixture was stirred under reflux for 1 hour. Once the reaction is completed, a compound can be obtained by filtration, evaporation of the solvent under reduced pressure and purification.

The N1-methyl biguanide hydrochloride compound according to the present invention may be prepared by an illustrative method shown in Reaction Scheme 3 below. Furthermore, among the compounds according to the present invention, the biguanide compounds having a substituent at N1 may be prepared by a method varying only the amine compound in Reaction Scheme 3 below.

[Reaction Scheme 3]

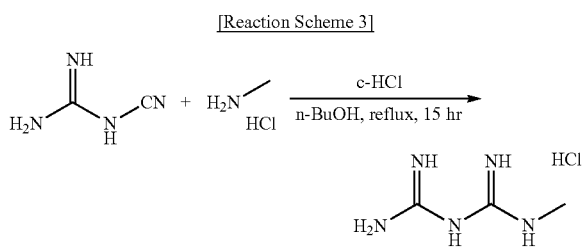

Specifically, the amine compound was dissolved in n-butanol and then 1 equivalent of the cyanoguanidine compound and 1 equivalent of concentrated hydrochloric acid were added thereto and the mixture was stirred under reflux for 15 hours. Once the reaction is completed, a compound can be obtained by solvent evaporation under reduced pressure and purification.

The N-(6,6-dimethyl-4-oxo-1,4,5,6-tetrahydropyrimidin-2-yl)piperidin-1-carboximidamide hydrochloride compound according to the present invention may be prepared by an illustrative method shown in Reaction Scheme 4 below. Furthermore, among the compounds according to the present invention, the guanide compounds having a structure of tetrahydropyrimidine may be prepared by a method varying only the cyanoguanidine and amine compounds in Reaction Scheme 3 below.

[Reaction Scheme 4]

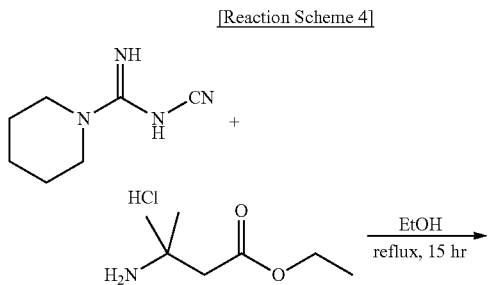

Specifically, the aminobutanoate compound was dissolved in ethanol and then 1 equivalent of the cyanoguanidine compound was added thereto and the mixture was stirred under reflux for 15 hours. Once the reaction is completed, a compound can be obtained by solvent evaporation under reduced pressure and purification.

Meanwhile, the pharmaceutically acceptable salt of the above compounds according to the present invention may be an acid addition salt formed using an organic or inorganic acid. Examples of the organic acid may include formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxyacetic acid, benzenesulfonic acid, 4-toluenesulfonic acid, and methanesulfonic acid. Examples of the inorganic acid may include hydrochloric acid, hydrobromic acid, sulfuric acid, phosphoric acid, nitric acid, carbonic acid, and boric acid. The acid addition salt mentioned above may be prepared by applying to the conventional methods of salt preparation, for example, by a) directly mixing the compound above with an acid, b) mixing any of these by dissolving in a solvent or water-containing solvent, or c) mixing the compound above with an acid in the presence of a solvent or hydrated solvent.

In a specific embodiment, the pharmaceutically acceptable salt of the compound may be a salt with an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid, methanesulfonic acid, dichloroacetic acid, aminooxyacetic acid, hydrochloric acid, hydrobromic acid, sulfuric acid, phosphoric acid, nitric acid, carbonic acid, and boric acid.

Another aspect of the present invention provides a pharmaceutical composition containing the guanidine derivative compound or a pharmaceutically acceptable salt thereof as an active ingredient. The pharmaceutical composition according to the present invention has an excellent effect of inhibiting the proliferation of cancer cells and can thus be used for preventing or treating various cancers. Accordingly, the present invention provides a use of the guanidine derivative compound or a pharmaceutically acceptable salt thereof for preventing or treating cancer, and a method for preventing or treating cancer including administering a therapeutically effective amount of the compound or a pharmaceutically acceptable salt thereof to a subject in need thereof.

In a specific embodiment, the cancer may include uterine cancer, breast cancer, stomach cancer, brain cancer, rectal cancer, colorectal cancer, lung cancer, skin cancer, blood cancer, and liver cancer, but is not limited thereto.

The pharmaceutical composition of the present invention may include at least one pharmaceutically acceptable carrier, in addition to active ingredients. As used herein, the term "pharmaceutically acceptable carrier" refers to a pharmaceutical excipient, which is useful in formulating pharmaceutically active compounds for administration and known as substantially non-toxic and non-sensitive under the conditions of use. The exact ratio of the excipient may be determined not only by the solubility, chemical properties, selected routes of administration of an active compound, but also by the standard pharmaceutical practices.

The pharmaceutical composition of the present invention may be formulated into a form suitable for the desired administration method, using additives such as an appropriate and physiologically acceptable excipient, disintegrant, sweetener, binder, coating agent, swelling agent, lubricant, glidant, flavoring agent, etc.

The pharmaceutical composition may be formulated into tablets, capsules, pills, granules, powders, injections, and liquids, but is not limited thereto.

The formulations of the pharmaceutical composition and pharmaceutically acceptable carriers may be appropriately selected according to the technologies known in the art.

Meanwhile, as used herein, the term "subject" refers to a warm-blooded animal such as a mammal which has a particular disease, disorder, or illness, for example, humans, orangutans, chimpanzees, mice, rats, dogs, cows, chickens, pigs, goats, sheep, etc., but the animal is not limited thereto.

As used herein, the term "treatment" refers to any action to alleviate symptoms, to temporarily or permanently eliminate the cause(s) of symptoms, and to prevent or delay the occurrence of symptoms and the progress of the diseases, disorders, and illnesses described above, but is not limited thereto.

As used herein, the term "effective amount" of an active ingredient of the pharmaceutical composition of the present invention refers to the amount required for achieving the treatment of a given disease. Accordingly, the effective amount may be adjusted according to various factors including the type of a disease, severity of illness, and kinds and amounts of active ingredients and other ingredients contained in a composition, formulation type, age, weight, general health conditions, sex, and diets of a patient, duration and route of administration, release rate of a composition, duration of treatment, and drugs used in combination. For adults, for example, the compound or a pharmaceutically acceptable salts thereof according to the present invention may be administered once or a few times daily, in an amount of a total of 50 mg/kg to 3000 mg/kg. However, the amount for administration may vary according to various factors illustrated above, and may be administered in a lesser amount or a higher amount compared to the above range of the amount for administration depending on the cases.

DETAILED DESCRIPTION OF THE INVENTION

Hereinafter, the present invention will be described in more detail with reference to the following Examples. However, these Examples are for illustrative purposes only and the invention is not intended to be limited by these Examples.

Example 1: Synthesis of N1,N1-dimethyl-N5-piperidine Biguanide Hydrochloride

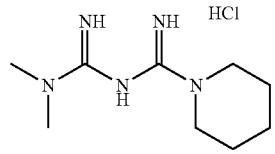

Piperidine (0.85 g, 9.98 mmol) was dissolved in n-butanol (20 mL) at room temperature. N,N-dimethylcyanoguanidine (1.12 g, 9.98 mmol) and concentrated hydrochloric acid (0.9 mL, 9.98 mmol) were added thereto and stirred under reflux for 15 hours. The reaction mixture was concentrated under reduced pressure and separated and purified using a chromatography in a condition where the ratio of methylene chloride (MC) to methyl alcohol (MeOH) was 9:1 and the target compound was obtained as a white solid (1.5 g, 64.0%).

$^1$H NMR (600 MHz, DMSO) δ 2.90 (t, J=6 Hz, 4H), 2.82 (s, 6H), 1.64 (m, 4H), 1.49 (m, 2H)

LCMS: 198.0 [M+H]$^+$

Example 2: Synthesis of N1-piperidin-N5-piperidine Biguanide Hydrochloride

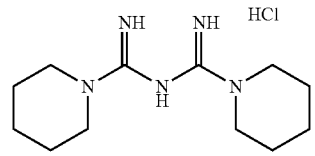

The target compound was obtained as a white solid (1.28 g, 47.0%) in the same manner as in Example 1, except that piperidine cyanoguanidine was used instead of N,N-dimethylcyanoguanidine.

$^1$H NMR (600 MHz, DMSO) δ 2.93 (t, J=6 Hz, 8H), 1.62 (m, 8H), 1.47 (m, 4H)

LCMS: 238.0 [M+H]$^+$

Example 3: Synthesis of N1,N1-dimethyl-N5-methyl-N5-1-(naphthalen-1-yl)methyl Biguanide Hydrochloride

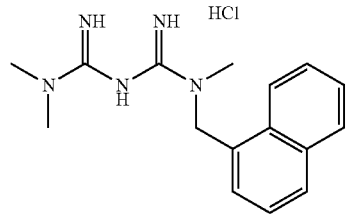 [SMILES: Cl ; CN(C)C(=N)NC(=N)N(C)Cc1cccc2ccccc12]

The target compound was obtained as a white solid (0.62 g, 70.7%) in the same manner as in Example 1, except that N-methyl-1-(naphthalen-1-yl)methanamine was used instead of piperidine.

¹H NMR (600 MHz, DMSO) δ 8.26 (d, J=8.4 Hz), 8.02 (d, J=8.4 Hz, 1H), 7.79 (d, J=8.4 Hz, 1H), 7.57 (m, 4H), 4.61 (s, 2H), 3.05 (s, 9H)
LCMS: 284.0 [M+H]⁺

Example 4: Synthesis of N1,N1-dimethyl-N5-(benzo[d][1,3]dioxol-5-yl)methyl Biguanide Hydrochloride

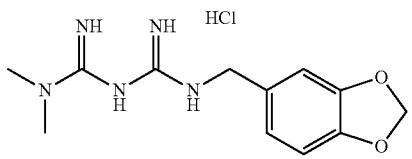 [SMILES: Cl ; CN(C)C(=N)NC(=N)NCc1ccc2c(c1)OCO2]

The target compound was obtained as a white solid (1.8 g, 60.0%) in the same manner as in Example 1, except that benzo[d][1,3]dioxol-5-yl methanamine was used instead of piperidine.
¹H NMR (600 MHz, DMSO) δ 7.06 (s, 1H), 6.90 (s, 2H), 5.99 (s, 2H), 3.87 (s, 2H), 3.32 (s, 6H)
LCMS: 264.0 [M+H]⁺

Example 5: Synthesis of N1-piperidin-N5-pyrrolidine Biguanide Hydrochloride

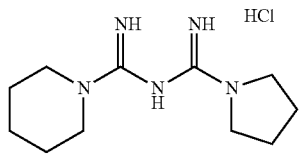 [SMILES: Cl ; N=C(NC(=N)N1CCCC1)N1CCCCC1]

The target compound was obtained as a white solid (0.65 g, 50.0%) in the same manner as in Example 1, except that piperidine cyanoguanidine and pyrrolidine were used instead of N,N-dimethylcyanoguanidine and piperidine.
¹H NMR (600 MHz, DMSO) δ 3.07 (m, 21-H) 2.97 (t, J=6 Hz, 6H), 1.83 (m, 2H), 1.69 (m, 6H), 1.54 (m, 2H)
LCMS: 224.1 [M+H]⁺

Example 6: Synthesis of N1-isopropyl-N5-1-(pyridin-3-yl)methyl Biguanide Hydrochloride

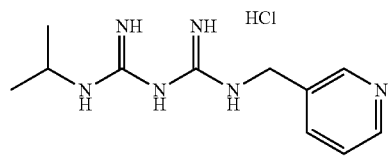 [SMILES: Cl ; CC(C)NC(=N)NC(=N)NCc1cccnc1]

The target compound was obtained as a white solid (0.11 g, 15.0%) in the same manner as in Example 1, except that isopropylcyanoguanidine and 1-(pyridin-3-yl)methanamine were used instead of N,N-dimethylcyanoguanidine and piperidine.
¹H NMR (600 MHz, DMSO) δ 8.52 (s, 1H), 8.46 (m, 1H), 7.72 (n, 1H), 7.37 (m, 1H), 4.37 (s, 2H), 3.65 (m, 1H), 1.04 (s, 6H)
LCMS: 235.1 [M+H]⁺

Example 7: Synthesis of N1,N1-dipropyl-N5-propyl-N5-ethyl Biguanide Hydrochloride

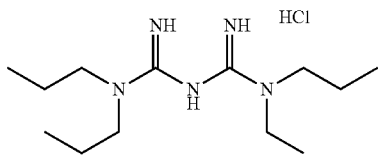 [SMILES: Cl ; CCCN(CC)C(=N)NC(=N)N(CCC)CCC]

The target compound was obtained as a white solid (0.52 g, 30.2%) in the same manner as in Example 1, except that N N-diisopropylcyanoguanidine and N-ethylpropan-1-amine were used instead of N,N-dimethylcyanoguanidine and piperidine.
¹H NMR (600 MHz, DMSO) δ 2.86 (m, 4H), 2.77 (m, 4H), 1.57 (m, 6H), 1.15 (m, 6H), 0.87 (m, 6H)
LCMS: 256.1 [M+H]⁺

Example 8: Synthesis of N1,N1-dipropyl-N5-piperidine Biguanide Hydrochloride

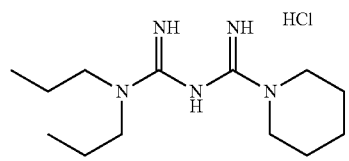 [SMILES: Cl ; CCCN(CCC)C(=N)NC(=N)N1CCCCC1]

The target compound was obtained as a white solid (0.60 g, 31.0%) in the same manner as in Example 1, except that N,N-dipropylcyanoguanidine was used instead of N,N-dimethylcyanoguanidine.
¹H NMR (600 MHz, DMSO) δ 3.22 (m, 8H), 1.53 (m, 8H), 0.91 (m, 8H)
LCMS: 254.1 [M+H]⁺

Example 9: Synthesis of N1-piperidin-N5-(benzo[d][1,3]dioxol-5-yl)methyl Biguanide Hydrochloride

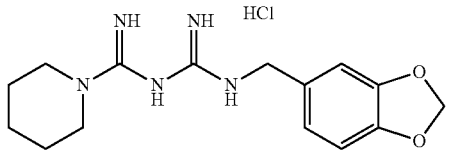 [SMILES: Cl ; N=C(NCc1ccc2c(c1)OCO2)NC(=N)N1CCCCC1]

The target compound was obtained as a white solid (1.00 g, 40.0%) in the same manner as in Example 1, except that piperidine cyanoguanidine and benzo[d][1,3]dioxol-5-yl-methanamine were used instead of N,N-dimethylcyanoguanidine and piperidine.
¹H NMR (600 MHz, DMSO) δ 7.04 (s, 1H), 6.93 (s, 2H), 5.97 (s, 2H), 3.87 (s, 2H), 3.33 (m, 4H), 1.62 (m, 4H), 1.47 (nm, 2H)
LCMS: 304.1 [M+H]⁺

Example 10: Synthesis of N1-(4-chloro)phenyl-N5-t-butyl-N5-benzyl Biguanide Hydrochloride

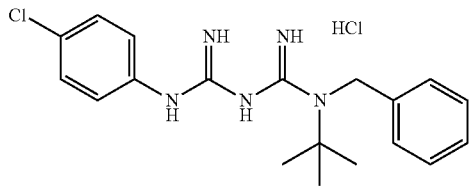 [SMILES: CC(C)(C)N(Cc1ccccc1)C(=N)NC(=N)Nc1ccc(Cl)cc1 ; Cl]

The target compound was obtained as a white solid (0.56 g, 57.0%) in the same manner as in Example 1, except that 4-chlorophenylcyanoguanidine and N-benzyl-2-methylpropan-2-amine were used instead of N,N-dimethylcyanoguanidine and piperidine.

$^1$H NMR (600 MHz, DMSO) δ 7.66 (m, 4H), 7.38 (m, 5H), 4.07 (s, 2H), 1.42 (s, 9H) LCMS: 358.1 [M+H]$^+$

Example 11: Synthesis of N1-(3-bromo)phenyl-N5-3-bromo)phenyl Biguanide Hydrochloride

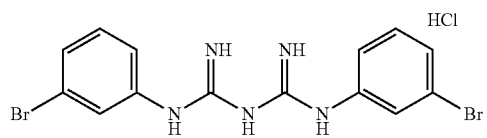 [SMILES: Cl ; N=C(NC(=N)Nc1cccc(Br)c1)Nc1cccc(Br)c1]

The target compound was obtained as a white solid (0.58 g, 26.0%) in the same manner as in Example 1, except that 3-bromophenol cyanoguanidine and 3-bromoaniline were used instead of N,N-dimethylcyanoguanidine and piperidine.

$^1$H NMR (600 MHz, DMSO) δ 7.58 (s, 2H), 7.29 (m, 6H) LCMS: 411.1 [M+H]$^+$

Example 12: Synthesis of N1-piperidin-N5-(2-chloro)benzyl Biguanide Hydrochloride

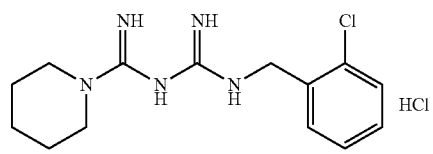 [SMILES: N=C(NCc1ccccc1Cl)NC(=N)N1CCCCC1 ; Cl]

The target compound was obtained as a white solid (0.43 g, 41.3%) in the same manner as in Example 1, except that piperidine cyanoguanidine and 2-chlorobenzylamine were used instead of N,N-dimethlcyanoguanidine and piperidine.

$^1$H NMR (600 MHz, DMSO) δ 7.60 (m, 1H), 7.42 (m, 1H), 7.25 (m, 2H), 4.00 (s, 2H), 2.93 (m, 4H), 1.65 (m, 4H), 1.52 (m, 2H)

LCMS: 294.1 [M+H]$^+$

Example 13: Synthesis of N1-piperidin-N5-4-chloro)phenethyl Biguanide Hydrochloride

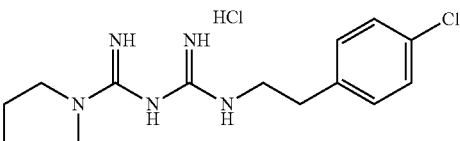

The target compound was obtained as a white solid (0.42 g, 36.8%) in the same manner as in Example 1, except that piperidine cyanoguanidine and 4-chlorophenethylamine were used instead of N,N-dimethylcyanoguanidine and piperidine.

$^1$H NMR (600 MHz, CD$_3$OD) δ 7.40 (m, 2H), 3.01 (m, 8H), 1.70 (i, 4H), 1.55 (m, 2H)

LCMS: 308.1 [M+H]$^+$

Example 14: Synthesis of N1-piperidin-N5-2-chloro)phenethyl Biguanide Hydrochloride

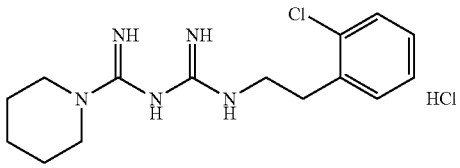 [SMILES: N=C(NCCc1ccccc1Cl)NC(=N)N1CCCCC1 ; Cl]

The target compound was obtained as a white solid (0.42 g, 36.8%) in the same manner as in Example 1, except that piperidine cyanoguanidine and 2-chlorophenethylamine were used instead of N,N-dimethylcyanoguanidine and piperidine.

$^1$H NMR (600 MHz, CD$_3$OD) δ 7.38 (m, 21H), 3.03 (m, 8H), 1.68 (m, 4H), 1.53 (m, 2H)

LCMS: 308.1 [M+H]$^+$

Example 15: Synthesis of N1,N1-dipropyl-N5,N5-dicyclohexyl Biguanide Hydrochloride

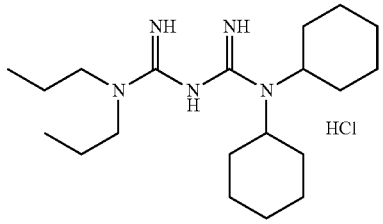 [SMILES: CCCN(CCC)C(=N)NC(=N)N(C1CCCCC1)C1CCCCC1 ; Cl]

The target compound was obtained as a white solid (0.27 g, 21.1%) in the same manner as in Example 1, except that N,N-propylcyanoguanidine and dicyclohexylamine were used instead of N,N-dimethylcyanoguanidine and piperidine.

¹H NMR (600 MHz, DMSO) δ 2.55 (m, 6H), 1.49 (m, 20H), 1.44 (m, 4H), 0.96 (m, 6H)
LCMS: 350.1 [M+H]⁺

Example 16: Synthesis of N1,N1-dipropyl-N5N-dipropyl Biguanide Hydrochloride

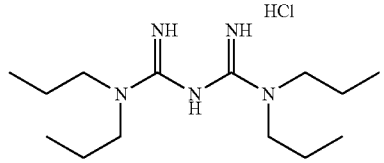 [SMILES: Cl ; CCCN(CCC)C(=N)NC(=N)N(CCC)CCC]

The target compound was obtained as a white solid (0.36 g, 25.0%) in the same manner as in Example 1, except that N1N-dipropylcyanoguanidine and dipropylamine were used instead of N,N-dimethlcyanoguanidine and piperidine.
¹H NMR (600 MHz, DMSO) δ 3.30 (m, 8H), 1.48 (m, 8H), 0.80 (m, 12H)
LCMS: 270.2 [M+H]⁺

Example 17: Synthesis of N1-isopropyl-N5-(4-chloro)phenyl Biguanide Hydrochloride

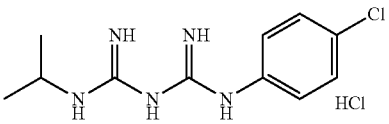 [SMILES: CC(C)NC(=N)NC(=N)Nc1ccc(Cl)cc1 ; Cl]

The target compound was obtained as a white solid (3.00 g, 45.0%) in the same manner as in Example 1, except that isopropylcyanoguanidine and 2-chloroaniline were used instead of N,N-dimethylcyanoguanidine and piperidine.
¹H NMR (600 MHz, DMSO) δ 7.17 (d, J=7.8 Hz, 2H), 6.40 (d, J=7.8 Hz, 2H), 2.97 (m, 1H), 1.05 (m, 6H)
LCMS: 254.1 [M+H]⁺

Example 18: Synthesis of N1-(4-methyl)piperazin-N5-(4-trifluoromethyl)benzyl Biguanide Hydrochloride

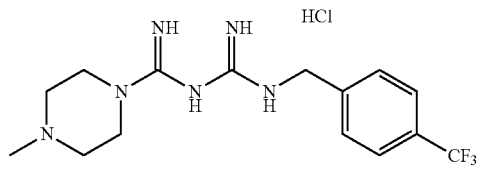 [SMILES: Cl ; CN1CCN(C(=N)NC(=N)NCc2ccc(C(F)(F)F)cc2)CC1]

The target compound was obtained as a white solid (0.29 g, 40.0%) in the same manner as in Example 1, except that 4-methylpiperazinecyanoguanidine and 4-trifluoromethyl benzylamine were used instead of N,N-dimethylcyanoguanidine and piperidine.
¹H NMR (600 MHz, DMSO) δ 7.70 (d, J=7.8 Hz, 2H), 7.52 (d, J=7.8 Hz, 2H), 4.40 (d, J=5.4 Hz, 2H), 3.33 (min, 4H), 2.25 (m, 4H), 2.16 (s, 3H)
LCMS: 343.2 [M+H]⁺

Example 19: Synthesis of N1-(4-methyl)piperazin-N5-(4-trifluoromethyl)phenyl Biguanide Hydrochloride

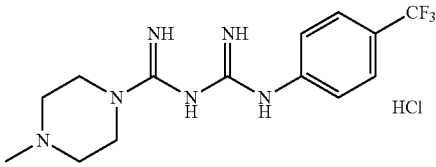 [SMILES: CN1CCN(C(=N)NC(=N)Nc2ccc(C(F)(F)F)cc2)CC1 ; Cl]

The target compound was obtained as a white solid (0.18 g, 10.0%) in the same manner as in Example 1, except that 4-methylpiperazinecyanoguanidine and 4-trifluoromethyl-aniline were used instead of N1-dimethylcyanoguanidine and piperidine.
¹H NMR (600 MHz, DMSO) δ 764 (m, 4H), 3.30 (m, 4H), 2.25 (m, 4H), 2.19 (s, 3H)
LCMS: 329.2 [M+H]⁺

Example 20: Synthesis of N1-(4-methyl)piperazin-N5-(3-trifluoromethyl)benzyl Biguanide Hydrochloride

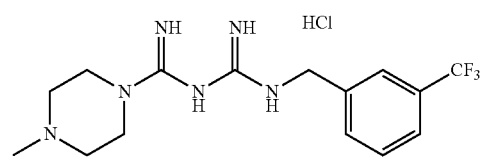 [SMILES: Cl ; CN1CCN(C(=N)NC(=N)NCc2cccc(C(F)(F)F)c2)CC1]

The target compound was obtained as a white solid (0.15 g, 23.0%) in the same manner as in Example 1, except that 4-methylpiperazinecyanoguanidine and 3-trifluoromethyl-benzyl amine were used instead of N,N-dimethylcyanoguanidine and piperidine.
¹H NMR (600 MHz, DMSO) δ 7.62 (m, 4H), 4.41 (d, J=6 Hz, 2H), 3.48 (m, 4H), 2.60 (m, 4H), 2.36 (s, 3H)
LCMS: 343.2 [M+H]⁺

Example 21: Synthesis of N1-(4-methyl)piperazin-N5-(3-trifluoromethyl)phenyl Biguanide Hydrochloride

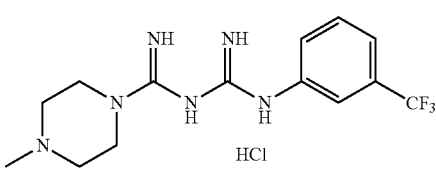 [SMILES: CN1CCN(C(=N)NC(=N)Nc2cccc(C(F)(F)F)c2)CC1 ; Cl]

The target compound was obtained as a white solid (0.51 g, 52.0%) in the same manner as in Example 1, except that 4-methylpiperazinecyanoguanidine and 3-trifluoromethyl-aniline were used instead of N,N-dimethylcyanoguanidine and piperidine.
¹H NMR (600 MHz, DMSO) δ 7.82 (s, 1H), 7.59 (d, J=8.4 Hz, 1H), 7.54 (t, J=8.4 Hz, 1H), 7.37 (d, J=8.4 Hz, 1H), 3.47 (m, 4H), 2.34 (m, 4H), 2.19 (s, 3H)
LCMS: 329.2 [M+H]⁺

Example 22: Synthesis of N1-(4-methyl)piperazin-N5-(3-trifluoromethoxy)phenyl Biguanide Hydrochloride

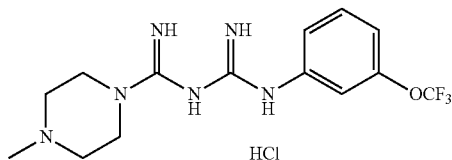 [SMILES: CN1CCN(C(=N)NC(=N)Nc2cccc(OC(F)(F)F)c2)CC1 ; Cl]

The target compound was obtained as a white solid (0.10 g, 15.5%) in the same manner as in Example 1, except that 4-methylpiperazinecyanoguanidine and 3-trifluoromethoxyaniline were used instead of N,N-dimethylcyanoguanidine and piperidine.

$^1$H NMR (600 MHz, DMSO) δ 7.52 (s, 1H), 7.42 (t, J=8.4 Hz, 1H), 7.30 (d, J=8.4 Hz, 1H), 700 (d, J=8.4 Hz, 1H) 3.47 (min, 4H), 2.35 (m, 4H), 2.19 (s, 3H)

LCMS: 345.2 [M+H]$^+$

Example 23: Synthesis of N1-(4-ethoxy)piperidin-N5-(4-trifluoromethyl)phenyl Biguanide Hydrochloride

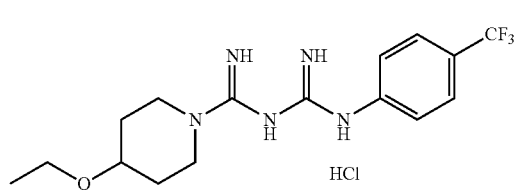 [SMILES: CCOC1CCN(C(=N)NC(=N)Nc2ccc(C(F)(F)F)cc2)CC1 ; Cl]

The target compound was obtained as a white solid (0.04 g, 47.0%) in the same manner as in Example 1, except that 4-ethoxypiperidine cyanoguanidine and 3-trifluoromethyl-aniline were used instead of N,N-dimethylcyanoguanidine and piperidine.

$^1$H NMR (600 MHz, DMSO) δ 7.64 (m, 4H), 3.70 (m, 3H), 3.48 (m, 2H), 3.28 (m, 2H), 1.86 (m, 2H), 1.52 (m, 2H), 1.12 (m, 3H)

LCMS: 358.2 [M+H]$^+$

Example 24: Synthesis of N1-(4-ethoxy)piperidin-N5-(3-trifluoromethyl)phenyl Biguanide Hydrochloride

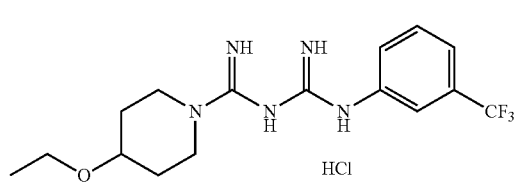 [SMILES: CCOC1CCN(C(=N)NC(=N)Nc2cccc(C(F)(F)F)c2)CC1 ; Cl]

The target compound was obtained as a white solid (0.12 g, 60.6%) in the same manner as in Example 1, except that 4-ethoxypiperidine cyanoguanidine and 3-trifluoromethyl-aniline were used instead of N,N-dimethylcyanoguanidine and piperidine.

$^1$H NMR (600 MHz, DMSO) δ 7.60 (d, J=7.8 Hz, 1H), 7.53 (t, J=7.8 Hz, 1H), 7.36 (d, J=7.8 Hz, 1H), 7.00 (s, 1H), 3.71 (m, 2H), 3.53 (m, 2H), 3.28 (m, 2H), 1.85 (m, 2H), 1.50 (m, 2H), 1.10 (m, 3H)

LCMS: 358.2 [M+H]$^+$

Example 25: Synthesis of N1-(4-ethoxy)piperidin-N5-3-trifluoromethoxy)phenyl Biguanide Hydrochloride

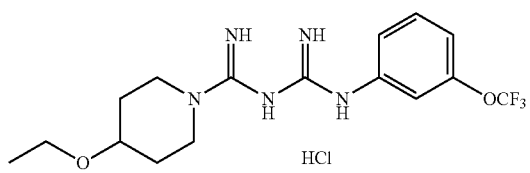 [SMILES: CCOC1CCN(C(=N)NC(=N)Nc2cccc(OC(F)(F)F)c2)CC1 ; Cl]

The target compound was obtained as a white solid (0.10 g, 48.3%) in the same manner as in Example 1, except that 4-ethoxypiperidine cyanoguanidine and 3-trifluoromethoxyaniline were used instead of N,N-dimethylcyanoguanidine and piperidine.

$^1$H NMR (600 MHz, DMSO) δ 7.52 (s, 1H), 7.42 (1, J=8.4 Hz, 1H), 7.30 (d, J=8.4 Hz, 1H), 7.00 (d, J=8.4 Hz, 1H), 3.71 (m, 2H), 3.67 (m, 2H), 3.28 (m, 2H), 1.84 (m, 2H), 1.50 (m, 2H), 1.11 (m, 3H)

LCMS: 374.2 [M+H]$^+$

Example 26: Synthesis of N1-(4-ethoxy)piperidin-N5-(4-trifluoromethoxy)phenyl Biguanide Hydrochloride

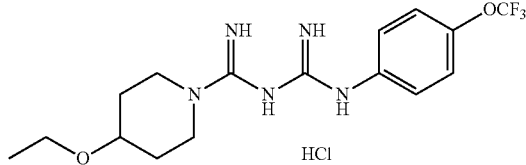 [SMILES: CCOC1CCN(C(=N)NC(=N)Nc2ccc(OC(F)(F)F)cc2)CC1 ; Cl]

The target compound was obtained as a white solid (0.09 g, 44.7%) in the same manner as in Example 1, except that 4-ethoxypiperidine cyanoguanidine and 4-trifluoromethyl-aniline were used instead of N,N-dimethylcyanoguanidine and piperidine.

$^1$H NMR (600 MHz, DMSO) δ 7.47 (m, 2H), 7.30 (m 2H), 3.66 (m, 2H), 3.53 (m, 2H), 3.24 (m, 2H), 1.83 (m, 2H), 1.49 (m, 2H), 1.12 (m, 3H)

LCMS: 374.2 [M+H]$^+$

Example 27: Synthesis of N1-(4-methyl)piperazin-N5-4-chloro)phenyl Biguanide Hydrochloride

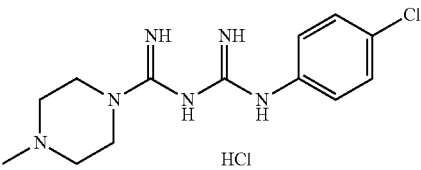 [SMILES: CN1CCN(C(=N)NC(=N)Nc2ccc(Cl)cc2)CC1 ; Cl]

The target compound was obtained as a white solid (0.09 g, 27.0%) in the same manner as in Example 1, except that 4-methylpiperazinecyanoguanidine and 4-chloroaniline were used instead of N,N-dimethylcyanoguanidine and piperidine.

$^1$H NMR (600 MHz, DMSO) δ 7.39 (m, 4H), 3.45 (m, 4H), 2.34 (m, 4H), 2.19 (s, 3H)

LCMS: 295.2 [M+H]$^+$

Example 28: Synthesis of N1-(4-methyl)piperazin-N5-(3-fluoro)phenyl Biguanide Hydrochloride

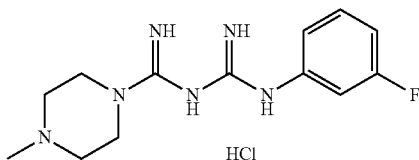 [SMILES: CN1CCN(C(=N)NC(=N)Nc2cccc(F)c2)CC1 ; Cl]

The target compound was obtained as a white solid (0.12 g, 44.3%) in the same manner as in Example 1, except that 4-methylpiperazinecyanoguanidine and 3-fluoroaniline were used instead of N,N-dimethylcyanoguanidine and piperidine.

$^1$H NMR (600 MHz, DMSO) δ 7.36 (d, J=12 Hz, 1H), 7.31 (m, 1H), 7.11 (d, J=7.8 Hz, 1H), 6.85 (t, J==7.8 Hz, 1H), 3.34 (m, 4H), 2.83 (m, 4H), 2.19 (s, 3H)

LCMS: 279.2 [M+H]$^+$

Example 29: Synthesis of N1-(4-methyl)piperazin-N5-(3-chloro)phenyl Biguanide Hydrochloride

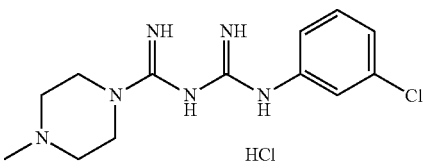 [SMILES: CN1CCN(C(=N)NC(=N)Nc2cccc(Cl)c2)CC1 ; Cl]

The target compound was obtained as a white solid (0.02 g, 6.0%) in the same manner as in Example 1, except that 4-methylpiperazinecyanoguanidine and 3-fluoroaniline were used instead of N,N-dimethylcyanoguanidine and piperidine.

$^1$H NMR (600 MHz, DMSO) δ 7.29 (m, 1H), 7.09 (m, 1H) 7.02 (m, 1H), 6.89 (m, 1H), 3.39 (m, 4H), 2.31 (m, 4H), 2.13 (s, 3H)

LCMS: 295.4 [M+H]$^+$

Example 30: Synthesis of N1-(4-methyl)piperazin-N5-(2-chloro)phenyl Biguanide Hydrochloride

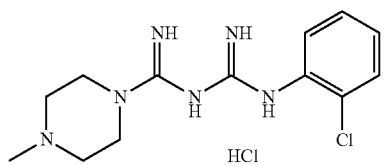 [SMILES: CN1CCN(C(=N)NC(=N)Nc2ccccc2Cl)CC1 ; Cl]

The target compound was obtained as a white solid (0.04 g, 1.0%) in the same manner as in Example 1, except that 4-methylpiperazinecyanoguanidine and 2-chloroaniline were used instead of N,N-dimethylcyanoguanidine and piperidine.

$^1$H NMR (600 Hz, CD$_3$OD) δ 7.43 (m, 1H), 7.25 (m, 1H), 7.08 (m, 1H), 6.98 (m, 1H), 3.34 (s, 4H), 2.37 (s, 4H), 2.17 (s, 3H)

LCMS: 295.4 [M+H]$^+$

Example 31: Synthesis of N1-(4-methyl)piperazin-N5-(4-chloro)benzyl Biguanide Hydrochloride

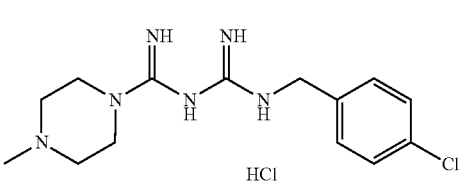 [SMILES: CN1CCN(C(=N)NC(=N)NCc2ccc(Cl)cc2)CC1 ; Cl]

The target compound was obtained as a white solid (0.02 g, 7.0%) in the same manner as in Example 1, except that 4-methylpiperazinecyanoguanidine and 4-chlorobenzylamine were used instead of N,N-dimethylcyanoguanidine and piperidine.

$^1$H NMR (600 Hz, CD$_3$OD) δ 7.12 (m, 4H), 4.17 (s, 2H), 3.27 (s, 4H), 2.25 (s, 4H), 2.14 (s, 3H)

LCMS: 309.4 [M+H]$^+$

Example 32: Synthesis of N1-(4-methyl)piperazin-N5-(2-chloro)benzyl Biguanide Hydrochloride

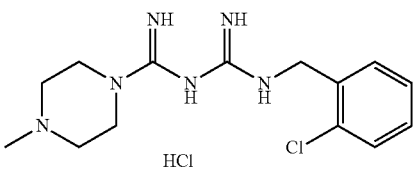 [SMILES: CN1CCN(C(=N)NC(=N)NCc2ccccc2Cl)CC1 ; Cl]

The target compound was obtained as a white solid (0.02 g, 6.0%) in the same manner as in Example 1, except that 4-methylpiperazinecyanoguanidine and 2-chlorobenzylamine were used instead of N,N-dimethlcyanoguanidine and piperidine.

$^1$H NMR (600 Hz, CD$_3$OD) δ 7.42 (m, 2H), 7.31 (m, 2H), 4.52 (s, 2H), 3.76 (s, 4H), 307 (s, 4H), 2.70 (s, 3H)

LCMS: 309.4 [M+H]$^+$

Example 33: Synthesis of N1-(4-methyl)piperazin-N5-(4-fluoro)phenyl Biguanide Hydrochloride

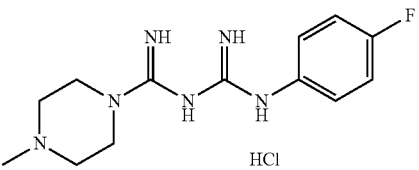 [SMILES: CN1CCN(C(=N)NC(=N)Nc2ccc(F)cc2)CC1 ; Cl]

The target compound was obtained as a white solid (0.10 g, 36.1%) in the same manner as in Example 1, except that 4-methylpiperazinecyanoguanidine and 4-fluoroaniline were used instead of N,N-dimethylcyanoguanidine and piperidine.

$^1$H NMR (600 Hz, DMSO-$d_6$) δ 7.76 (s, 1H), 7.37 (m, 1H), 7.12 (t, 1H), 7.02 (s, 1H) 3.46 (m, 4H), 2.33 (m, 4H), 2.19 (s, 3H)

LCMS: 279.4 [M+H]$^+$

Example 34: Synthesis of
N1-(4-methyl)piperazin-N5-(2-fluoro)phenyl Biguanide Hydrochloride

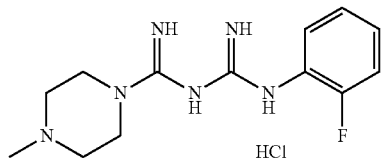 [SMILES: CN1CCN(C(=N)NC(=N)Nc2ccccc2F)CC1 ; Cl]

The target compound was obtained as a white solid (0.10 g, 35.9%) in the same manner as in Example 1, except that 4-methylpiperazinecyanoguanidine and 2-fluoroaniline were used instead of N,N-dimethylcyanoguanidine and piperidine.

$^1$H NMR (600 Hz, DMSO-$d_6$) δ 7.75 (s, 1H), 7.15 (m, 2H), 7.13 (s, 1H), 3.43 (s, 4H), 2.38 (s, 4H), 2.19 (s, 3H)

LCMS: 279.4 [M+H]$^+$

Example 35: Synthesis of
N1-(4-methyl)piperazin-N5-3-chloro)benzyl Biguanide Hydrochloride

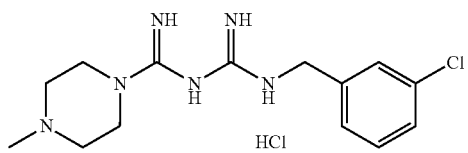 [SMILES: CN1CCN(C(=N)NC(=N)NCc2cccc(Cl)c2)CC1 ; Cl]

The target compound was obtained as a white solid (0.03 g, 0.8%) in the same manner as in Example 1, except that 4-methylpiperazinecyanoguanidine and 3-chlorobenzylamine were used instead of N,N-dimethylcyanoguanidine and piperidine.

$^1$H NMR (600 Hz, CD$_3$OD) δ 7.31 (m, 4H), 418 (s, 2H), 3.47 (s, 4H), 2.44 (s, 4H), 231 (s, 3H)

LCMS: 309.4 [M+H]$^+$

Example 36: Synthesis of
N1-(4-methy)piperazin-N5-butyl Biguanide Hydrochloride

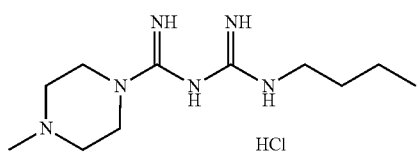 [SMILES: CCCCNC(=N)NC(=N)N1CCN(C)CC1 ; Cl]

The target compound was obtained as a white solid (0.22 g, 41.0%) in the same manner as in Example 1, except that 4-methylpiperazinecyanoguanidine and 1-butylamine were used instead of N,N-dimethylcyanoguanidine and piperidine.

$^1$H NMR (600 Hz, CD$_3$OD) δ 4.29 (m, 21H), 3.71 (s, 4H), 3.50 (m, 3H), 2.98 (m, 4H), 1.68 (m, 2H), 1.45 (m, 2H), 0.98 (m, 3H)

LCMS: 241.2 [M+H]$^+$

Example 37: Synthesis of
N1-(4-methyl)piperazin-N5-(3,4-dichloro)phenyl Biguanide Hydrochloride

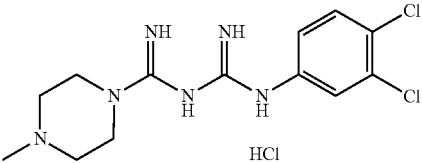 [SMILES: CN1CCN(C(=N)NC(=N)Nc2ccc(Cl)c(Cl)c2)CC1 ; Cl]

The target compound was obtained as a white solid (0.06 g, 12.0%) in the same manner as in Example 1, except that 4-methylpiperazinecyanoguanidine and 3,4-dichloroaniline were used instead of N,N-dimethylcyanoguanidine and piperidine.

$^1$H NMR (600 Hz, CD$_3$OD) δ 7.38 (s, 2H), 7.19 (s, 1H), 3.69 (m, 4H), 3.52 (t, 3H), 297 (s, 4H)

LCMS: 329.1, 331.1 [M, M+2]$^+$

Example 38: Synthesis of
N1-(4-methylpiperazin-N5-(3,4-difluoro)phenyl Biguanide Hydrochloride

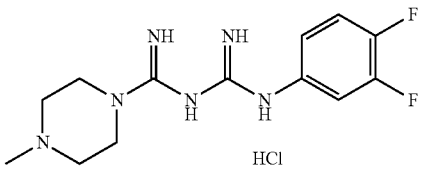 [SMILES: CN1CCN(C(=N)NC(=N)Nc2ccc(F)c(F)c2)CC1 ; Cl]

The target compound was obtained as a white solid (0.06 g, 18.0%) in the same manner as in Example 1, except that 4-methylpiperazinecyanoguanidine and 3,4-difluoroaniline were used instead of N,N-dimethylcyanoguanidine and piperidine.

$^1$H NMR (600 Hz, CD$_3$OD) δ 7.43 (m, 1H), 7.22 (q, 1H), 7.07 (m, 1H), 3.57 (t, 41H), 2.50 (t, 4H), 2.34 (s, 3H)

LCMS: 297.2 [M+H]$^+$

Example 39: Synthesis of N1-(4-methyl)piperazin-N5-(3,5-difluoro)phenyl Biguanide Hydrochloride

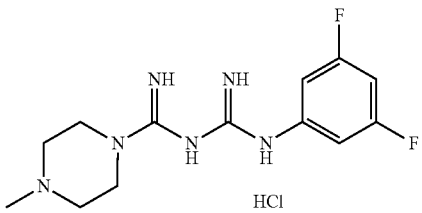 [SMILES: CN1CCN(C(=N)NC(=N)Nc2cc(F)cc(F)c2)CC1 ; Cl]

The target compound was obtained as a white solid (0.49 g, 13.0%) in the same manner as in Example 1, except that 4-methylpiperazinecyanoguanidine and 3,5-difluoroaniline were used instead of N,N-dimethylcyanoguanidine and piperidine.

$^1$H NMR (600 Hz, CD$_3$OD) δ 7.04 (m, 2H), 665 (m, H), 3.61 (m, 4H), 2.53 (m, 4H), 2.34 (s, 3H)
LCMS: 297.2 [M+H]$^+$

Example 40: Synthesis of N1-(4-methyl)piperazin-N5-(3,4,5-trifluoro)phenyl Biguanide Hydrochloride

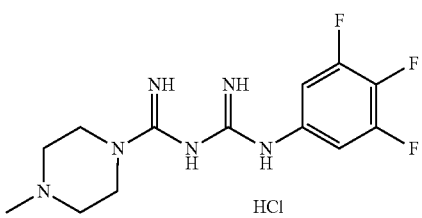 [SMILES: CN1CCN(C(=N)NC(=N)Nc2cc(F)c(F)c(F)c2)CC1 ; Cl]

The target compound was obtained as a white solid (0.12 g, 40.0%) in the same manner as in Example 1, except that 4-methylpiperazinecyanoguanidine and 3,4,5-trifluoroaniline were used instead of N N-dimethylcyanoguanidine and piperidine.

$^1$H NMR (600 Hz, CD$_3$OD) δ 7.20 (m, 2H), 3.58 (m, 4H), 2.52 (m, 4H), 2.34 (s, 3H)
LCMS: 315.2 [M+H]$^+$

Example 41: Synthesis of N1-3-pyridin-N5-(3-trifluoromethyl)phenyl Biguanide Hydrochloride

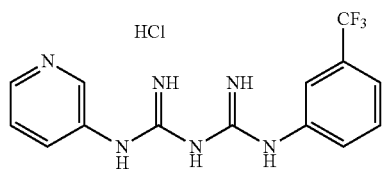

The target compound was obtained as a white solid (0.25 g, 43.0%) in the same manner as in Example 1, except that 3-pyridinecyanoguanidine and 3-trifluoroaniline were used instead of N,N-dimethylcyanoguanidine and piperidine.

$^1$H NMR (600 Hz, CD$_3$OD) δ 8.56 (m, 21-H) 8.33 (s, 1H), 7.85 (d, 1H), 7.67 (s, 1H), 7.52 (m, 2H), 7.45 (m, 1H)
LCMS: 323.2 [M+H]$^+$

Example 42: Synthesis of N1-3-pyridin-N5-(3-trifluoromethoxy)benzyl Biguanide Hydrochloride

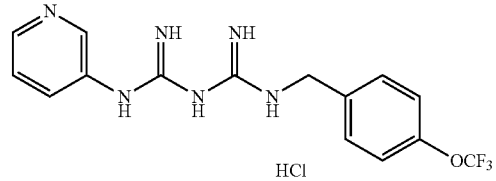 [SMILES: N=C(NCc1ccc(OC(F)(F)F)cc1)NC(=N)Nc1cccnc1 ; Cl]

The target compound was obtained as a white solid (0.20 g, 37.0%) in the same manner as in Example 1, except that 3-pyridinecyanoguanidine and 4-trifluoromethoxybenzylamine were used instead of N,N-dimethylcyanoguanidine and piperidine.

$^1$H NMR (600 Hz, CD$_3$OD) δ 8.48 (s, 1H), 8.00 (d, 1H), 7.82 (s, 1H), 7.75 (s, 1H), 7.51 (s, 1H), 7.31 (m, 4H), 4.50 (min, 2H)
LCMS: 353.2 [M+H]$^+$

Example 43: Synthesis of N1-3-pyridin-N5-(3-trifluoromethyl)benzyl Biguanide Hydrochloride

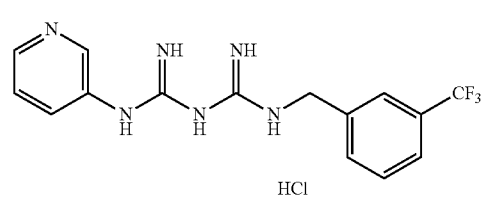 [SMILES: N=C(NCc1cccc(C(F)(F)F)c1)NC(=N)Nc1cccnc1 ; Cl]

The target compound was obtained as a white solid (0.05 g, 8.0%) in the same manner as in Example 1, except that 3-pyridinecyanoguanidine and 3-trifluoromethylbenzylamine were used instead of N,N-dimethylcyanoguanidine and piperidine.

$^1$H NMR (600 Hz, CD$_3$OD) δ 9.01 (m, H), 8.87 (s, 1H), 8.49 (m, 2H), 8.08 (m, 1H), 7.65 (3H), 4.69 (m, 2H)
LCMS: 337.2 [M+H]$^+$

Example 44: Synthesis of N1-(3-methyl)piperidin-N5-cyclopentyl Biguanide Hydrochloride

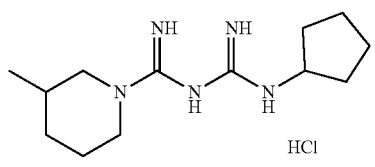 [SMILES: CC1CCCN(C(=N)NC(=N)NC2CCCC2)C1 ; Cl]

The target compound was obtained as a white solid (0.05 g, 14.6%) in the same manner as in Example 1, except that 3-methylpiperidinecyanoguanidine and cyclopentylamine were used instead of N,N-dimethylcyanoguanidine and piperidine.

$^1$H NMR (400 Hz, CD$_3$OD) δ 4.05 (m, 4H), 2.96 (m, 1H), 2.68 (m, 1H), 1.98 (m, 3H), 1.65 (m, 9H), 1.32 (m, 1H), 0.95 (m, 4H)

LCMS: 252.2 [M+H]$^+$

Example 45: Synthesis of
N1-(3-methyl)piperidin-N5-(4-methoxy)piperidine
Biguanide Hydrochloride

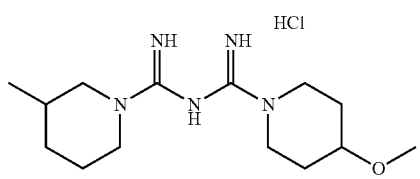

The target compound was obtained as a white solid (0.03 g, 8.5%) in the same manner as in Example 1, except that 3-methylpiperidinecyanoguanidine and 4-methoxypiperidine were used instead of N,N-dimethylcyanoguanidine and piperidine.

$^1$H NMR (600 Hz, CD$_3$OD) δ 3.96 (m, 2H), 3.75 (m, 2H), 3.48 (m, 1H), 3.34 (s, 3H), 3.30 (m, 1H), 2.80 (m, 1H), 2.59 (m, 1H), 1.88 (m, 3H), 1.66 (m, 2H), 1.58 (m, 3H), 1.23 (m, 1H), 0.95 (d, 3H)

LCMS: 282.2 [M+H]$^+$

Example 46: Synthesis of
N1-(3-methyl)piperidin-N5-(4-ethos)piperidine
Biguanide Hydrochloride

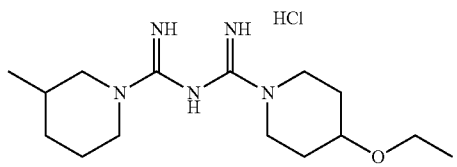 [SMILES: Cl ; CCOC1CCN(C(=N)NC(=N)N2CCCC(C)C2)CC1]

The target compound was obtained as a white solid (0.04 g, 12.2%) in the same manner as in Example 1, except that 3-methylpiperidinecyanoguanidine and 4-ethoxypiperidine were used instead of N,N-dimethylcyanoguanidine and piperidine.

$^1$H NMR (600 Hz, CD$_3$OD) δ 4.01 (m, 2H), 3.82 (m, 2H), 3.58 (m, 4H), 3.31 (m, 4H), 2.80 (m, 1H), 2.58 (m, 1H), 2.01 (m, 3H), 1.56 (m, 5H), 1.28 (m, 1H), 0.95 (d, 3H)

LCMS: 292.2 [M+H]$^+$

Example 47: Synthesis of
N1-(3-methyl)piperidin-N5-pyrazin-2-yl Biguanide
Hydrochloride

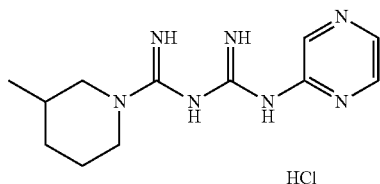 [SMILES: CC1CCCN(C(=N)NC(=N)Nc2cnccn2)C1 ; Cl]

The target compound was obtained as a white solid (0.01 g, 4.7%) in the same manner as in Example 1, except that 3-methylpiperidinecyanoguanidine and pyrazin-2-amine were used instead of N,N-dimethylcyanoguanidine and piperidine.

$^1$H NMR (600 Hz, CD$_3$OD) δ 8.48 (s, 1H), 8.27 (s, 1H), 8.22 (s, 11H), 3.73 (m, 2H), 3.12 (m, 1H), 2.75 (m, 1H), 1.80 (m, 4H), 1.23 (m, 1H), 0.92 (d, 3H)

LCMS: 262.1 [M+H]$^+$

Example 48: Synthesis of
N1-(4-methyl)piperidin-N5-(4-bromo)phenyl
Biguanide Hydrochloride

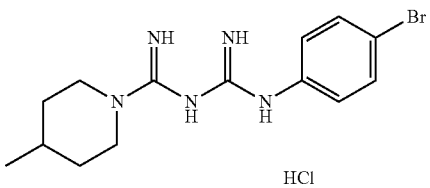 [SMILES: CC1CCN(C(=N)NC(=N)Nc2ccc(Br)cc2)CC1 ; Cl]

The target compound was obtained as a white solid (0.32 g, 49.3%) in the same manner as in Example 1, except that 4-methylpiperidinecyanoguanidine and 4-bromoaniline were used instead of N,N-dimethylcyanoguanidine and piperidine.

$^1$H NMR (600 Hz, CD$_3$OD) δ 7.45 (m, 2H), 7.30 (m, 2H), 4.07 (s, 2H), 2.99 (t, 2H), 1.72 (m, 2H), 1.68 (m, 1H), 1.19 (m, 2H), 0.98 (d, 3H)

LCMS: 338.0, 340.2 [M, M+2]$^+$

Example 49: Synthesis of N1-(4-methy)piperidin-
N5-(3-trifluoromethoxy)phenyl Biguanide Hydrochloride

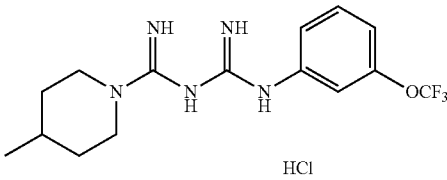 [SMILES: CC1CCN(C(=N)NC(=N)Nc2cccc(OC(F)(F)F)c2)CC1 ; Cl]

The target compound was obtained as a white solid (0.49 g, 71.9%) in the same manner as in Example 1, except that 4-methylpiperidinecyanoguanidine and 3-trifluoromethoxyaniline were used instead of NAN-dimethylcyanoguanidine and piperidine.

¹H NMR (600 Hz, CD₃OD) δ 7.53 (s, 1H), 7.37 (t, 1H), 7.26 (m, 1H), 6.97 (m, 1H), 4.07 (s, 2H), 3.02 (t, 2H), 1.74 (m, 2H), 1.70 (m, 1H), 1.23 (m, 2H), 1.00 (d, 3H)
LCMS: 344.2 [M+H]⁺

Example 50: Synthesis of N1-(4-methyl)piperidin-N5-(3-trifluoromethyl)phenyl Biguanide Hydrochloride

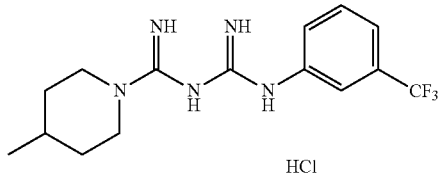 [SMILES: CC1CCN(C(=N)NC(=N)Nc2cccc(C(F)(F)F)c2)CC1 ; Cl]

The target compound was obtained as a white solid (0.50 g, 77.0%) in the same manner as in Example 1, except that 4-methylpiperidinecyanoguanidine and 3-trifluoromethylaniline were used instead of N,N-dimethylcyanoguanidine and piperidine.
¹H NMR (600 Hz, CD₃OD) δ 7.84 (s, 1H), 7.55 (d, 1H), 7.48 (t, 1H), 7.31 (d, 1H), 4.07 (s, 2H), 3.02 (t, 2H), 1.76 (m, 2H), 1.70 (m, 1H), 1.23 (nm, 2H), 0.99 (d, 3H)
LCMS: 328.2 [M+H]⁺

Example 51: Synthesis of N1-(3-methyl)piperidin-N5-(3-trifluoromethyl)phenyl Biguanide Hydrochloride

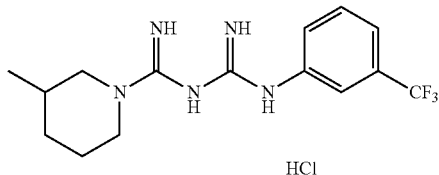 [SMILES: CC1CCCN(C(=N)NC(=N)Nc2cccc(C(F)(F)F)c2)C1 ; Cl]

The target compound was obtained as a white solid (0.49 g, 75.4%) in the same manner as in Example 1, except that 3-methylpiperidinecyanoguanidine and 3-trifluoromethylaniline were used instead of N,N-dimethylcyanoguanidine and piperidine.
¹H NMR (600 Hz, CD₃OD) δ 7.86 (s, 1H), 7.55 (d, 1H), 7.48 (t, 1H), 7.31 (d, 1H), 3.97 (s, 2H), 3.01 (t, 1H), 2.71 (t, 1H), 1.89 (m, 1H), 1.77 (m, 1H), 1.70 (m, 1H), 1.59 (m, 1H), 1.23 (m, 1H), 0.94 (d, 3H)
LCMS: 328.2 [M+H]⁺

Example 52: Synthesis of N1-(4-methyl)piperidin-N5-(4-trifluoromethoxy)phenyl Biguanide Hydrochloride

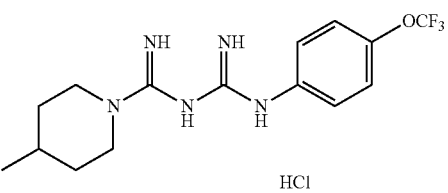 [SMILES: CC1CCN(C(=N)NC(=N)Nc2ccc(OC(F)(F)F)cc2)CC1 ; Cl]

The target compound was obtained as a white solid (0.68 g, 60.0%) in the same manner as in Example 1, except that 4-methylpiperidinecyanoguanidine and 4-trifluoromethoxyaniline were used instead of N,N-dimethylcyanoguanidine and piperidine.
¹H NMR (600 Hz, CD₃OD) δ 7.45 (d, 2H), 7.23 (d, 2H), 4.07 (d, 2H), 2.99 (t, 2H), 1.75 (d, 2H), 1.69 (m, 1H), 1.21 (m, 2H), 0.99 (d, 3H)
LCMS: 344.2 [M+H]⁺

Example 53: Synthesis of N1-(4-methyl)piperidin-N5-(4-trifluoromethyl)phenyl Biguanide Hydrochloride

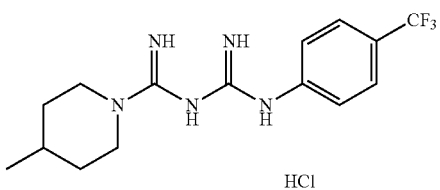 [SMILES: CC1CCN(C(=N)NC(=N)Nc2ccc(C(F)(F)F)cc2)CC1 ; Cl]

The target compound was obtained as a white solid (0.66 g, 61.0%₀) in the same manner as in Example 1, except that 4-methylpiperidinecyanoguanidine and 4-trifluoromethylaniline were used instead of N,N-dimethylcyanoguanidine and piperidine.
¹H NMR (600 Hz, CD₃OD) δ 7.58 (s, 4H), 4.06 (s, 2H), 3.04 (t, 2H), 1.76 (m, 2H), 1.70 (m, 1H), 1.23 (m, 2H), 1.00 (d, 3H)
LCMS: 328.2 [M+H]⁺

Example 54: Synthesis of N1-(4-methyl)piperidin-N5-(3-trifluoromethyl-4-fluoro)phenyl Biguanide Hydrochloride

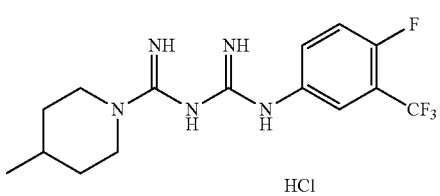 [SMILES: CC1CCN(C(=N)NC(=N)Nc2ccc(F)c(C(F)(F)F)c2)CC1 ; Cl]

The target compound was obtained as a white solid (0.76 g, 66.7%) in the same manner as in Example 1, except that 4-methylpiperidinecyanoguanidine and 3-trifluoromethyl-4-fluoroaniline were used instead of N,N-dimethylcyanoguanidine and piperidine.
¹H NMR (600 Hz, CD₃OD) δ 7.83 (d, 1H), 7.58 (m, 1H), 7.28 (t, 1H), 3.01 (t, 2H), 1.75 (m, 2H), 1.56 (m, 1H), 1.21 (m, 2H), 0.99 (d, 3H)
LCMS: 3.46.2 [M+H]⁺

Example 55: Synthesis of N1-4-methyl)piperidin-N5-(4-chloro)phenyl Biguanide Hydrochloride

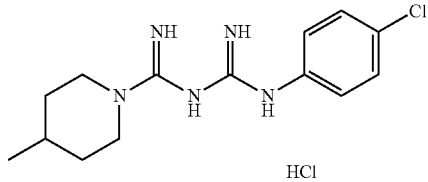 [SMILES: CC1CCN(C(=N)NC(=N)Nc2ccc(Cl)cc2)CC1 ; Cl]

The target compound was obtained as a white solid (0.30 g, 50.3%) in the same manner as in Example 1, except that 4-methylpiperidinecyanoguanidine and 4-chloroaniline were used instead of N,N-dimethylcyanoguanidine and piperidine.

$^1$H NMR (600 Hz, CD$_3$OD) δ 7.36 (d, 2H), 7.31 (d, 2H), 4.07 (d, 2H), 2.99 (t, 2H), 1.75 (m, 2H), 1.69 (m, 1H), 1.21 (m, 2H), 0.99 (d, 3H)

LCMS: 294.2 [M+H]$^+$

Example 56: Synthesis of N1-(4-methyl)piperidin-N5-(4-fluoro)phenyl Biguanide Hydrochloride

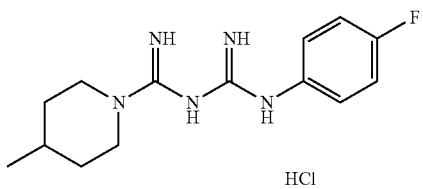 [SMILES: CC1CCN(C(=N)NC(=N)Nc2ccc(F)cc2)CC1 ; Cl]

The target compound was obtained as a white solid (0.44 g, 7.1%) in the same manner as in Example 1, except that 4-methylpiperidinecyanoguanidine and 4-fluoroaniline were used instead of N,N-dimethylcyanoguanidine and piperidine.

$^1$H NMR (600 Hz, CD$_3$OD) δ 7.35 (m, 2H), 7.06 (m, 2H), 4.07 (d, 2H), 2.97 (t, 2H), 1.74 (d, 2H), 1.67 (m, 1H), 1.98 (m, 2H), 0.99 (d, 3H)

LCMS: 278.2 [M+H]$^+$

Example 57: Synthesis of N1-(4-methyl)piperidin-N5-(3-fluoro-4-trifluoromethyl)phenyl Biguanide Hydrochloride

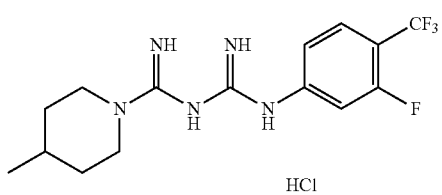 [SMILES: CC1CCN(C(=N)NC(=N)Nc2ccc(C(F)(F)F)c(F)c2)CC1 ; Cl]

The target compound was obtained as a white solid (0.29 g, 42.7%) in the same manner as in Example 1, except that 4-methylpiperidinecyanoguanidine and 3-fluoro-4-trifluoromethylaniline were used instead of N,N-dimethylcyanoguanidine and piperidine.

$^1$H NMR (600 Hz, CD$_3$OD) δ 7.62 (m, 2H), 7.24 (d, 2H), 4.07 (s, 2H), 3.06 (s, 2H), 1.78 (d, 2H), 1.72 (m, 1H), 1.26 (d, 2H), 0.98 (d, 3H)

LCMS: 346.2 [M+H]$^+$

Example 58: Synthesis of N1-(4-methyl)piperidin-N5-(3-trifluoromethyl-4-chloro)phenyl Biguanide Hydrochloride

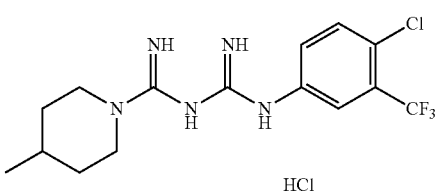

The target compound was obtained as a white solid (0.50 g, 70.1%) in the same manner as in Example 1, except that 4-methylpiperidinecyanoguanidine and 3-trifluoromethyl-4-chloroaniline were used instead of N,N-dimethylcyanoguanidine and piperidine.

$^1$H NMR (600 Hz, CD$_3$OD) δ 7.95 (s, 1H), 7.53 (q, 2H), 4.07 (s, 2H), 3.04 (1, 2H), 1.76 (m, 2H), 1.72 (m, 1H), 1.24 (m, 2H), 1.00 (d, 3H)

LCMS: 362.2 [M+H]$^+$

Example 59: Synthesis of N1-(4-methyl)piperidin-N5-(3-fluoro-4-trifluoromethoxy)phenyl Biguanide Hydrochloride

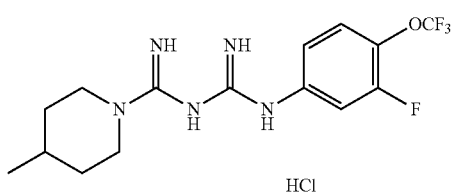 [SMILES: CC1CCN(C(=N)NC(=N)Nc2ccc(OC(F)(F)F)c(F)c2)CC1 ; Cl]

The target compound was obtained as a white solid (0.35 g, 49.7%) in the same manner as in Example 1, except that 4-methylpiperidinecyanoguanidine and 3-fluoro-4-trifluoromethoxyaniline were used instead of N,N-dimethylcyanoguanidine and piperidine.

$^1$H NMR (600 Hz, CD$_3$OD) δ 7.56 (d, 1H), 7.33 (t, 1H), 7.15 (d, 1H), 4.06 (s, 2H), 3.03 (t, 2H), 1.77 (d, 2H), 1.70 (m, 1H), 1.24 (min, 2H), 1.00 (d, 3H)

LCMS: 362.2 [M+H]$^+$

Example 60: Synthesis of N1-(4-methyl)piperidin-N5-(3-trifluoromethyl)benzyl Biguanide Hydrochloride

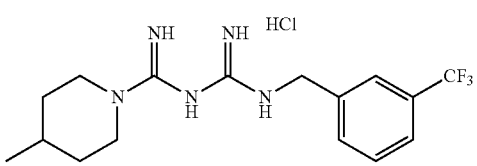 [SMILES: Cl ; CC1CCN(C(=N)NC(=N)NCc2cccc(C(F)(F)F)c2)CC1]

The target compound was obtained as a white solid (0.11 g, 17.2%) in the same manner as in Example 1, except that 4-methylpiperidinecyanoguanidine and 3-trifluoromethylbenzylamine were used instead of N,N-dimethylcyanoguanidine and piperidine.

$^1$H NMR (600 Hz, CD$_3$OD) δ 7.63 (s, 1H), 7.54 (m, 3H), 4.46 (s, 2H), 3.95 (d, 2H), 2.88 (t, 2H), 1.67 (m, 3H), 1.13 (m, 2H), 0.95 (d, 3H)

LCMS: 342.2 [M+H]$^+$

Example 61: Synthesis of N1 (4-methyl)piperidin-N5-(4-trifluoromethyl)benzyl Biguanide Hydrochloride

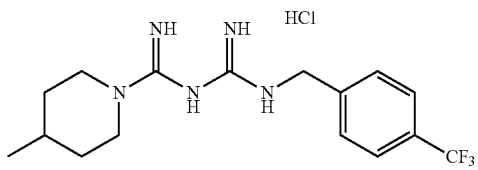 [SMILES: Cl ; CC1CCN(C(=N)NC(=N)NCc2ccc(C(F)(F)F)cc2)CC1]

The target compound was obtained as a white solid (0.07 g, 10.8%) in the same manner as in Example 1, except that 4-methylpiperidinecyanoguanidine and 4-trifluoromethyl benzylamine were used instead of NA-dimethylcyanoguanidine and piperidine.

$^1$H NMR (600 Hz, CD$_3$OD) δ 7.64 (d, 2H), 7.51 (d, 2H), 4.47 (s, 2H), 3.98 (d, 2H), 2.89 (t, 2H), 1.65 (m, 3H), 1.10 (nm, 2H), 0.94 (d, 3H)

LCMS: 342.2 [M+H]$^+$

Example 62: Synthesis of N1-(3,5-dimethyl)piperidin-N5-(4-trifluoromethoxy)phenyl Biguanide Hydrochloride

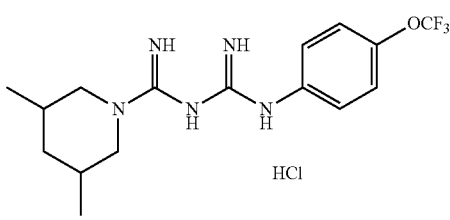 [SMILES: CC1CC(C)CN(C(=N)NC(=N)Nc2ccc(OC(F)(F)F)cc2)C1 ; Cl]

The target compound was obtained as a white solid (0.21 g, 30.0%) in the same manner as in Example 1, except that 3,5-dimethylpiperidinecyanoguanidine and 4-trifluoromethoxy aniline were used instead of N,N-dimethylcyanoguanidine and piperidine.

$^1$H NMR (600 Hz, DMSO-d$_6$) δ 7.77 (s, 2H), 7.49 (m, 2H), 7.30 (m, 2H), 6.98 (s, 2H), 3.95 (d, 2H), 2.48 (t, 2H), 1.77 (d, 1H), 1.64 (s, 2H), 0.88 (s, 6H), 0.87 (m, 1H)

LCMS: 358.2 [M+H]$^+$

Example 63: Synthesis of N1-(3,5-dimethyl)piperidin-N5-(4-trifluoromethyl)phenyl Biguanide Hydrochloride

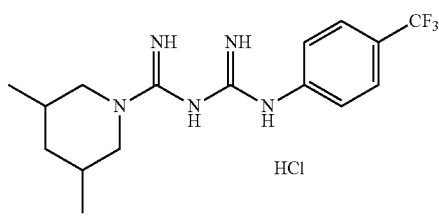 [SMILES: CC1CC(C)CN(C(=N)NC(=N)Nc2ccc(C(F)(F)F)cc2)C1 ; Cl]

The target compound was obtained as a white solid (0.25 g, 31.2%) in the same manner as in Example 1, except that 3,5-dimethylpiperidine cyanoguanidine and 4-trifluoromethylaniline were used instead of N,N-dimethylcyanoguanidine and piperidine.

$^1$H NMR (600 MHz, CD$_3$OD) δ 8.90 (m, 1H), 8.56 (m, 1H), 8.43 (m, 1H), 8.39 (m, 1H), 7.91 (m, 1H), 7.76 (m, 2H), 7.41 (m, 1H)

LC-MS m/z 339.2 [M+1]$^+$

Example 64: Synthesis of N1-(3,5-dimethyl)piperidin-N5=(4-fluoro)phenyl Biguanide Hydrochloride

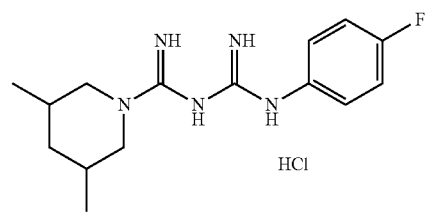 [SMILES: CC1CC(C)CN(C(=N)NC(=N)Nc2ccc(F)cc2)C1 ; Cl]

The target compound was obtained as a white solid (0.30 g, 29.8%) in the same manner as in Example 1, except that 3,5-dimethylpiperidinecyanoguanidine and 4-fluoroaniline were used instead of N,N-dimethylcyanoguanidine and piperidine.

$^1$H NMR (600 Hz, DMSO-d$_6$) δ 7.69 (s, 1H), 7.45 (m, 1H), 7.39 (m, 2H), 7.32 (m, 1H), 6.95 (s, 1H), 3.95 (d, 2H), 2.40 (t, 2H), 1.68 (d, 1H), 1.62 (s, 2H), 0.88 (s, 6H), 089 (m, 1H)

LCMS: 292.2 [M+H]$^+$

Example 65: Synthesis of N1-(3,5-dimethyl)piperidin-N5-(3-trifluoromethyl-4-fluoro)phenyl Biguanide Hydrochloride

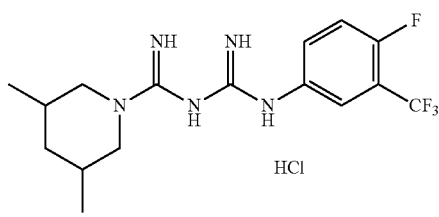 [SMILES: CC1CC(C)CN(C(=N)NC(=N)Nc2ccc(F)c(C(F)(F)F)c2)C1 ; Cl]

The target compound was obtained as a white solid (0.15 g, 15.0%) in the same manner as in Example 1, except that 3,5-dimethylpiperidinecyanoguanidine and 3-trifluoromethyl-4-fluoroaniline were used instead of N,N-dimethlcyanoguanidine and piperidine.

$^1$H NMR (600 Hz, DMSO-d$_6$) δ 7.89 (m, 1H), 7.80 (s, IT), 7.65 (m, 1H), 7.44 (m, 1H), 7.04 (m, 1H), 3.98 (d, 2H), 2.43 (m, 2H), 1.77 (d, 1H), 1.62 (s, 2H), 0.83 (s, 6H), 0.84 (m, 1H)

LCMS: [M+H]$^+$

Example 66: Synthesis of N1-2,5-dihydro-1H-pyrrol-N5-pyridin-3-yl Biguanide Hydrochloride

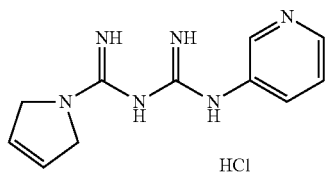 [SMILES: N=C(NC(=N)N1CC=CC1)Nc1cccnc1 ; Cl]

The target compound was obtained as a white solid (0.18 g, 31.3%) in the same manner as in Example 1, except that 2,5-dihydro-1H-pyrrolecyanoguanidine and pyrazin-2-amine were used instead of N,N-dimethylcyanoguanidine and piperidine.

$^1$H NMR (600 Hz, CD$_3$OD) δ 8.57 (s, 1H), 8.23 (s, 1H), 7.91 (s, 1H), 7.36 (s, 1H), 5.91 (s, 2H), 4.24 (d, 4H)

LCMS: 231.2 [M+H]$^+$

Example 67: Synthesis of N1-2,5-dihydro-1H-pyrrol-N5-2,5-dihydro-1H-pyrrole Biguanide Hydrochloride

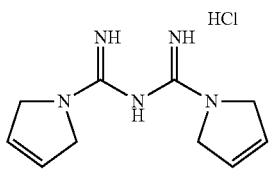 [SMILES: Cl ; N=C(NC(=N)N1CC=CC1)N1CC=CC1]

The target compound was obtained as a white solid (0.40 g, 28.8%) in the same manner as in Example 1, except that 2,5-dihydro-1H-pyrrolecyanoguanidine and 2,5-dihydro-1H-pyrrole were used instead of N,N-dimethylcyanoguanidine and piperidine.

$^1$H NMR (600 Hz, CD$_3$OD) δ 599 (s, 4H), 4.39 (m, 8H)
LCMS: 206.2 [M+H]$^+$

Example 68: Synthesis of N1-1,2,3,6-tetrahydropyridin-N5-1,2,3,6-tetrahydropyridine Biguanide Hydrochloride

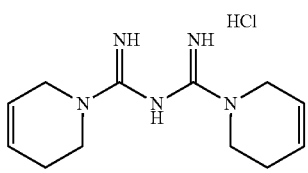 [SMILES: Cl ; N=C(NC(=N)N1CC=CCC1)N1CC=CCC1]

The target compound was obtained as a white solid (0.59 g, 16.3%) in the same manner as in Example 1, except that 1,2,3,6-tetrahydropyridinecyanoguanidine and 1,2,3,6-tetrahydropyridine were used instead of N,N-dimethlcyanoguanidine and piperidine.

$^1$H NMR (600 Hz, CD$_3$OD) δ 5.97 (s, 2H), 5.75 (d, 2H), 3.98 (s, 4H), 2.25 (s, 4H)

LCMS: 234.2 [M+H]$^+$

Example 69: Synthesis of N1-(4-methyl)piperidin-N5-(4-aminoethyl)phenyl Biguanide Hydrochloride

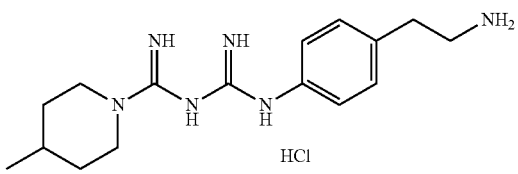 [SMILES: CC1CCN(C(=N)NC(=N)Nc2ccc(CCN)cc2)CC1 ; Cl]

The target compound was obtained as a white solid (0.06 g, 16.9%) in the same manner as in Example 1, except that 4-methylpiperidinecyanoguanidine and 4-aminoethylaniline were used instead of N,N-dimethylcyanoguanidine and piperidine.

$^1$H NMR (600 Hz, CD$_3$OD) δ 7.37 (d, 2H), 7.25 (d, 2H), 4.09 (d, 2H), 3.2 (m, 2H), 3.01 (m, 4H), 1.75 (m, 3H), 1.21 (m, 2H), 0.98 (m, 3H)

LCMS: 303.2 [M+H]$^+$

Example 70: Synthesis of N1-pyrrolidin-N5-(4-acetyl)phenyl Biguanide Hydrochloride

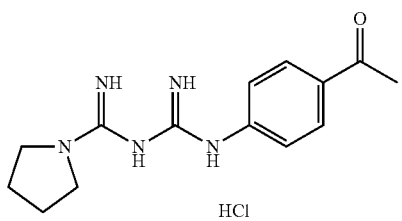 [SMILES: CC(=O)c1ccc(NC(=N)NC(=N)N2CCCC2)cc1 ; Cl]

The target compound was obtained as a white solid (0.49 g, 44.1%) in the same manner as in Example 1, except that pyrrolidinecyanoguanidine and 4-acetylaniline were used instead of N,N-dimethylcyanoguanidine and piperidine.

$^1$H NMR (600 Hz, CD$_3$OD) δ 7.95 (d, 2H), 7.56 (d, 2H), 3.31 (d, 4H), 2.56 (s, 3H), 2.10 (d, 4H)

LCMS: 274.2 [M+H]$^+$

Example 71: Synthesis of N1-piperidin-N5-(4-morpholin-4-yl)phenyl Biguanide Hydrochloride

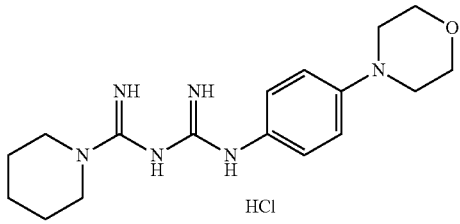 [SMILES: N=C(NC(=N)N1CCCCC1)Nc1ccc(N2CCOCC2)cc1 ; Cl]

The target compound was obtained as a white solid (0.93 g, 69.1%) in the same manner as in Example 1, except that piperidinecyanoguanidine and 4-morpholin-4-ylaniline were used instead of N,N-dimethylcyanoguanidine and piperidine.

$^1$H NMR (600 Hz, CD$_3$OD) δ 7.22 (d, 2H), 6.96 (d, 2H), 3.83 (m, 4H), 3.50 (m, 4H), 3.12 (m, 41H), 1.69 (m, 2H), 1.63 (s, 4H)

LCMS: 331.2 [M+1H]$^+$

Example 72: Synthesis of N1-pyrrolidin-N5-4-bromo)phenyl Biguanide Hydrochloride

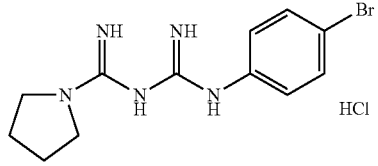 [SMILES: N=C(NC(=N)N1CCCC1)Nc1ccc(Br)cc1 ; Cl]

The target compound was obtained as a white solid (0.91 g, 73.2%) in the same manner as in Example 1, except that pyrrolidinecyanoguanidine and 4-bromoaniline were used instead of N,N-dimethylcyanoguanidine and piperidine.

$^1$H NMR (600 Hz, CD$_3$OD) δ 7.43 (d, 2H), 7.35 (d, 2H), 3.48 (d, 4H), 2.06 (d, 4H)

LCMS: 310.0, 312.0 [M, M+2]$^+$

Example 73: Synthesis of N1-piperidin-N5-(4-methoxy)phenyl Biguanide Hydrochloride

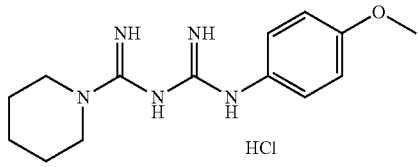 [SMILES: COc1ccc(NC(=N)NC(=N)N2CCCCC2)cc1 ; Cl]

The target compound was obtained as a white solid (0.31 g, 30.4%) in the same manner as in Example 1, except that piperidinecyanoguanidine and 4-methoxyaniline were used instead of N,N-dimethylcyanoguanidine and piperidine.

$^1$H NMR (600 Hz, CD$_3$OD) δ 7.24 (d, 2H), 6.91 (d, 2H), 3.78 (s, 3), 3.50 (s, 4H), 1.69 (m, 2H), 1.62 (s, 4H)

LCMS: 276.2 [M+H]$^+$

Example 74: Synthesis of N1-piperidin-N5-(2-propyl)phenyl Biguanide Hydrochloride

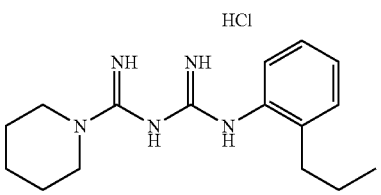 [SMILES: Cl ; CCCc1ccccc1NC(=N)NC(=N)N1CCCCC1]

The target compound was obtained as a white solid (0.67 g, 63.6%) in the same manner as in Example 1, except that piperidinecyanoguanidine and 2-propylaniline were used instead of N,N-dimethylcyanoguanidine and piperidine.

$^1$H NMR (600 Hz, CD$_3$OD) δ 7.31 (m, 1H), 7.27 (m, 1H), 7.21 (m, 2H), 3.47 (m, 4H), 2.65 (t, 2H), 1.63 (m, 8H), 0.97 (m, 3H)

LCMS: 288.2 [M+H]$^+$

Example 75: Synthesis of N1-pyrrolidin-N5-(2-trifluoromethyl)phenyl Biguanide Hydrochloride

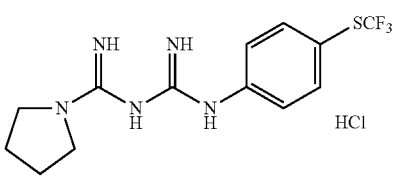

The target compound was obtained as a white solid (0.53 g, 44.4%) in the same manner as in Example 1, except that pyrrolidinecyanoguanidine and 2-trifluoromethylaniline were used instead of N,N-dimethlcyanoguanidine and piperidine.

$^1$H NMR (600 Hz, CD$_3$OD) δ 770 (m, 3H), 7.60 (s, 1H), 3.04 (d, 4H), 2.08 (d, 4H)

LCMS: 300.2 [M+H]$^+$

Example 76: Synthesis of N1-pyrrolidin-N5-(2-chloro-5-trifluoromethyl)phenyl Biguanide Hydrochloride

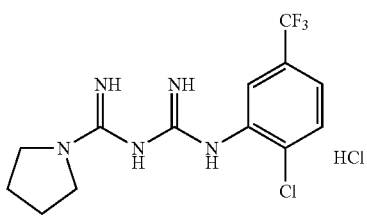 [SMILES: N=C(NC(=N)N1CCCC1)Nc1cc(C(F)(F)F)ccc1Cl ; Cl]

The target compound was obtained as a white solid (0.36 g, 32.3%) in the same manner as in Example 1, except that pyrrolidinecyanoguanidine and 2-chloro-5-trifluoromethylaniline were used instead of N,N-dimethylcyanoguanidine and piperidine.

¹H NMR (600 Hz, CD₃OD) δ 7.58 (s, 1H), 7.32 (m, 2H), 3.24 (d, 4H), 2.21 (d, 4H)
LCMS: 334.2 [M+H]⁺

Example 77: Synthesis of N1-pyrrolidin-N5-(3-chloro-4-fluoro)phenyl Biguanide Hydrochloride

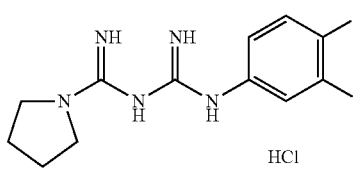

The target compound was obtained as a white solid (0.72 g, 54.3%) in the same manner as in Example 1, except that pyrrolidinecyanoguanidine and 3-chloro-4-fluoroaniline were used instead of N,N-dimethylcyanoguanidine and piperidine.
¹H NMR (600 Hz, CD₃OD) δ 7.64 (m, 1H), 7.29 (m, 1H), 7.21 (m, 1H), 3.49 (d, 4H), 2.07 (d, 4H)
LCMS: 284.2 [M+H]⁺

Example 78: Synthesis of N1-pyrrolidin-N5-(2,3-dichloro)phenyl Biguanide Hydrochloride

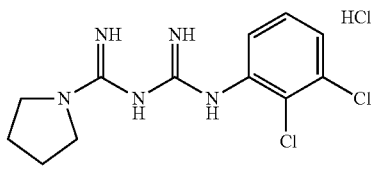 [SMILES: N=C(NC(=N)N1CCCC1)Nc1cccc(Cl)c1Cl ; Cl]

The target compound was obtained as a white solid (0.74 g, 60.88%) in the same manner as in Example 1, except that pyrrolidinecyanoguanidine and 2,3-dichloroaniline were used instead of N,N-dimethylcyanoguanidine and piperidine.
¹H NMR (600 Hz, CD₃OD) δ 7.77 (m, 1H), 7.22 (m, 1H), 7.25 (m, 1H), 3.46 (d, 4H), 2.05 (4H)
LCMS: 300.1 [M+H]⁺

Example 79: Synthesis of N1-pyrrolidin-N5-(4-trifluoromethylthio)phenyl Biguanide Hydrochloride

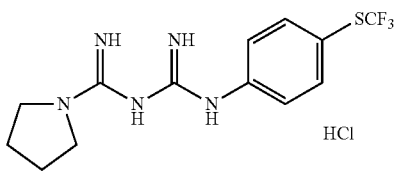

The target compound was obtained as a white solid (0.94 g, 71.2%) in the same manner as in Example 1, except that pyrrolidinecyanoguanidine and 4-trifluoromethylthioaniline were used instead of N,N-dimethylcyanoguanidine and piperidine.

¹H NMR (600 Hz, CD₃OD) δ 7.59 (m, 4H), 3.52 (d, 4H), 208 (d, 4H)
LCMS: 332.2 [M+H]⁺

Example 80: Synthesis of N1-pyrrolidin-N5-(2,6-difluoro)phenyl Biguanide Hydrochloride

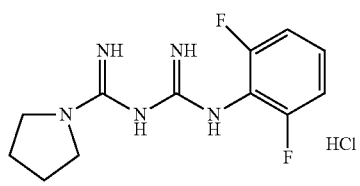 [SMILES: N=C(NC(=N)N1CCCC1)Nc1c(F)cccc1F ; Cl]

The target compound was obtained as a white solid (0.09 g, 48.0%) in the same manner as in Example 1, except that pyrrolidinecyanoguanidine and 2,6-difluoroaniline were used instead of N,N-dimethylcyanoguanidine and piperidine.
¹H NMR (600 MHz, DMSO-d₆) δ 7.47 (s, 2H), 7.34 (m, 1H), 7.14 (t, 2H), 7.01 (s, 2H) 3.27 (d, 4H), 1.94 (d, 4H)
LCMS: 268.2 [M+H]⁺

Example 81: Synthesis of 3-(3-(imino(piperidin-1-yl)methyl)guanidino)benzyl) Triphenylphosphonium Chloride

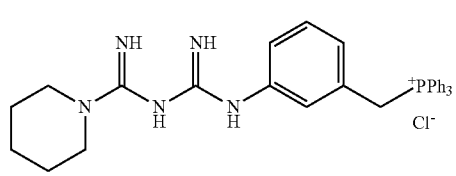

The target compound was obtained as a white solid (0.01 g, 5.0%) in the same manner as in Example 1, except that piperidinecyanoguanidine and (3-aminobenzyl)triphenylphosphonium chloride were used instead of N,N-dimethylcyanoguanidine and piperidine.
¹H NMR (400 MHz, DMSO-d₆) δ7.82 (m, 6H), 7.77 (m, 3H), 7.50 (m, 6H), 7.38 (m, 2H), 7.17 (m, 1H), 4.65 (s, 2H), 3.11 (t, 4H), 1.30 (m, 4H)
LCMS: 554.2 [M+H]⁺

Example 82: Synthesis of N1-pyrrolidin-N5-methyl-N5-(4-trifluoromethoxy)phenyl Biguanide Hydrochloride

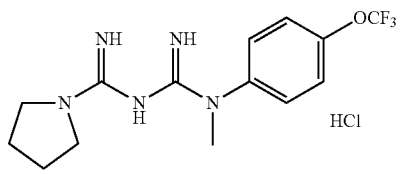 [SMILES: CN(C(=N)NC(=N)N1CCCC1)c1ccc(OC(F)(F)F)cc1 ; Cl]

The target compound was obtained as a white solid (1.32 g, 76.7%) in the same manner as in Example 1, except that pyrrolidinecyanoguanidine and N-methyl-4-trifluoromethoxyaniline were used instead of N,N-dimethylcyanoguanidine and piperidine.

¹H NMR (600 MHz, CD₃OD) δ7.41 (d, 2H), 7.20 (d, 2H), 3.20 (d, 4H), 2.84 (s, 3H), 1.98 (d, 4H)

LCMS: 330.1 [M+H]⁺

Example 83: Synthesis of N-pyrrolidin-N5-(4-trifluoromethoxy)phenyl Biguanide Hydrochloride

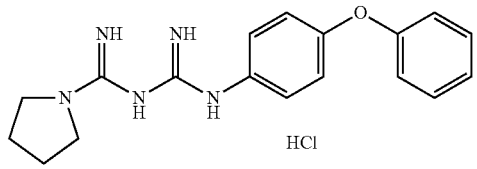 [SMILES: N=C(NC(=N)N1CCCC1)Nc1ccc(Oc2ccccc2)cc1 ; Cl]

The target compound was obtained as a white solid (0.09 g, 8.3%) in the same manner as in Example 1, except that pyrrolidinecyanoguanidine and 4-phenoxyaniline were used instead of N,N-dimethylcyanoguanidine and piperidine.

¹H NMR (400 MHz, CD₃OD) δ7.31 (m, 4H), 7.03 (m, 1H), 6.89 (m, 4H), 3.43 (d, 4H), 1.98 (d, 4H)

LCMS: 324.2 [M+H]⁺

Example 84: Synthesis of N1,N1-dimethyl-N5-(4-trifluoromethoxy)phenyl Biguanide Hydrochloride

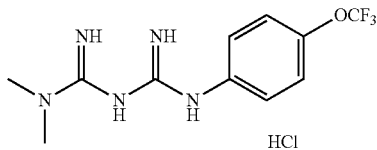 [SMILES: CN(C)C(=N)NC(=N)Nc1ccc(OC(F)(F)F)cc1 ; Cl]

The target compound was obtained as a white solid (0.30 g, 34.5%) in the same manner as in Example 1, except that 4-trifluoromethoxyaniline was used instead of piperidine ¹H NMR (600 MHz, DMSO) δ 7.41 (d, J=8 Hz, 2H), 7.20 (d, J=8 Hz, 2H), 3.20 (s, 6H)

LCMS: 290.1 [M+H]⁺

Example 85: Synthesis of N1,N1-dimethyl-N5-methyl-N5-(4-trifluoromethoxy)phenyl Biguanide Hydrochloride

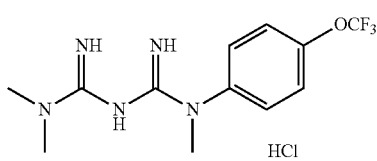 [SMILES: CN(C)C(=N)NC(=N)N(C)c1ccc(OC(F)(F)F)cc1 ; Cl]

The target compound was obtained as a white solid (0.70 g, 77.0%) in the same manner as in Example 1, except that N-methyl-4-trifluoromethoxyaniline was used instead of piperidine.

¹H NMR (600 MHz, DMSO) δ 7.39 (d, J=8 Hz, 2H), 7.18 (d, J=8 Hz, 2H), 3.23 (s, 6H), 2.86 (s, 3H)

LCMS: 304.2 [M+H]⁺

Example 86: Synthesis of N1-2-(benzo[d][1,3]dioxol-5-yl)ethyl-N5-thiophenethyl Biguanide Hydrochloride

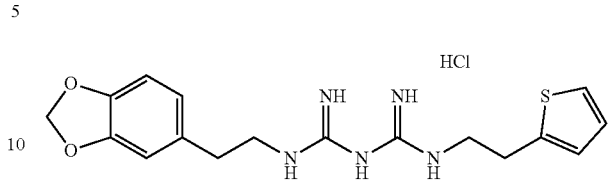

The target compound was obtained as a white solid (0.09 g, 10.0%) in the same manner as in Example 1, except that 2-(benzo[d][1,3]dioxol-5-yl)ethylcyanoguanidine and thiophenethyl were used instead of N,N-dimethylcyanoguanidine and piperidine.

¹H NMR (600 Hz, CD₃OD) δ 6.91 (m, 3H), 6.70 (m, 3H), 5.83 (s, 2H), 3.10 (m, 4H), 2.99 (m, 2H), 2.70 (m, 2H)

LCMS: 360.1 [M+H]⁺

Example 87: Synthesis of N1-(N-acetyl)piperazin-N5-(4-trifluoromethoxy)phenyl Biguanide Hydrochloride

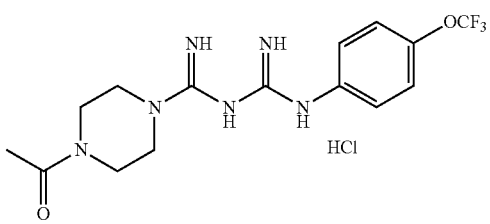 [SMILES: CC(=O)N1CCN(C(=N)NC(=N)Nc2ccc(OC(F)(F)F)cc2)CC1 ; Cl]

The target compound was obtained as a white solid (0.40 g, 40.6%) in the same manner as in Example 1, except that N-acetylpiperazinecyanoguanidine and 4-trifluoromethoxyaniline were used instead of N,N-dimethylcyanoguanidine and piperidine.

¹H NMR (600 MHz, CD₃OD) δ 7.47 (d, 2H), 7.23 (d, 2H), 3.69 (m, 3H), 3.79 (m, 4H), 2.13 (s, 4H)

LCMS: 373.1 [M+H]⁺

Example 88: Synthesis of N1-2-(benzo[d][1,3]dioxol-5-yl)ethyl-N5-butyl Biguanide Hydrochloride

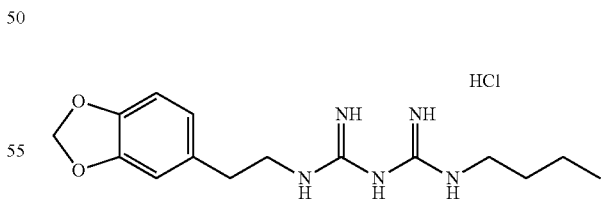

The target compound was obtained as a white solid (0.01 g, 22.0%) in the same manner as in Example 1, except that 2-(benzo[d][1,3]dioxol-5-yl)ethylcyanoguanidine and 1-butylamine were used instead of N,N-dimethylcyanoguanidine and piperidine.

¹H NMR (600 Hz, CD₃OD) δ 6.70 (m, 3H), 5.83 (s, 2H), 3.10 (t, 4H), 2.99 (m, 2H), 2.70 (t, 2H), 1.5 (m, 2), 0.99 (m, 3H)

LCMS: 306.2 [M+H]⁺

Example 89: Synthesis of N1-2-(benzo[d][1,3]di-oxol-5-yl)ethyl-N5-phenethyl Biguanide Hydrochloride

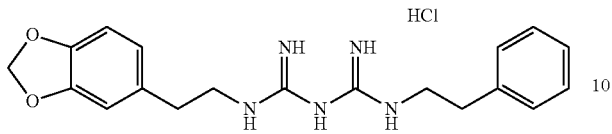

The target compound was obtained as a white solid (0.50 g, 28.0%) in the same manner as in Example 1, except that 2-(benzo[d][1,3]dioxol-5-yl)ethylcyanoguanidine and phenethyl were used instead of N,N-dimethylcyanoguanidine and piperidine.

$^1$H NMR (600 Hz, CD$_3$OD) δ 7.21 (m, 5H), 6.78 (m, 3H), 5.99 (s, 2H), 3.13 (t, 4H), 2.99 (m, 21H), 2.87 (t, 2H)

LCMS: 354.2 [M+H]$^+$

Example 90: Synthesis of N1-(4,4-difluoro)piperidin-N5-(3,4-dichloro)phenyl Biguanide Hydrochloride

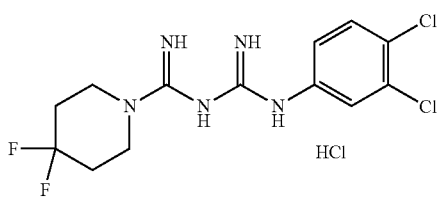 [SMILES: N=C(NC(=N)N1CCC(F)(F)CC1)Nc1ccc(Cl)c(Cl)c1 ; Cl]

The target compound was obtained as a white solid (0.20 g, 50.0%) in the same manner as in Example 1, except that 4,4-difluoropiperidine cyanoguanidine and 3,4-dichloroaniline were used instead of N,N-dimethylcyanoguanidine and piperidine.

Example 91: Synthesis of N1-(4,4-difluoro)piperidin-N5-(5,6,7,8-tetrahydronaphthalene) Biguanide Hydrochloride

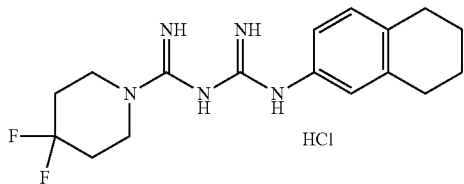 [SMILES: N=C(NC(=N)N1CCC(F)(F)CC1)Nc1ccc2c(c1)CCCC2 ; Cl]

The target compound was obtained as a white solid (0.30 g, 60.0%) in the same manner as in Example 1, except that 4,4-difluoropiperidine cyanoguanidine and 5,6,7,8-tetrahydronaphthalen-2-amine were used instead of N,N-dimethylcyanoguanidine and piperidine.

Example 92: Synthesis of N1-butyl-N2-cycloheptyl Biguanide Hydrochloride

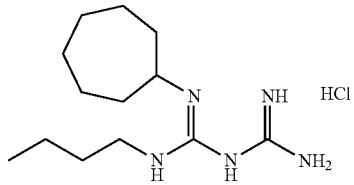 [SMILES: CCCCN/C(=N\C1CCCCCC1)NC(=N)N ; Cl]

1-Butyl-3-cycloheptylthiourea (4.1 g, 18.0 mmol) was dissolved in ethanol (150 mL) at room temperature. Mercury oxide (7.8 g, 30.1 mmol) and guanidine hydrochloride (5.1 g, 54.0 mmol) were added thereto and the mixture was stirred under reflux for 15 hours. The reaction mixture was filtered, concentrated under reduced pressure, and separated and purified using a chromatography in a condition where the ratio of methylene chloride to methyl alcohol was 9:1 and the target compound was obtained as a white solid (2.00 g, 38.0%).

$^1$H NMR (600 MHz, DMSO) δ 3.55 (nm, 1H), 3.01 (m, 2H), 1.77 (m, 2H), 1.58 (s, 2H), 1.49 (m, 8H), 1.37 (m, 2H), 1.28 (m, 2H), 0.84 (m, 3H)

LCMS: 254.4 [M+H]$^+$

Example 93: Synthesis of N1,N1-dimethyl-N2-(4-fluoro)benzyl-N5-piperidine Biguanide Hydrochloride

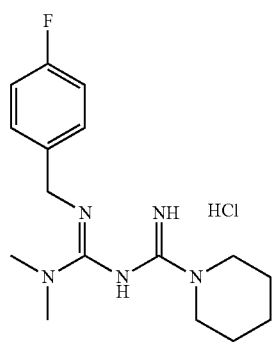 [SMILES: CN(C)/C(=N\Cc1ccc(F)cc1)NC(=N)N1CCCCC1 ; Cl]

The target compound was obtained as a white solid (0.15 g, 42.3%) in the same manner as in Example 92, except that 1-(1,1-dimethyl)-3-(4-fluoro)benzylthiourea and piperidine-guanidine were used instead of 1-butyl-3-cycloheptylthiourea and guanidine hydrochloride.

$^1$H NMR (600 MHz, CDCl$_3$) δ 7.34 (m, 1H), 6.96 (m, 2H), 3.57 (s, 2H), 2.84 (m, 6H), 1.64 (m, 4H), 1.42 (m, 4H), 1.19 (m, 2H)

LCMS: 306.1 [M+H]$^+$

Example 94: Synthesis of N1-phenyl-N2-phenethyl Biguanide Hydrochloride

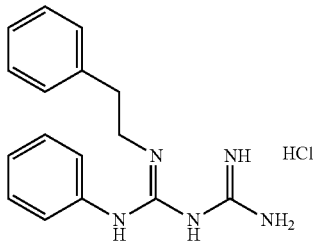 [SMILES: N=C(N)N/C(=N/CCc1ccccc1)Nc1ccccc1 ; Cl]

The target compound was obtained as a white solid (0.02 g, 2.0%) in the same manner as in Example 92, except that 1-phenyl-3-phenethylthiourea was used instead of 1-butyl-3-cycloheptylthiourea.

$^1$H NMR (600 MHz, DMSO) δ 7.32 (m, 7H), 7.17 (d, J=8.4 Hz, 2H), 7.17 (t, J=8.4 Hz, 1H), 3.38 (m, 2H), 2.86 (t, J=7.2 Hz, 2H)
LCMS: 282.1 [M+H]$^+$

Example 95: Synthesis of N1-phenethyl-N2-(4-bromo)phenyl Biguanide Hydrochloride

The target compound was obtained as a white solid (0.15 g, 31.5%) in the same manner as in Example 92, except that 1-phenethyl-3-(4-bromo)phenylthiourea was used instead of 1-butyl-3-cycloheptylthiourea.

$^1$H NMR (400 MHz, DMSO) δ 8.01 (s, 1H), 7.86 (d, J=7.6 Hz, 1H), 7.46 (d, J=7.6 Hz, 1H), 7.32 (t, J=7.6 Hz, 2H), 7.23 (m, 3H), 7.14 (t, J=7.6 Hz, 1H), 3.44 (m, 2H), 2.77 (t, J=7.2 Hz, 2H)
LCMS: 360.0 [M+H]$^+$

Example 96: Synthesis of N1-benzyl-N2-methyl-N5,N5-dimethyl Biguanide Hydrochloride

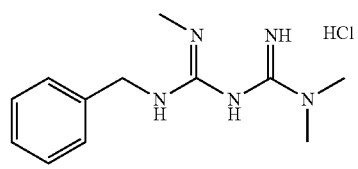 [SMILES: C/N=C(\NCc1ccccc1)NC(=N)N(C)C ; Cl]

The target compound was obtained as a white solid (0.03 g, 2.0%) in the same manner as in Example 92, except that 1-benzyl-3-methylthiourea and N,N-dimethylguanidine were used instead of 1-butyl-3-cycloheptylthiourea and guanidine hydrochloride.

$^1$H NMR (600 MHz, DMSO) δ 7.35 (d, J=7.2 Hz, 2H), 7.29 (t, J=7.2 Hz, 2H), 7.20 (t, J=7.2 Hz, 1H), 4.52 (s, 2H), 3.45 (s, 3H), 3.29 (s, 3H), 2.97 (s, 6H)
LCMS: 234.1 [M+H]$^+$

Example 97: Synthesis of N1-phenethyl-N2-methyl-N5,N5-dimethyl Biguanide Hydrochloride

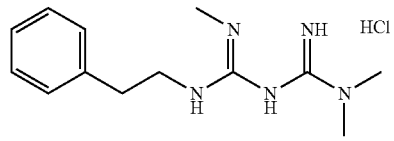 [SMILES: C/N=C(\NCCc1ccccc1)NC(=N)N(C)C ; Cl]

The target compound was obtained as a white solid (0.35 g, 24.8%) in the same manner as in Example 92, except that 1-phenethyl-3-methylthiourea and N,N-dimethylguanidine were used instead of 1-butyl-3-cycloheptylthiourea and guanidine hydrochloride.

$^1$H NMR (600 MHz, CD$_3$OD) δ 7.28 (m, 2H), 7.20 (m, 3H), 3.53 (m, 2H), 3.30 (m, 8H), 3.13 (s, 3H)
LCMS: 248.1 [M+H]$^+$

Example 98: Synthesis of N1-(4-chloro)benzyl-N2-cycloheptyl Biguanide Hydrochloride

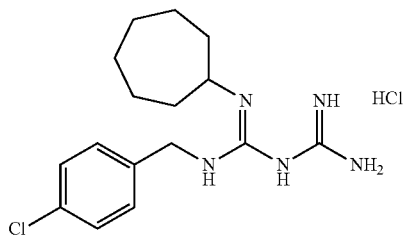 [SMILES: N=C(N)N/C(=N/C1CCCCCC1)NCc1ccc(Cl)cc1 ; Cl]

The target compound was obtained as a white solid (0.18 g, 27.0%) in the same manner as in Example 92, except that 1-(4-chloro)benzyl-3-cycloheptylthiourea was used instead of 1-butyl-3-cycloheptylthiourea.

$^1$H NMR (400 MHz, DMSO) δ 7.37 (q, J=7.2 Hz, 4H), 4.26 (s, 2H), 3.53 (m, 1H), 1.48 (m, 12H)
LCMS: 322.2 [M+H]$^+$

Example 99: Synthesis of N1-piperidin-N2-(2-thiophen-2-yl)ethyl Biguanide Hydrochloride

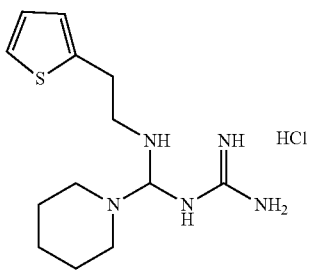 [SMILES: N=C(N)NC(NCCc1cccs1)N1CCCCC1 ; Cl]

The target compound was obtained as a white solid (0.06 g, 22.0%) in the same manner as in Example 92, except that 1-piperidin-3-thiophenenethylthiourea was used instead of 1-butyl-3-cycloheptylthiourea.

¹H NMR (600 MHz, DMSO) δ 7.36 (d, J=7.8 Hz, 1H), 6.97 (d, J=7.8 Hz, 1H), 6.89 (m, 1H), 3.29 (m, 4H), 3.04 (m, 41H), 1.57 (m, 6H)

LCMS: 280.2 [M+H]⁺

Example 100: Synthesis of N1-(benzo[d][1,3]di-oxol-5-yl)methyl-N2-ethyl Biguanide Hydrochloride

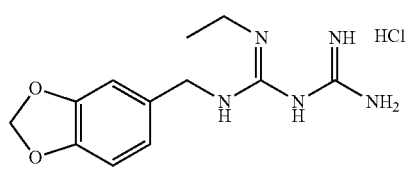 [SMILES: CC/N=C(\NCc1ccc2c(c1)OCO2)NC(=N)N ; Cl]

The target compound was obtained as a white solid (0.33 g, 34.0%) in the same manner as in Example 92, except that 1-(benzo[d][1,3]dioxol-5-yl)methyl-3-ethylthiourea was used instead of 1-butyl-3-cycloheptylthiourea.

¹H NMR (600 MHz, DMSO) δ 6.91 (s, 1H), 6.86 (d, J=7.8 Hz, 1H), 6.78 (m, 1H), 5.99 (s, 2H), 3.11 (m, 2H), 1.09 (t, J=7.2 Hz, 3H)

LCMS: 264.1 [M+H]⁺

Example 101: Synthesis of N1-2-(benzo[d][1,3]dioxol-5-yl)ethyl-N2-ethyl Biguanide Hydrochloride

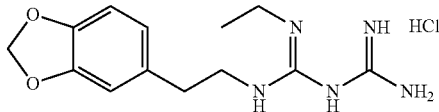 [SMILES: CC/N=C(\NCCc1ccc2c(c1)OCO2)NC(=N)N ; Cl]

The target compound was obtained as a white solid (0.17 g, 48.0%) in the same manner as in Example 92, except that 1-(2-(benzo[d][1,3]dioxol-5-yl)ethyl)-3-ethylthiourea was used instead of 1-butyl-3-cycloheptylthiourea.

¹H NMR (600 Hz, CD₃OD) δ 6.75 (m, 2H), 6.69 (m, H), 4.85 (s, 2H), 339 (t, 2H), 3.20 (q, 2H), 2.77 (t, 2H), 1.15 (t, 3H)

LCMS: 278.1 [M+H]⁺

Example 102: Synthesis of N1-2-(benzo[d][1,3]dioxol-5-yl)ethyl-N2-methyl Biguanide Hydrochloride

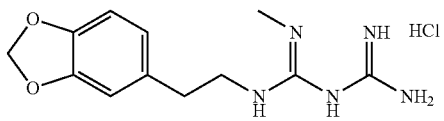 [SMILES: C/N=C(\NCCc1ccc2c(c1)OCO2)NC(=N)N ; Cl]

The target compound was obtained as a white solid (0.12 g, 30.1%) in the same manner as in Example 92, except that 1-(2-(benzo[d][1,3]dioxol-5-yl)ethyl)-3-methylthiourea was used instead of 1-butyl-3-cycloheptylthiourea.

¹H NMR (600 Hz, DMSO-d₆) δ 6.79 (m, 2H), 6.64 (m, 1H), 5.91 (s, 2H), 3.24 (s, 3H), 2.66 (s, 4H)

LCMS: 264.2 [M+H]⁺

Example 103: Synthesis of N1 (2-thiophen-2-yl)ethyl-N2-phenethyl Biguanide Hydrochloride

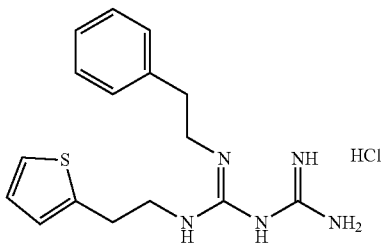 [SMILES: N=C(N)N/C(=N/CCc1ccccc1)NCCc1cccs1 ; Cl]

The target compound was obtained as a white solid (0.58 g, 95.1%) in the same manner as in Example 92, except that 1-thiophenethyl-3-phenethylthiourea was used instead of 1-butyl-3-cycloheptylthiourea.

¹H NMR (600 Hz, CD₃OD) δ 7.42 (m, 5H), 6.70 (m, 3H), 3.10 (m, 4H), 2.90 (m, 4H)

LCMS: 360.1 [M+H]⁺

Example 104: Synthesis of N1-2-thiophen-2-)ethyl-N2-2-benzo[d][1,3]dioxol-5-yl)ethyl Biguanide Hydrochloride

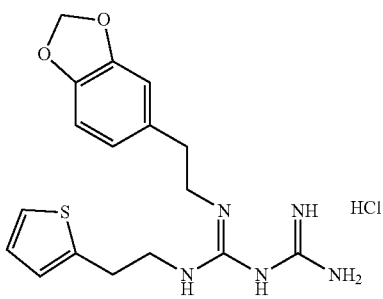 [SMILES: N=C(N)N/C(=N/CCc1ccc2c(c1)OCO2)NCCc1cccs1 ; Cl]

The target compound was obtained as a white solid (0.06 g, 26.7%) in the same manner as in Example 92, except that 1-thiophenethyl-3-(2-(benzo[d][1,3]dioxol-5-yl)ethyl)thiourea was used instead of 1-butyl-3-cycloheptylthiourea.

¹H NMR (600 Hz, CD₃OD) δ 7.01 (m, 1H), 6.98 (m, 2H), 6.70 (m, 3H), 5.83 (s, 2H), 3.10 (m, 4H), 2.99 (m, 2H), 2.70 (m, 2H)

LCMS: 316.2 [M+H]⁺

Example 105: Synthesis of N1-(4-trifluoromethoxy)phenyl-N2-methyl-N5-pyrrolidine Biguanide Hydrochloride

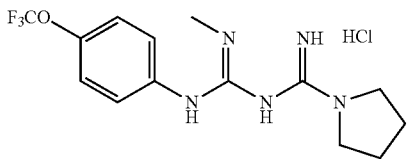 [SMILES: C/N=C(/NC(=N)N1CCCC1)Nc1ccc(OC(F)(F)F)cc1 ; Cl]

The target compound was obtained as a white solid (0.04 g, 8.6%) in the same manner as in Example 92, except that 1-(4-trifluoromethoxy)phenyl-3-methylthiourea and pyrrolidineguanidine were used instead of 1-butyl-3-cycloheptylthiourea and guanidine hydrochloride.

$^1$H NMR (600 MHz, CD$_3$OD) δ7.32 (d, 2H), 7.25 (d, 2H), 3.20 (d, 4H), 2.98 (s, 3H), 1.99 (d, 4H)

LCMS: 330.1 [M+H]$^+$

Example 106: Synthesis of N1-methyl-N1-(4-trifluoromethoxy)phenyl-N2-methyl-N5-pyrrolidine Biguanide Hydrochloride

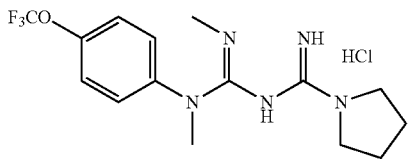 [SMILES: C/N=C(/NC(=N)N1CCCC1)N(C)c1ccc(OC(F)(F)F)cc1 ; Cl]

The target compound was obtained as a white solid (0.01 g, 5.6%) in the same manner as in Example 92, except that 1-(N-methyl-4-trifluoromethoxy)phenyl-3-methylthiourea and pyrrolidineguanidine were used instead of 1-butyl-3-cycloheptylthiourea and guanidine hydrochloride.

$^1$H NMR (600 MHz, CD$_3$OD) δ7.40 (d, 2H), 7.34 (d, 2H), 3.34 (s, 3H), 3.30 (m, 4H), 3.20 (s, 3H), 1.86 (s, 4H)

LCMS: 344.1 [M+H]$^+$

Example 107: Synthesis of N1-(benzo[d][1,3]dioxol-5-yl)methyl-N2-cyclopentyl Biguanide Hydrochloride

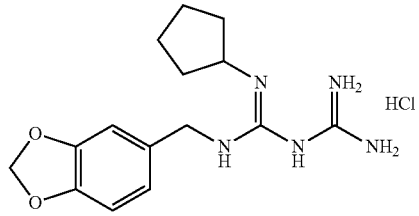 [SMILES: N=C(N)N/C(=N/C1CCCC1)NCc1ccc2c(c1)OCO2 ; Cl]

The target compound was obtained as a white solid (0.65 g, 53.3%) in the same manner as in Example 92, except that 1-(benzo[d][1,3]dioxol-5-yl)methyl-3-cyclopentylthiourea was used instead of 1-butyl-3-cycloheptylthiourea.

$^1$H NMR (600 MHz, CD$_3$OD) δ6.93 (m, 1H), 6.88 (m, 1H) 6.83 (m, 1H), 5.98 (s, 2H), 4.51 (s, 2H), 3.34 (s, 1H), 2.12 (s, 2H), 1.80 (s, 2H), 1.66 (s, 4H)

LCMS: 304.4 [M+H]$^+$

Example 108: Synthesis of N1-methyl Biguanide Hydrochloride

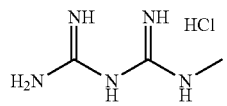

Methylamine hydrochloride (1.3 g, 19.84 mmol) was dissolved in n-butanol (30 mL) at room temperature. Cyanoguanidine (1.68 g, 19.98 mmol) was added thereto and the mixture was stirred under reflux for 15 hours. The reaction mixture was concentrated under reduced pressure, and separated and purified using a chromatography in a condition where the ratio of methylene chloride to methyl alcohol was 9:1 and the target compound was obtained as a white solid (0.90 g, 61.0%).

$^1$H NMR (600 MHz, DMSO) δ 2.86 (s, 3H)

LCMS: 116.1 [M+H]$^+$

Example 109: Synthesis of N1-hexyl Biguanide Hydrochloride

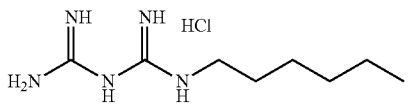

The target compound was obtained as a white solid (0.60 g, 23.0%) in the same manner as in Example 109, except that 1-hexylamine was used instead of methylamine hydrochloride.

$^1$H NMR (600 MHz, DMSO) δ 3.24 (q, J=6.6 Hz, 2H), 1.52 (m, 2H), 1.31 (m, 6H), 0.85 (t, J=6.6 Hz, 3H)

LCMS: 186.2 [M+H]$^+$

Example 110: Synthesis of N1-(4-chloro)phenyl Biguanide Hydrochloride

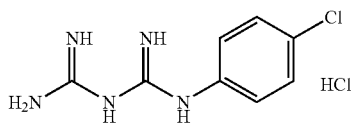

The target compound was obtained as a white solid (0.75 g, 30.0%) in the same manner as in Example 109, except that 4-chloroaniline was used instead of methylamine hydrochloride.

$^1$H NMR (600 MHz, DMSO) δ 7.42 (d, J=8.4 Hz, 2H), 7.30 (d, J=8.4 Hz, 2H)

LCMS: 212.0 [M+H]$^+$

Example 111: Synthesis of N1-(2-prophene) Biguanide Hydrochloride

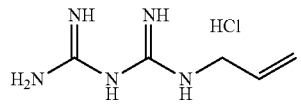

The target compound was obtained as a white solid (0.52 g, 24.0%) in the same manner as in Example 109, except that 2-propenamine was used instead of methylamine hydrochloride.

$^1$H NMR (600 MHz, DMSO) δ 5.75 (m, 1H), 517 (d, J=168 Hz, 2H), 3.70 (m, 2H)

LCMS: 142.2 [M+H]$^+$

Example 112: Synthesis of N1-(benzo[d][1,3]di-oxol-5-yl)methyl Biguanide Hydrochloride

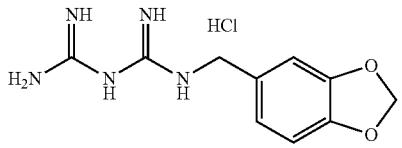 [SMILES: N=C(N)NC(=N)NCc1ccc2c(c1)OCO2 ; Cl]

The target compound was obtained as a white solid (0.90 g, 18.4%) in the same manner as in Example 109, except that (benzo[d][1,3]dioxol-5-yl)methanamine was used instead of methylamine hydrochloride.
¹H NMR (600 MHz, DMSO) δ 7.00 (s, 1H), 6.68 (s, 2H), 5.97 (s, 2H), 4.36 (s, 2H)
LCMS: 236.0 [M+H]⁺

Example 113: Synthesis of N1-phenyl Biguanide Hydrochloride

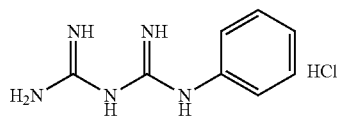 [SMILES: N=C(N)NC(=N)Nc1ccccc1 ; Cl]

The target compound was obtained as a white solid (1.51 g, 71.4%) in the same manner as in Example 109, except that aniline was used instead of methylamine hydrochloride.
¹H NMR (600 MHz, DMSO) δ 7.33 (min, 2H), 7.25 (m, 2H), 6.99 (m, 1H)
LCMS: 178.2 [M+H]⁺

Example 114: Synthesis of N1-propyl Biguanide Hydrochloride

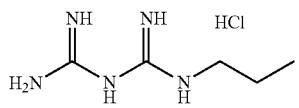

The target compound was obtained as a white solid (1.91 g, 53.3%) in the same manner as in Example 109, except that 1-propylamine was used instead of methylamine hydrochloride.
¹H NMR (600 MHz, DMSO) δ 3.01 (m, 2H), 1.43 (m, 2H), 0.84 (m, 3H)
LCMS: 144.3 [M+H]⁺

Example 115: Synthesis of N1,N1-diisopropyl Biguanide Hydrochloride

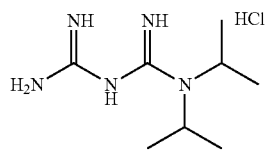

The target compound was obtained as a white solid (1.62 g, 36.6%) in the same manner as in Example 109, except that N,N-diisopropylamine was used instead of methylamine hydrochloride.
¹H NMR (600 MHz, DMSO) δ 3.27 (m, 2H), 1.19 (m, 12H)
LCMS: 186.2 [M+H]⁺

Example 116: Synthesis of N1-(4-bromo)phenyl Biguanide Hydrochloride

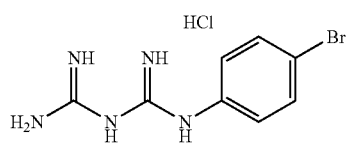 [SMILES: Cl ; N=C(N)NC(=N)Nc1ccc(Br)cc1]

The target compound was obtained as a white solid (1.91 g, 74.6%) in the same manner as in Example 109, except that 4-bromoaniline was used instead of methylamine hydrochloride.
¹H NMR (600 MHz, DMSO) δ 7.45 (m, 2H), 7.35 (nm, 2H)
LCMS: 257.1 [M+H]⁺

Example 117: Synthesis of N1-(4-acetyl)phenyl Biguanide Hydrochloride

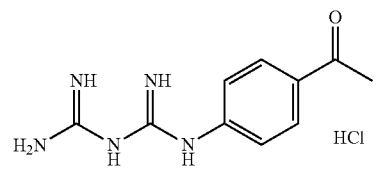 [SMILES: CC(=O)c1ccc(NC(=N)NC(=N)N)cc1 ; Cl]

The target compound was obtained as a white solid (0.61 g, 27.8%) in the same manner as in Example 109, except that 4-acetylaniline was used instead of methylamine hydrochloride.
¹H NMR (600 MHz, DMSO) δ 7.88 (d, J=8.4 Hz, 2H), 7.52 (d, J=8.4 Hz, 2H), 2.50 (s, 3H)
LCMS: 220.2 [M+H]⁺

Example 118: Synthesis of N1-morpholin-4-yl Biguanide Hydrochloride

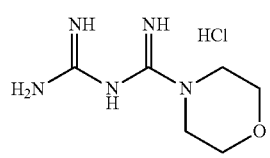

The target compound was obtained as a white solid (1.36 g, 79.5%) in the same manner as in Example 109, except that morpholin-4-yl was used instead of methylamine hydrochloride.
¹H NMR (600 MHz, DMSO) δ 3.58 (m, 4H), 3.43 (m, 4H)
LCMS: 172.1 [M+H]⁺

Example 119: Synthesis of N1-(2-trifluoromethyl)phenyl Biguanide Hydrochloride

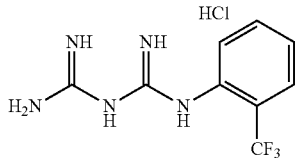

The target compound was obtained as a white solid (0.05 g, 2.0%) in the same manner as in Example 109, except that 2-trifluoromethylaniline was used instead of methylamine hydrochloride.

$^1$H NMR (400 MHz, DMSO) δ 8.17 (s, 1H), 8.03 (d, J=8 Hz, 1H), 7.53 (1, J=8 Hz, 2H), 79 (d, J=8 Hz, 1H)

LCMS: 246.0 [M+H]$^+$

Example 120: Synthesis of N1-(4-methoxy)phenyl Biguanide Hydrochloride

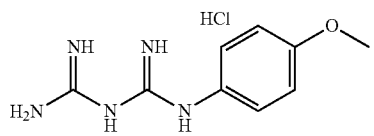

The target compound was obtained as a white solid (1.85 g, 89.3%) in the same manner as in Example 109, except that 4-methoxyaniline was used instead of methylamine hydrochloride.

$^1$H NMR (600 MHz, DMSO) δ 7.23 (d, J=7.2 Hz, 2H), 6.87 (d, J=7.2 Hz, 2H), 3.70 (s, 3H)

LCMS: 208.1 [M+H]$^+$

Example 121: Synthesis of N1-(2-propyl)phenyl Biguanide Hydrochloride

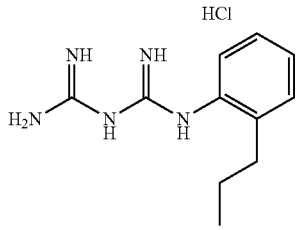 [SMILES: Cl ; CCCc1ccccc1NC(=N)NC(=N)N]

The target compound was obtained as a white solid (0.75 g, 25.0%) in the same manner as in Example 109, except that 2-propylaniline was used instead of methylamine hydrochloride.

$^1$H NMR (600 MHz, DMSO) δ 7.16 (m, 4H), 2.59 (m, 2H), 1.55 (m, 2H), 0.93 (m, 3H)

LCMS: 220.2 [M+H]$^+$

Example 122: Synthesis of N1-(4-morpholin-4-yl)phenyl Biguanide Hydrochloride

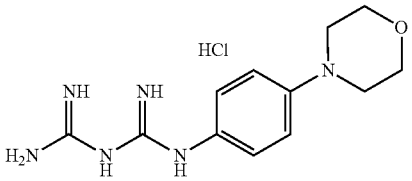 [SMILES: N=C(N)NC(=N)Nc1ccc(N2CCOCC2)cc1 ; Cl]

The target compound was obtained as a white solid (0.96 g, 36.6%) in the same manner as in Example 109, except that 4-morpholin-4-ylaniline was used instead of methylamine hydrochloride.

$^1$H NMR (600 MHz, DMSO) δ 7.18 (d, J=8.4 Hz, 2H), 6.88 (d, J=8.4 Hz), 3.71 (m, 4H), 3.03 (m, 4H)

LCMS: 263.1 [M+H]$^+$

Example 123: Synthesis of N1-piperidine Biguanide Hydrochloride

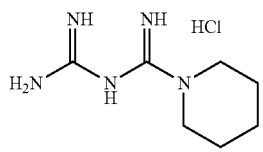 [SMILES: N=C(N)NC(=N)N1CCCCC1 ; Cl]

The target compound was obtained as a white solid (0.20 g, 8.0%) in the same manner as in Example 109, except that piperidine was used instead of methylamine hydrochloride.

$^1$H NMR (600 MHz, DMSO) δ 3.42 (m, 4H), 1.57 (m, 2H), 1.49 (m, 4H)

LCMS: 170.2 [M+H]$^+$

Example 124: Synthesis of N1-benzyl Biguanide Hydrochloride

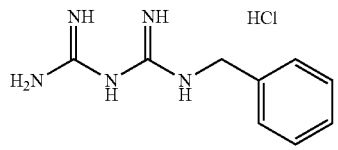 [SMILES: N=C(N)NC(=N)NCc1ccccc1 ; Cl]

The target compound was obtained as a white solid (0.70 g, 20.0%) in the same manner as in Example 109, except that benzylamine was used instead of methylamine hydrochloride.

$^1$H NMR (600 MHz, DMSO) δ 7.33 (m, 5H), 4.35 (d, J=6 Hz, 2H)

LCMS: 192.3 [M+H]$^+$

Example 125: Synthesis of N1-4-(N-acetylamino)phenyl Biguanide Hydrochloride

The target compound was obtained as a white solid (1.97 g, 61.0%) in the same manner as in Example 109, except that 4-(N-acetylamino)aniline was used instead of methylamine hydrochloride.

$^1$H NMR (600 MHz, DMSO) δ 7.46 (m, 2H), 6.97 (m, 2H), 1.97 (s, 3H)

LCMS: 235.0 [M+H]$^+$

Example 126: Synthesis of N1-pyrrolidine Biguanide Hydrochloride

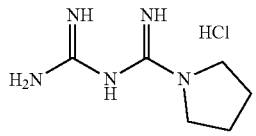

The target compound was obtained as a white solid (0.42 g, 27.0%) in the same manner as in Example 109, except that pyrrolidine was used instead of methylamine hydrochloride.

$^1$H NMR (600 MHz, DMSO) δ 3.31 (m, 4H), 1.87 (m, 4H)

LCMS: 156.2 [M+H]$^+$

Example 127: Synthesis of N1-4-(pyridin-2-yl)piperazine Biguanide Hydrochloride

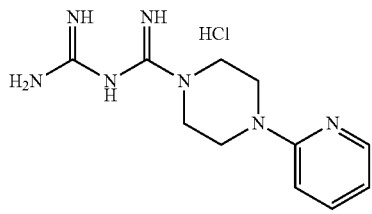 [SMILES: N=C(N)NC(=N)N1CCN(c2ccccn2)CC1 ; Cl]

The target compound was obtained as a white solid (1.74 g, 51.0%) in the same manner as in Example 109, except that 1-(pyridin-2-yl)piperazine was used instead of methylamine hydrochloride.

$^1$H NMR (600 MHz, D$_2$O) δ 7.95 (d, J=7.8 Hz, 1H), 7.55 (t, J=7.8 Hz, 1H), 6.76 (d, J==7.8 Hz, 1H), 6.69 (t, J=7.8 Hz, 1H), 3.54 (m, 4H), 3.43 (m, 4H)

LCMS: 248.3 [M+H]$^+$

Example 128: Synthesis of N1-(4-trifluoromethyl)phenyl Biguanide Hydrochloride

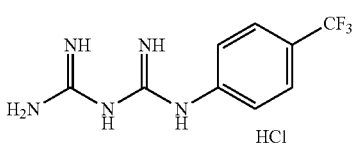 [SMILES: N=C(N)NC(=N)Nc1ccc(C(F)(F)F)cc1 ; Cl]

The target compound was obtained as a white solid (1.27 g, 38.0%) in the same manner as in Example 109, except that 4-trifluoromethylaniline was used instead of methylamine hydrochloride.

$^1$H NMR (600 MHz, DMSO) δ 7.60 (q, J==8.4 Hz, 4H)

LCMS: 246.0 [M+H]$^+$

Example 129: Synthesis of N1-(4-chloro)benzyl Biguanide Hydrochloride

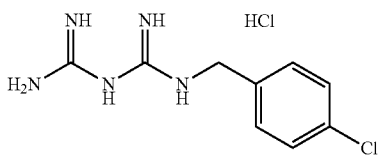 [SMILES: N=C(N)NC(=N)NCc1ccc(Cl)cc1 ; Cl]

The target compound was obtained as a white solid (0.39 g, 12.0%) in the same manner as in Example 109, except that 4-chlorobenzylamine was used instead of methylamine hydrochloride.

$^1$H NMR (600 MHz, DMSO) δ 7.41 (q, J=7.8 Hz, 4H), 4.36 (d, J=48 Hz, 2H)

LCMS: 226.0 [M+H]$^+$

Example 130: Synthesis of N1,N1-dibenzyl Biguanide Hydrochloride

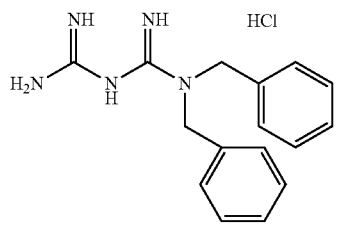 [SMILES: N=C(N)NC(=N)N(Cc1ccccc1)Cc1ccccc1 ; Cl]

The target compound was obtained as a white solid (0.17 g, 4.0%) in the same manner as in Example 109, except that N,N-dibenzylamine was used instead of methylamine hydrochloride.

$^1$H NMR (600 MHz, DMSO) δ 7.35 (t, J=7.8 Hz, 4H), 7.30 (d, J=7.8 Hz, 2H), 7.26 (d, J=7.8 Hz, 4H), 4.54 (s, 4H)

LCMS: 282.3 [M+H]$^+$

Example 131: Synthesis of N1-(4-methoxy)benzyl Biguanide Hydrochloride

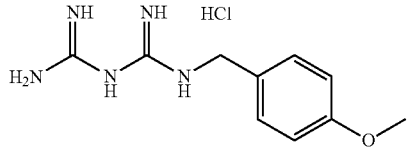 [SMILES: COc1ccc(CNC(=N)NC(=N)N)cc1 ; Cl]

The target compound was obtained as a white solid (0.28 g, 9.0%) in the same manner as in Example 109, except that 4-methoxybenzylamine was used instead of methylamine hydrochloride.

$^1$H NMR (600 MHz. DMSO) δ 7.24 (d, J=7.8 Hz, 2H), 6.90 (d, J=7.8 Hz, 2H), 4.29 (d, J=6 Hz, 2H)

LCMS: 220.0 [M+H]$^+$

Example 132: Synthesis of N1-(4-fluoro)benzyl Biguanide Hydrochloride

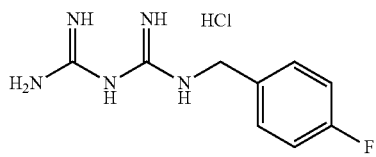

The target compound was obtained as a white solid (0.17 g, 6.0%) in the same manner as in Example 109, except that 4-fluorobenzylamine was used instead of methylamine hydrochloride.

$^1$H NMR (600 MHz, DMSO) δ 7.36 (m, 2H), 7.17 (m, 2H), 4.32 (d, J=6 Hz, 2H)

LCMS: 210.0 [M+H]$^+$

Example 133: Synthesis of N1,N1-dihexyl Biguanide Hydrochloride

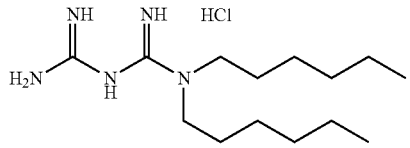 [SMILES: CCCCCCN(CCCCCC)C(=N)NC(=N)N ; Cl]

The target compound was obtained as a white solid (0.73 g, 30.0%) in the same manner as in Example 109, except that N,N-dihexylamine was used instead of methylamine hydrochloride.

$^1$H NMR (600 MHz, DMSO) δ 2.82 (t, J=7.8 Hz, 4H), 1.58 (m, 4H), 1.29 (min, 12H), 0.86 (t, J=7.8 Hz, 6H)

LCMS: 270.2 [M+H]$^+$

Example 134: Synthesis of N1-methyl-N1-butyl Biguanide Hydrochloride

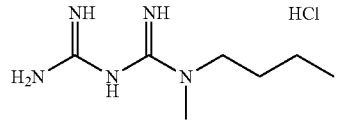

The target compound was obtained as a white solid (0.71 g, 34.3%) in the same manner as in Example 109, except that N-methyl-N-butylamine was used instead of methylamine hydrochloride.

$^1$H NMR (600 MHz, DMSO) δ 3.27 (t, J=7.2 Hz, 2H), 2.86 (s, 3H), 1.43 (m, 2H), 1.22 (m, 2H), 0.84 (t, J=7.2 Hz, 3H)

LCMS: 172.1 [M+H]$^+$

Example 135: Synthesis of N1-methyl-N1-cyclohexyl Biguanide Hydrochloride

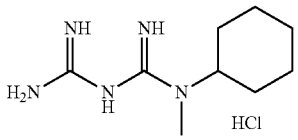

The target compound was obtained as a white solid (0.08 g, 5.0%) in the same manner as in Example 109, except that N-methyl-N-cyclohexylamine was used instead of methylamine hydrochloride.

$^1$H NMR (600 MHz, DMSO) δ 2.46 (m, 1H), 1.70 (m, 2H), 1.53 (m, 3H), 1.42 (m, 2H), 1.22 (m, 2H), 1.04 (m, 1H)

LCMS: 198.1 [M+H]$^+$

Example 136: Synthesis of N1,N1-dicyclohexyl Biguanide Hydrochloride

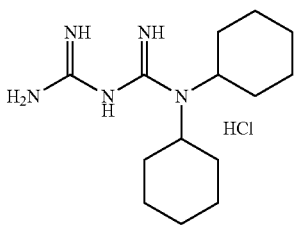 [SMILES: N=C(N)NC(=N)N(C1CCCCC1)C1CCCCC1 ; Cl]

The target compound was obtained as a white solid (2.32 g, 70.0%) in the same manner as in Example 109, except that N,N-dicyclohexylamine was used instead of methylamine hydrochloride.

$^1$H NMR (600 MHz, DMSO) δ 3.03 (m, 2H), 1.96 (m, 4H), 1.71 (m, 4H), 1.57 (m, 2H), 1.26 (m, 8H) 1.05 (m, 2H)

LCMS: 266.1 [M+H]$^+$

Example 137: Synthesis of N1-(4-chloro)phenethyl Biguanide Hydrochloride

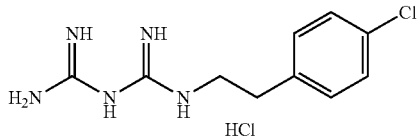 [SMILES: N=C(N)NC(=N)NCCc1ccc(Cl)cc1 ; Cl]

The target compound was obtained as a white solid (0.37 g, 13.0%) in the same manner as in Example 109, except that 4-chlorophenethylamine was used instead of methylamine hydrochloride.

$^1$H NMR (600 MHz, DMSO) δ 7.37 (s, 4H), 3.47 (s, 2H), 2.85 (s, 2H)

LCMS: 240.1 [M+H]$^+$

Example 138: Synthesis of N1-(4-hydroxy)phenethyl Biguanide Hydrochloride

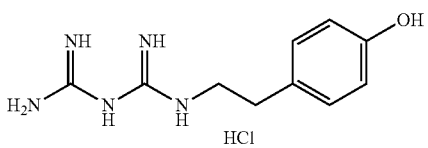 [SMILES: N=C(N)NC(=N)NCCc1ccc(O)cc1 ; Cl]

The target compound was obtained as a white solid (0.15 g, 10.0%) in the same manner as in Example 109, except that 4-hydroxyphenethylamine was used instead of methylamine hydrochloride.

$^1$H NMR (600 MHz, DMSO) δ 7.07 (d, J=8.4 Hz, 2H), 6.71 (d, J=8.4 Hz, 2H), 3.38 (s, 2H), 2.72 (s, 2H)

LCMS: 222.2 [M+H]$^+$

Example 139: Synthesis of N1-azepane Biguanide Hydrochloride

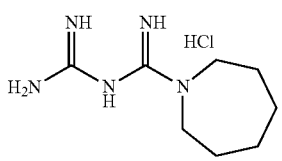 [SMILES: N=C(N)NC(=N)N1CCCCCC1 ; Cl]

The target compound was obtained as a white solid (0.18 g, 8.0%) in the same manner as in Example 109, except that azepane was used instead of methylamine hydrochloride.

$^1$H NMR (400 MHz, DMSO) δ 3.44 (min, 4H), 1.64 (m, 4H), 1.49 (min, 4H)

LCMS: 184.2 [M+H]$^+$

Example 140: Synthesis of N1-(4-trifluoro ethoxy)phenyl Biguanide Hydrochloride

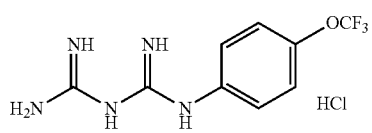 [SMILES: N=C(N)NC(=N)Nc1ccc(OC(F)(F)F)cc1 ; Cl]

The target compound was obtained as a white solid (0.06 g, 15.0%) in the same manner as in Example 109, except that 4-trifluoromethoxyaniline was used instead of methylamine hydrochloride.

$^1$H NMR (600 MHz, DMSO) δ 7.46 (d, J=8.4 Hz, 2H), 7.31 (d, J=8.4 Hz, 2H)

LCMS: 262.1 [M+H]$^+$

Example 141: Synthesis of N1-(4-trifluoromethyl)benzyl Biguanide Hydrochloride

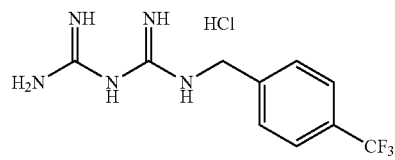 [SMILES: N=C(N)NC(=N)NCc1ccc(C(F)(F)F)cc1 ; Cl]

The target compound was obtained as a white solid (0.02 g, 6.0%) in the same manner as in Example 109, except that 4-trifluoromethylaniline was used instead of methylamine hydrochloride.

$^1$H NMR (600 MHz, DMSO) δ 7.71 (d, J=8.4 Hz, 2H), 7.52 (d, J=8.4 Hz, 2H), 4.49 (s, 2H)

LCMS: 260.0 [M+H]$^+$

Example 142: Synthesis of N1-(4-trifluoromethoxy)benzyl Biguanide Hydrochloride

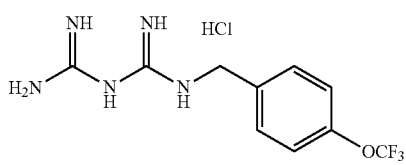

The target compound was obtained as a white solid (0.01 g, 6.0%) in the same manner as in Example 109, except that 4-trifluoromethoxybenzylamine was used instead of methylamine hydrochloride.

$^1$H NMR (600 MHz, DMSO) δ 7.51 (d, J=8.4 Hz, 2H), 7.32 (d, J=8.4 Hz, 2H), 4.39 (s, 2H)

LCMS: 276.1 [M+H]$^+$

Example 143: Synthesis of N1-2-(benzo[d][1,3]dioxol-5-yl)ethyl Biguanide Hydrochloride

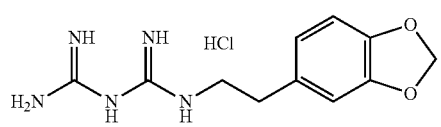 [SMILES: N=C(N)NC(=N)NCCc1ccc2c(c1)OCO2 ; Cl]

The target compound was obtained as a white solid (0.03 g, 40.0%) in the same manner as in Example 109, except that 2-(benzo[d][1,3]dioxol-5-yl)ethanamine was used instead of methylamine hydrochloride.

$^1$H NMR (600 Hz, CD$_3$OD) δ 6.78 (m, 3H), 5.93 (s, 2H), 3.13 (t, 2H), 2.87 (t, 2H)

LCMS: 250.1 [M+H]$^+$

Example 144: Synthesis of N1-(furan-2-yl)methyl Biguanide Hydrochloride

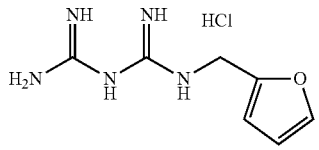 [SMILES: N=C(N)NC(=N)NCc1ccco1 ; Cl]

The target compound was obtained as a white solid (7.70 g, 22.0%) in the same manner as in Example 109, except that furan-2-ylmethanamine was used instead of methylamine hydrochloride.

$^1$H NMR (600 MHz, DMSO-d$_6$) δ7.87 (m, 1H), 7.55 (s, 1H), 7.15 (m, 4H), 6.35 (m, 1H), 4.32 (s, 2H)

LCMS: 182.0 [M+H]$^+$

Example 145: Synthesis of N1-(2-thiophen-2-yl)ethyl Biguanide Hydrochloride

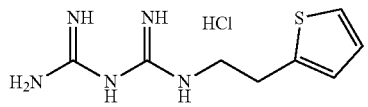 [SMILES: N=C(N)NC(=N)NCCc1cccs1 ; Cl]

The target compound was obtained as a white solid (10.21 g, 35.00%) in the same manner as in Example 109, except that thiophenethylamine was used instead of methylamine hydrochloride.

$^1$H NMR (600 MHz, DMSO-d$_6$) δ9.73 (s, 1H), 9.28 (s, 2H), 8.62 (s, 3H), 7.34 (m, 1H), 6.94 (m, 1H), 6.92 (m, 1H), 3.52 (s, 2H), 3.08 (s, 2H)

LCMS: 212.0 [M+H]$^+$

Example 146: Synthesis of N1-(2-fluoro-4-hydroxy)benzyl Biguanide Hydrochloride

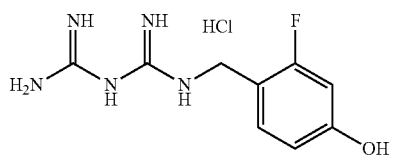 [SMILES: N=C(N)NC(=N)NCc1ccc(O)cc1F ; Cl]

The target compound was obtained as a white solid (0.01 g, 12.2%) in the same manner as in Example 109, except that 2-fluoro-4-hydroxybenzylamine was used instead of methylamine hydrochloride.

$^1$H NMR (600 MHz, CD$_3$OD) δ7.19 (m, 1H), 6.58 (m, 1H), 6.50 (m, 1H), 4.34 (s, 2H)

LCMS: 226.1 [M+H]$^+$

Example 147: Synthesis of N1-(4-fluoro)phenylpropyl Biguanide Hydrochloride

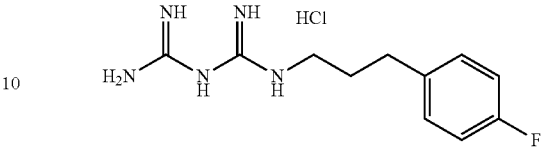

The target compound was obtained as a white solid (0.01 g, 22.0%) in the same manner as in Example 109, except that 3-(4-fluorophenyl)propan-1-amine was used instead of methylamine hydrochloride.

$^1$H NMR (600 MHz, CD$_3$OD) δ 7.23 (m, 2H), 7.01 (m, 2H), 3.18 (t, 2H), 2.68 (t, 2H), 1.88 (q, 21H)

LCMS: 238.2 [M+H]$^+$

Example 148: Synthesis of N1-(4-methoxy)phenylpropyl Biguanide Hydrochloride

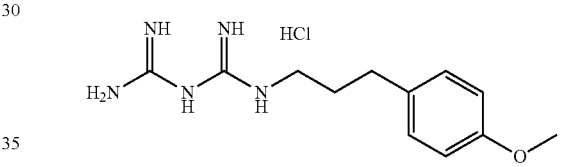

The target compound was obtained as a white solid (0.09 g, 10.0%) in the same manner as in Example 109, except that 3-(4-methoxyphenyl)propan-1-amine was used instead of methyl amine hydrochloride.

$^1$H NMR (600 MHz, CD$_3$OD) δ7.14 (d, 2H), 6.85 (d, 2H), 3.18 (s, 2H), 2.57 (s, 2H), 2.50 (s, 3H), 1.98 (s, 2H)

LCMS: 250.1 [M+H]$^+$

Example 149: Synthesis of N1-(2-iodo)benzyl Biguanide Hydrochloride

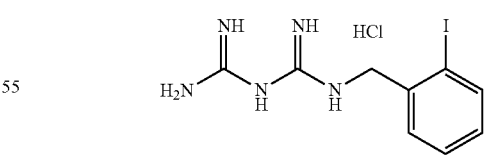

The target compound was obtained as a white solid (0.10 g, 33.0%) in the same manner as in Example 109, except that 2-iodobenzylamine was used instead of methylamine hydrochloride.

$^1$H NMR (600 MHz, CD$_3$OD) δ7.88 (m, 1H), 7.43 (s, 1H), 7.40 (s, 1H), 7.06 (s, 1H), 4.33 (s, 2H)

LCMS: 318.0 [M+H]$^+$

Example 150: Synthesis of N1-(3-iodo)benzyl Biguanide Hydrochloride

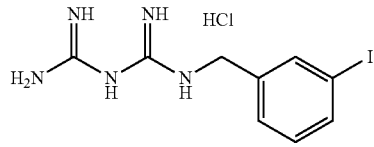 [SMILES: N=C(N)NC(=N)NCc1cccc(I)c1 ; Cl]

The target compound was obtained as a white solid (0.11 g, 25.5%) in the same manner as in Example 109, except that 3-iodobenzylamine was used instead of methylamine hydrochloride.

$^1$H NMR (600 MHz, CD$_3$OD) δ7.78 (s, 1H), 7.67 (s, 1H), 7.19 (s, 1H), 7.18 (s, 1H), 4.45 (s, 2H)
LCMS: 318.0 [M+H]$^+$

Example 151: Synthesis of N-(6,6-dimethyl-4-oxo-1,4,5,6-tetrahydropyrimidin-2-yl)piperidin-1-carboximidamide Hydrochloride

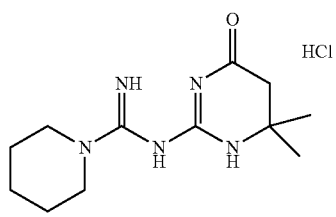 [SMILES: CC1(C)CC(=O)N=C(NC(=N)N2CCCCC2)N1 ; Cl]

Ethyl-3-amino-3-methylbutanoate hydrochloride (0.20 g, 1.12 mmol) was dissolved in ethanol (20 mL) at room temperature. Piperidine cyanoguanidine (0.17 g, 1.12 mmol) was added thereto and stirred under reflux for 15 hours. The reaction mixture was concentrated under reduced pressure, and separated and purified using a chromatography in a condition where the ratio of methylene chloride to methyl alcohol was 9:1 and the target compound was obtained as a white solid (0.32 g, 100%).

$^1$H NMR (600 MHz, CD$_3$OD) δ 3.16 (m, 4H), 2.51 (m, 2H), 1.58 (m, 6H), 1.29 (s, 6H)
LCMS: 252.2 [M+H]$^+$

Example 152: Synthesis of 1-(6,6-dimethyl-4-oxo-1,4,5,6-tetrahydropyrimidin-3-yl)guanidine Hydrochloride

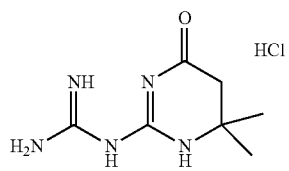

The target compound was obtained as a white solid (0.02 g, 11.0%) in the same manner as in Example 151, except that cyanoguanidine was used instead of piperidine cyanoguanidine.

$^1$H NMR (600 MHz, CD$_3$OD) δ2.51 (m, 2H), 1.29 (s, 6H)
LCMS: 184.2 [M+H]$^+$

Example 153: Synthesis of N-(1,4,5,6-tetrahydropyrimidin-2-yl)piperidin-1-carboximidamide Hydrochloride

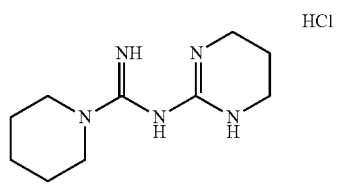 [SMILES: Cl ; N=C(NC1=NCCCN1)N1CCCCC1]

The target compound was obtained as a white solid (0.01 g, 6.0%) in the same manner as in Example 151, except that piperidine-1-carbamimidoyl cyanide and propan-1,3-diamine were used instead of piperidine cyanoguanidine and ethyl-3-amino-3-methylbutanoate hydrochloride.

$^1$H NMR (600 MHz, CD$_3$OD) δ3.15 (m, 4H), 3.04 (m, 4H), 1.73 (m, 4H), 1.64 (m, 4H)
LCMS: 210.2 [M+H]$^+$

Example 154: Synthesis of N-(6-methyl-4-oxo-1,4,5-tetrahydropyrimidin-2-yl)piperidin-1-carboximidamide Hydrochloride

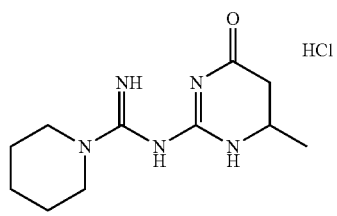 [SMILES: CC1CC(=O)N=C(NC(=N)N2CCCCC2)N1 ; Cl]

The target compound was obtained as a white solid (0.01 g, 5.0%) in the same manner as in Example 151, except that ethyl-3-anminobutanoate hydrochloride was used instead of ethyl-3-amino-3-methylbutanoate hydrochloride.

$^1$H NMR (600 MHz, CD$_3$OD) δ3.14 (min, 4H), 3.00 (m, 1H), 2.51 (m, 2H), 1.58 (m, 6H), 1.29 (s, 3H)
LCMS: 238.1 [M+H]$^+$

Example 155: Synthesis of N-(5-methyl-4-oxo-1,4,5,6-tetrahydropyrimidin-2-yl)piperidin-1-carboximidamide Hydrochloride

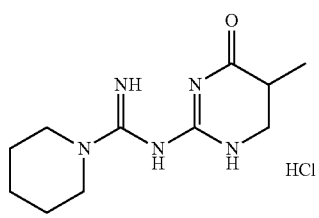 [SMILES: CC1CNC(NC(=N)N2CCCCC2)=NC1=O ; Cl]

The target compound was obtained as a white solid (0.01 g, 5.0%) in the same manner as in Example 151, except that ethyl-3-amino-2-methylbutanoate hydrochloride was used instead of ethyl-3-amino-3-methylbutanoate hydrochloride.

¹H NMR (600 MHz, CD₃OD) δ3.13 (m, 4H), 3.01 (m, 2H), 2.50 (m, 1H), 1.58 (m, 6H), 1.29 (s, 3H)
LCMS: 238.1 [M+H]⁺

Example 156: Synthesis of N-(4-oxo-1,4,5,6-tetra-hydropyrimidin-2-yl)piperidin-1-carboximidamide Hydrochloride

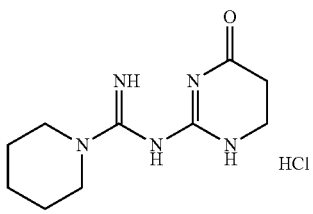 [SMILES: N=C(NC1=NC(=O)CCN1)N1CCCCC1 ; Cl]

The target compound was obtained as a white solid (0.04 g, 10.0%) in the same manner as in Example 151, except that ethyl-3-aminopropanoate hydrochloride was used instead of ethyl-3-amino-3-methylbutanoate hydrochloride.
¹H NMR (600 MHz, CD₃OD) δ3.15 (m, 4H), 3.03 (m, 2H), 2.52 (m, 2H), 1.58 (m, 6H)
LCMS: 224.2 [M+H]⁺

Example 157: Synthesis of N-(6-cyclopropyl-4-oxo-1,4,5,6-tetrahydropyrimidin-2-yl)piperidin-1-carboximidamide Hydrochloride

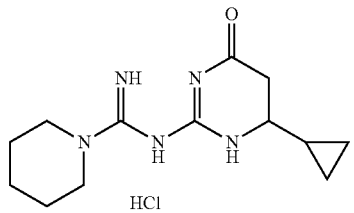 [SMILES: N=C(NC1=NC(=O)CC(C2CC2)N1)N1CCCCC1 ; Cl]

The target compound was obtained as a white solid (0.12 g, 8.0%) in the same manner as in Example 151, except that ethyl-3-amino-3-cyclopropylpropanoate hydrochloride was used instead of ethyl-3-amino-3-methylbutanoate hydrochloride.
¹H NMR (600 MHz, DMSO) δ 3.73 (m, 1H), 3.48 (m, 4H), 2.76 (min, 1H), 2.43 (m, 1H), 1.68 (m, 6H), 1.52 (m, 1H), 0.90 (nm, 4H)
LCMS: 264.2 [M+H]⁺

Example 158: Synthesis of N-(5-methyl-1,4,5,6-tetrahydropyrimidin-2-yl)piperidin-1-carboximidamide Hydrochloride

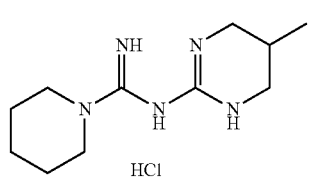 [SMILES: CC1CN=C(NC(=N)N2CCCCC2)NC1 ; Cl]

The target compound was obtained as a white solid (0.01 g, 3.0) in the same manner as in Example 151, except that piperidine-1-carbamimidoyl cyanide and 2-methylpropan-1,3-diamine were used instead of piperidine cyanoguanidine and ethyl-3-amino-3-methylbutanoate hydrochloride.
¹H NMR (600 MHz, CD₃OD) δ 3.49 (m, 81H), 167 (m, 6H), 1.59 (m, 1H), 0.98 (m, 3H)
LCMS: 224.2 [M+H]⁺

Example 159: Synthesis of N-(6-isopropyl-4-oxo-1,4,5,6-tetrahydropyrimidin-2-yl)piperidin-1-carboximidamide Hydrochloride

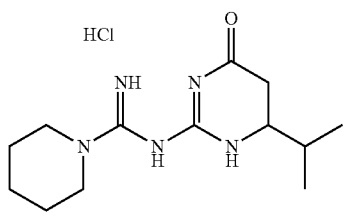 [SMILES: CC(C)C1CC(=O)N=C(NC(=N)N2CCCCC2)N1 ; Cl]

The target compound was obtained as a white solid (0.02 g, 3.0%) in the same manner as in Example 151, except that ethyl-3-amino-4-methylpentanoate hydrochloride was used instead of ethyl-3-amino-3-methylbutanoate hydrochloride.
¹H NMR (600 MHz, CD₃OD) δ 3.72 (m, 1H), 3.49 (m, 4H), 2.74 (m, 1H), 2.41 (m, 1H), 1.67 (m, 6H), 1.53 (m, 1H), 0.92 (m, 6H)
LCMS: 266.2 [M+H]⁺

Example 160: Synthesis of 1-(5-methyl-4-oxo-1,4,6-tetrahydropyrimidin-3-yl)guanidine Hydrochloride

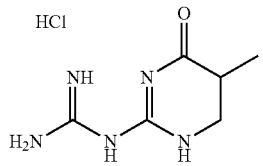

The target compound was obtained as a white solid (0.02 g, 4.0%) in the same manner as in Example 151, except that cyanoguanidine and ethyl-3-amino-2-methylbutanoate hydrochloride were used instead of piperidine cyanoguanidine and ethyl-3-amino-3-methylbutanoate hydrochloride.
¹H NMR (600 MHz, CD₃OD) δ3.02 (m, 2H), 2.52 (m, 1H), 1.29 (s, 3H)
LCMS: 170.2 [M+H]⁺

Example 161: Synthesis of N-(6-isobutyl-4-oxo-1,4,5,6-tetrahydropyrimidin-2-yl)piperidin-1-carboximidamide Hydrochloride

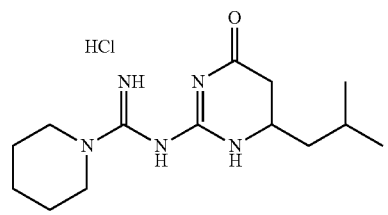 [SMILES: CC(C)CC1CC(=O)N=C(NC(=N)N2CCCCC2)N1 ; Cl]

The target compound was obtained as a white solid (0.10 g, 8.0%) in the same manner as in Example 151, except that ethyl-3-amino-5-methylhexanoate hydrochloride was used instead of ethyl-3-amino-3-methylbutanoate hydrochloride.

$^1$H NMR (600 MHz, CD$_3$OD) δ3.72 (m, 1H), 3.49 (m, 4H), 2.74 (m, 1H), 2.41 (m, 1H), 1.67 (m, 7H), 1.53 (m, H), 1.35 (m, 1H), 0.92 (m, 6H)

LCMS: 266.2 [M+H]$^+$

Example 162: Synthesis of N-(4-methyl-1,4,5,6-tetrahydropyrimidin-2-yl)piperidin-1-carboximidamide Hydrochloride

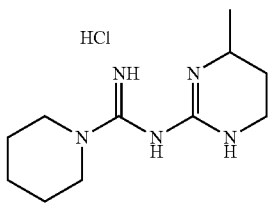 [SMILES: CC1CCNC(NC(=N)N2CCCCC2)=N1 ; Cl]

The target compound was obtained as a white solid (0.01 g, 2.0%) in the same manner as in Example 151, except that piperidine-1-carbamimidoyl cyanide and butan-1,3-diamine were used instead of piperidine cyanoguanidine and ethyl-3-amino-3-methylbutanoate hydrochloride.

$^1$H NMR (600 MHz, DMSO) δ 3.43 (m, 7H), 1.65 (m, 6H), 1.56 (ml 2H), 0.99 (m, 3H)

LCMS: 224.1 [M+H]$^+$

Example 163: Synthesis of N-(6-propyl-4-oxo-1,4,5,6-tetrahydropyrimidin-2-yl)piperidin-1-carboximidamide Hydrochloride

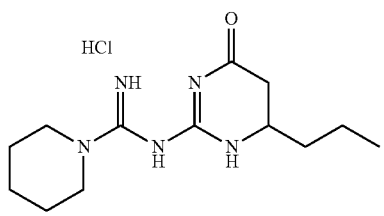 [SMILES: CCCC1CC(=O)N=C(NC(=N)N2CCCCC2)N1 ; Cl]

The target compound was obtained as a white solid (0.01 g, 2.0%) in the same manner as in Example 151, except that ethyl-3-aminohexanoate hydrochloride was used instead of ethyl-3-amino-3-methylbutan oate hydrochloride.

$^1$H NMR (600 MHz, CD$_3$OD) δ3.73 (m, 1H), 3.50 (m, 4H), 2.72 (m, 1H), 2.40 (m, 1H), 1.68 (m, 8H), 1.50 (m, 1H), 1.33 (m, 1H), 0.95 (m, 3H)

LCMS: 266.2 [M+H]$^+$

Example 164: Synthesis of 1-(6-methyl-4-oxo-1,4,5,6-tetrahydropyrimidin-3-yl)guanidine Hydrochloride

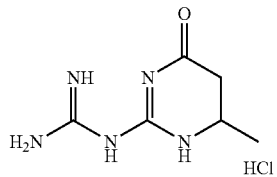

The target compound was obtained as a white solid (0.02 g, 4.0%) in the same manner as in Example 151, except that cyanoguanidine and ethyl-3-aminobutanoate hydrochloride were used instead of piperidine cyanoguanidine and ethyl-3-amino-3-methylbutanoate hydrochloride.

$^1$H NMR (600 MHz, CD$_3$OD) δ 3.00 (m, 11H), 2.51 (m, 2H), 1.29 (s, 3H)

LCMS: 170.1 [M+H]$^+$

Example 165: Synthesis of N-(4-ethyl-1,4,5,6-tetrahydropyrimidin-2-)piperidin-1-carboximidamide Hydrochloride

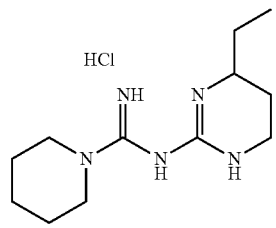 [SMILES: CCC1CCNC(NC(=N)N2CCCCC2)=N1 ; Cl]

The target compound was obtained as a white solid (0.01 g, 5.0%) in the same manner as in Example 151, except that pentan-3,5-diamine was used instead of ethyl-3-amino-3-methylbutanoate hydrochloride.

$^1$H NMR (600 MHz, CD$_3$OD) δ3.45 (m, 7H), 1.66 (m, 6H), 1.58 (m, 2H), 1.36 (m, 2H), 0.99 (m, 3H)

LCMS: 238.2 [M+H]$^+$

TEST EXAMPLES

The compounds synthesized by the methods described in Examples were evaluated with respect to the effect of inhibiting proliferation of cancer cells according to the methods described in Test Examples below.

Test Example 1: Measurement of Inhibitory Effect Against Cancer Cell Proliferation HCT116 cells (purchased from Korean Cell Line Bank (KCLB)) derived from human colorectal cancer were used, and the effect of a biguanide derivative on the inhibition of cancer cell proliferation was confirmed by measuring the value of a concentration (cell growth inhibition concentration, IC$_{50}$) at which 50% of the cell growth was inhibited using a 3-(4,5-dimethylthiazol-2-yl)-2,5-diphenytetrazolium bromide (MTT) reagent.

HCT116 cells were placed in a 96-well plate and cultured in RPMI-1640 medium containing 10% calf serum for 16 hours until each well had a cell count of about 5000. Then, to obtain the $IC_{50}$ value of each compound, the 100 mM PBS stock compound was treated to the cell culture at concentrations of 10 mM, 1 mM, 200 μM, 40 μM, 8 μM, 1.6 μM, 0.32 μM, and 0.064 μM and then cultured for 48 hours; the 50 mM PBS, EtOH stock compound was treated to the cell culture at concentrations of 1 mM, 200 μM, 40 μM, 8 μM, 1.6 μM, 0.32 μM, and 0.064 μM and then cultured for 48 hours; and the 50 mM DMSO stock compound was treated to the cell culture at concentrations of 100 μM, 25 μM, 6.25 μM, 1.56 μM, 0.39 μM, 0.10 μM, and 0.02 μM and then cultured for 48 hours. To confirm the living cells after treatment with the compounds, MTT was added to each cell culture and incubated for additional 2 hours. The formazane crystals thus formed were dissolved using dimethyl sulfoxide (DMSO) and absorbance of the solution was measured at 560 nm. After culturing for 48 hours, the ratio of a cell count cultured on a well plate not treated with the compounds to a cell count on a well plate treated with the compounds synthesized in Examples was indicated as cell viability (%) according to each treated concentration. A cell viability curve was plotted using the cell viability (%) and the values of the concentration ($IC_{50}$) of the compounds, at which 50% of the growth was inhibited, were calculated to confirm their inhibitory effect against cancer cell proliferation.

The compounds synthesized by the methods described in Examples of the present invention were evaluated with respect to their oxygen consumption rates (OCR) and extracellular acidification rates (ECAR) according to the methods described in Test Example below.

Test Example 2: Measurement of Inhibitory Effect Against Oxygen Consumption Rate (OCR) and Extracellular Acidification Rate (ECAR)

Since biguanide-based drugs exhibit an anticancer effect by inhibiting oxidative phosphorylation, the cellular metabolic actions such as oxygen consumption rates (OCR), extracellular acidification rates (ECAR), etc., of the above compounds are measured.

A549 cell line (purchased from ATCC-American Type Culture Collection (ATCC)), a lung cancer cell line, is treated with the compounds and OCR and ECAR of the cells are measured and thereby those compounds which show an improved effect compared to phenformin are selected.

The cells are plated on an XF96 cell culture plate containing RPMI1640 medium at a concentration of $5\times10^3$ cells and cultured in 37° C., 5% $CO_2$ conditions to allow them to be attached thereto.

After 24 hours, the cells are treated with the drug at a concentration of 10 μM for 2 hours, the existing medium is washed with a medium for XF analysis (15 mM D-glucose, 15 mM sodium pyruvate, 4 mM L-glutamine, pH 7.4) to remove the medium using a Prep station and treated again with the drugs, and cultured in 37° C., non-$CO_2$ conditions in the Prep station for 1 hour. While culturing in the Prep station, a sensor cartridge is calibrated for 1 hour and added into a plate containing cells, and OCR and ECAR analyses are performed.

The measured values of OCR and ECAR of the compounds are calculated with reference to the measured values of OCR and ECAR of the control group which is set at 0% and the values of OCR and ECAR of phenformin, which was used as the reference drug, set at 100%, and those compounds which show an improved effect compared to those of phenformin are selected.

From the primarily-selected compounds, those compounds which show an improved effect are treated at various concentrations (0 μM, 0.5 μM, 1 μM, 5 μM, 10 μM, and 20 μM) and their reactivity according to concentration was obtained.

The results of inhibitory effects of the compounds against cancer cell proliferation are shown in Table 1 below.

TABLE 1

| Example | $IC_{50}$ (uM) @ HCT116 | AMPKa activation [pT172] (Unit/ml) @ MCF7 cell | | | | OCR (A549, 3 hrs) | ECAR (A549, 3 hrs) |
|---|---|---|---|---|---|---|---|
| | | 0 | 5 uM | 10 uM | 50 uM | 10 uM | 10 uM |
| 1 | ND | 5.3 | | | 4.6 | | |
| 2 | ND | 5.3 | | | 4.9 | | |
| 3 | ND | 5.3 | | | 6.2 | | |
| 4 | ND | 5.3 | | | 3.8 | | |
| 5 | ND | 5.3 | | | 5.8 | | |
| 6 | ND | 5.3 | | | 4.8 | 16.7% | 9.3% |
| 7 | >100 | 5.3 | 16.2 | 22.3 | 34.6 | | |
| 8 | >100 | 4.4 | 10.8 | 12.5 | 19.3 | | |
| 9 | ND | 5.3 | | | 16.3 | | |
| 10 | >100 | 6.8 | | | 10.4 | | |
| 11 | 4.8 | 4.6 | | | cell death (8 h treatment) | | |
| 12 | >100 | 6.8 | | | 3.1 | | |
| 13 | >100 | 6.8 | | | 7.0 | −20.0% | 61.0% |
| 14 | >100 | 6.8 | | | 11.0 | −7.0% | 63.0% |
| 15 | >100 | 6.8 | | | 6.1 | | |
| 16 | 45.9 | 3.3 | 7.0 | 9.4 | 13.6 | | |
| 17 | 35.1 | 6.1 | 10.2 | 10.8 | 55.7 | | |
| 18 | >100 | 3.9 | 7.1 | 8.6 | 13.3 | | |
| 19 | 41.7 | 3.9 | 3.3 | 4.3 | 15.3 | | |
| 20 | >100 | 3.9 | 2.9 | 4.5 | 5.6 | | |
| 21 | 43.2 | 3.9 | 6.0 | 5.8 | 14.8 | | |
| 22 | 35.2 | 3.9 | 3.8 | 10.1 | 22.3 | | |
| 23 | 12.7 | 3.9 | 7.7 | 6.6 | cell death | | |
| 24 | 11.5 | 3.9 | 5.2 | 4.7 | cell death | | |
| 25 | 8.4 | 3.9 | 5.8 | 7.0 | cell death | | |

TABLE 1-continued

| Example | IC$_{50}$ (uM) @ HCT116 | AMPKa activation [pT172] (Unit/ml) @ MCF7 cell | | | | OCR (A549, 3 hrs) 10 uM | ECAR (A549, 3 hrs) 10 uM |
| --- | --- | --- | --- | --- | --- | --- | --- |
| | | 0 | 5 uM | 10 uM | 50 uM | | |
| 26 | 9.7 | 3.9 | 3.6 | 6.6 | cell death | | |
| 27 | >100 | 6.5 | 9.8 | 8.7 | 14.3 | | |
| 28 | >100 | 6.5 | 7.7 | 9.2 | 7.9 | | |
| 29 | >100 | 3.7 | 4.0 | 5.4 | 6.8 | | |
| 30 | >100 | 3.7 | 4.2 | 4.0 | 4.2 | | |
| 31 | >100 | 3.7 | 2.5 | 3.6 | 6.1 | | |
| 32 | >100 | 3.7 | 5.5 | 5.2 | 5.3 | | |
| 33 | >100 | 3.7 | 3.8 | 3.3 | 4.3 | | |
| 34 | >100 | 3.7 | 4.5 | 3.7 | 7.0 | | |
| 35 | >100 | 3.7 | 5.0 | 4.2 | 3.4 | | |
| 36 | >100 | 5.5 | 5.5 | 5.8 | 4.8 | | |
| 37 | 32.8 | 5.5 | 5.8 | 7.5 | 15.0 | | |
| 38 | >100 | 5.5 | 5.9 | 5.1 | 6.4 | | |
| 39 | >100 | 6.0 | 6.2 | 7.1 | 8.2 | | |
| 40 | >100 | 6.0 | 7.0 | 5.1 | 7.2 | | |
| 41 | >100 | 6.0 | 8.3 | 10.2 | 14.4 | | |
| 42 | 23.7 | 4.4 | 4.3 | 8.7 | 19.1 | | |
| 43 | 100 | 4.4 | 3.0 | 4.3 | 7.6 | | |
| 44 | >100 | 4.2 | 4.5 | 5.2 | 14.8 | | |
| 45 | >100 | 3.8 | 3.0 | 4.0 | 3.5 | | |
| 46 | >100 | 3.8 | 3.8 | 3.6 | 5.4 | | |
| 47 | 130.1 | 3.8 | 2.8 | 3.8 | 5.3 | | |
| 48 | 8.6 | 3.8 | 4.3 | 6.8 | cell death | | |
| 49 | 5.1 | 3.8 | 9.3 | 13.7 | cell death | | |
| 50 | 6.7 | 3.8 | 8.3 | 11.5 | cell death | | |
| 51 | 6.6 | 3.8 | 12.5 | 15.2 | cell death | | |
| 52 | 6.8 | 3.8 | 9.4 | 15.0 | cell death | | |
| 53 | 6.1 | 3.8 | 9.2 | 13.9 | cell death | | |
| 54 | 6.7 | 3.8 | 4.9 | 8.9 | cell death | | |
| 55 | 10.4 | 3.8 | 3.5 | 5.3 | cell death | | |
| 56 | 48.8 | 2.6 | 2.7 | 4.8 | 15.4 | | |
| 57 | 2.5 | 2.6 | 6.7 | 12.1 | cell death | | |
| 58 | 2.3 | 2.6 | 2.5 | 5.0 | cell death | | |
| 59 | 2.3 | 2.6 | 9.8 | 13.3 | cell death | | |
| 60 | 15.4 | 2.7 | 4.6 | 7.8 | 20.9 | | |
| 61 | 12.6 | 2.7 | 6.4 | 11.8 | 12.3 | | |
| 62 | 2.8 | 2.7 | 8.5 | 26.6 | cell death | | |
| 63 | 2.8 | 2.7 | 15.1 | 22.9 | cell death | | |
| 64 | 36.1 | 2.7 | 2.2 | 4.4 | 31.4 | | |
| 65 | 2.5 | 2.7 | 15.0 | 20.1 | cell death | | |
| 66 | >100 | 4.5 | 3.3 | 3.7 | 4.1 | | |
| 67 | 147.2 | 4.5 | 3.2 | 2.9 | 4.8 | | |
| 68 | >100 | 4.5 | 4.2 | 4.4 | 4.4 | | |
| 69 | >100 | 3.3 | 5.6 | 4.7 | 5.3 | | |
| 70 | >100 | 4.1 | 3.5 | 4.0 | 5.4 | | |
| 71 | >100 | 3.7 | 3.8 | 4.3 | 5.8 | | |
| 72 | 37.7 | 4.1 | 5.4 | 6.6 | 19.1 | | |
| 73 | >100 | 3.7 | 3.9 | 4.5 | 9.1 | | |
| 74 | 48.3 | 3.7 | 4.9 | 5.3 | 8.3 | | |
| 75 | >100 | 3.7 | 3.5 | 3.6 | 5.3 | | |
| 76 | 42.1 | 3.2 | 4.5 | 4.7 | 8.8 | | |
| 77 | 50.6 | 3.7 | 4.5 | 5.7 | 13.9 | | |
| 78 | 58.3 | 3.6 | 3.4 | 3.4 | 3.8 | | |
| 79 | 7.9 | 4.1 | 7.8 | 11.7 | cell death | | |
| 80 | | | | | | 3% | 1% |
| 81 | | | | | | | |
| 82 | | | | | | 7.7% | 6.9% |
| 83 | | | | | | | |
| 84 | | | | | | | |
| 85 | | | | | | −6% | 31% |
| 86 | | | | | | | |
| 87 | | | | | | | |
| 88 | | | | | | | |
| 89 | | | | | | | |
| 90 | | | | | | | |
| 91 | | | | | | | |
| 92 | ND | 5.3 | | | 21.1 | | |
| 93 | ND | 5.3 | | | 6.6 | | |
| 94 | 104.7 | 6.8 | | | 9.0 | | |
| 95 | 14.1 | 8.5 | 4.9 | 6.8 | 23.6 | | |
| 96 | 8.2 | | | | | | |
| 97 | 7.5 | | | | | | |
| 98 | 49.2 | 6.1 | 7.2 | 9.6 | 37.5 | | |
| 99 | >100 | 5.8 | 4.0 | 2.9 | 3.6 | | |

TABLE 1-continued

| Example | IC$_{50}$ (uM) @ HCT116 | AMPKa activation [pT172] (Unit/ml) @ MCF7 cell | | | | OCR (A549, 3 hrs) 10 uM | ECAR (A549, 3 hrs) 10 uM |
|---|---|---|---|---|---|---|---|
| | | 0 | 5 uM | 10 uM | 50 uM | | |
| 100 | >100 | 6.5 | 7.1 | 9.0 | 8.0 | | |
| 101 | >100 | 3.7 | 4.1 | 3.6 | 5.9 | | |
| 102 | >100 | 4.3 | 4.8 | 2.8 | 6.8 | | |
| 103 | | | | | | 36.0% | −43.0% |
| 104 | | | | | | 31.3% | −8.3% |
| 105 | | | | | | 25.1% | −25.5% |
| 106 | | | | | | −6.6% | −7.5% |
| 107 | | | | | | −4.4% | −8.9% |
| 108 | ND | 5.3 | | | 3.9 | | |
| 109 | 42.5 | 6.6 | 8.2 | 9.9 | 10.3 | | |
| 110 | 97.2 | 5.3 | | | 3.9 | | |
| 111 | 35.7 | 8.2 | 11.4 | 12.1 | 30.2 | | |
| 112 | >100 | 6.8 | | | 10.6 | | |
| 113 | 72.7 | 8.2 | 9.9 | 10.1 | 28.6 | −3.0% | −24.0% |
| 114 | 117.7 | 6.8 | | | 6.1 | | |
| 115 | >100 | 6.1 | | | 4.8 | | |
| 116 | 101.4 | 6.8 | | | 25.9 | 0.0% | −24.0% |
| 117 | >100 | 6.1 | | | 6.2 | | |
| 118 | >100 | 6.1 | | | 6.0 | | |
| 119 | 3.5 | 6.6 | 6.9 | 8.8 | 8.5 | | |
| 120 | >100 | 6.8 | | | 8.1 | | |
| 121 | >100 | 4.4 | | | 9.0 | | |
| 122 | >100 | 6.1 | | | 5.9 | 13.3% | 15.5% |
| 123 | >100 | 7.1 | 6.6 | 7.5 | 12.6 | | |
| 124 | 56.7 | 4.4 | | | 8.4 | | |
| 125 | >100 | 4.4 | | | 5.0 | | |
| 126 | >100 | 4.4 | 6.1 | 6.4 | 10.7 | | |
| 127 | >100 | 4.4 | | | 5.8 | 10.2% | 7% |
| 128 | >100 | 6.6 | 7.6 | 7.1 | 8.8 | | |
| 129 | >100 | 6.6 | 9.2 | 7.0 | 11.4 | | |
| 130 | >100 | 4.4 | | | 8.8 | | |
| 131 | >100 | 4.4 | | | 17.6 | | |
| 132 | >100 | 6.6 | 6.1 | 6..5 | 8.1 | 39.3% | 44.7% |
| 133 | >100 | 4.4 | | | 7.1 | | |
| 134 | >100 | 4.4 | | | 16.2 | | |
| 135 | >100 | 4.4 | | | 4.2 | | |
| 136 | >100 | 4.4 | | | 5.9 | | |
| 137 | >100 | 3.3 | 4.1 | 7.3 | 11.9 | | |
| 138 | >100 | 3.3 | 3.7 | 3.7 | 4.2 | | |
| 139 | >100 | 7.1 | 5.7 | 5.8 | 10.9 | | |
| 140 | 100.0 | 6.6 | 6.2 | 6.6 | 8.7 | | |
| 141 | >100 | 6.6 | 5.6 | 6.1 | 10.3 | | |
| 142 | 73.6 | 6.6 | 4.7 | 6.0 | 7.2 | | |
| 143 | 123.7 | 5.5 | 5.5 | 5.7 | 7.2 | | |
| 144 | | | | | | 47% | 7% |
| 145 | | | | | | | |
| 146 | | | | | | 109% | 28% |
| 147 | | | | | | 74% | 126% |
| 148 | | | | | | 1% | 160% |
| 149 | | | | | | 20% | 36% |
| 150 | | | | | | 105% | 125% |
| 151 | | 6.4 | 9.4 | 7.7 | 11.2 | | |
| 152 | | 6.4 | 7.9 | 8.1 | 8.6 | | |
| 153 | | 6.4 | 8.0 | 6.8 | 6.3 | | |
| 154 | >100 | 2.0 | 2.9 | 2.9 | 2.8 | | |
| 155 | >100 | 2.0 | 3.3 | 2.8 | 3.9 | | |
| 156 | >100 | 2.0 | 3.6 | 2.6 | 4.9 | | |
| 157 | | 2.39 | 4.17 | 2.68 | 2.00 | | |
| 158 | | 2.39 | 3.11 | 2.49 | 3.75 | | |
| 159 | | 2.35 | 2.17 | 2.35 | 3.02 | | |
| 160 | | 2.35 | 2.51 | 2.65 | 2.84 | | |
| 161 | | 2.35 | 3.03 | 2.73 | 4.06 | | |
| 162 | | 3.21 | 4.41 | 4.04 | 7.34 | | |
| 163 | | 3.21 | 4.07 | 3.76 | 4.48 | | |
| 164 | | 3.21 | 2.89 | 3.43 | 2.77 | −1% | 9% |
| 165 | | 3.21 | 3.80 | 4.36 | 9.16 | | |

The invention claimed is:
1. A compound selected from the group consisting of the following compounds:
2) N1-piperidin-N5-piperidine biguanide,
8) N1,N1-dipropyl-N5-piperidine biguanide,
9) N1-piperidin-N5-(benzo[d][1,3]dioxol-5-yl)methyl biguanide,
12) N1-piperidin-N5-(2-chloro)benzyl biguanide,
13) N1-piperidin-N5-(4-chloro)phenethyl biguanide,
14) N1-piperidin-N5-(2-chloro)phenethyl biguanide,
23) N1-(4-ethoxy)piperidin-N5-(4-trifluoromethyl)phenyl biguanide,
24) N1-(4-ethoxy)piperidin-N5-(3-trifluoromethyl)phenyl biguanide,
25) N1-(4-ethoxy)piperidin-N5-(3-trifluoromethoxy)phenyl biguanide,
26) N1-(4-ethoxy)piperidin-N5-(4-trifluoromethoxy)phenyl biguanide,
41) N1-(3-pyridine)-N5-(3-trifluoromethyl)phenyl biguanide,
42) N1-3-pyridin-N5-(3-trifluoromethoxy)benzyl biguanide,
43) N1-3-pyridin-N5-(3-trifluoromethyl)benzyl biguanide,
44) N1-(3-methyl)piperidin-N5-cyclopentyl biguanide,
45) N1-(3-methyl)piperidin-N5-(4-methoxy)piperidine biguanide,
46) N1-(3-methyl)piperidin-N5-(4-ethoxy)piperidine biguanide,
47) N1-(3-methyl)piperidin-N5-pyrazin-2yl biguanide,
48) N1-(4-methyl)piperidin-N5-(4-bromo)phenyl biguanide hydrochloride,
49) N1-(4-methyl)piperidin-N5-(3-trifluoromethoxy)phenyl biguanide,
50) N1-(4-methyl)piperidin-N5-(3-trifluoromethyl)phenyl biguanide,
52) N1-(4-methyl)piperidin-N5-(4-trifluoromethoxy)phenyl biguanide,
53) N1-(4-methyl)piperidin-N5-(4-trifluoromethyl)phenyl biguanide,
54) N1-(4-methyl)piperidin-N5-(3-trifluoromethyl)-4-fluoro)phenyl biguanide,
56) N1-(4-methyl)piperidin-N5-(4-fluoro)phenyl biguanide,
57) N1-(4-methyl)piperidin-N5-(3-fluoro-4-trifluoromethyl)phenyl biguanide,
58) N1-(4-methyl)piperidin-N5-(3-trifluoromethyl-4-chloro)phenyl biguanide,
59) N1-(4-methyl)piperidin-N5-(3-fluoro-4-trifluoromethyl)phenyl biguanide,
60) N1-(4-methyl)piperidin-N5-(3-trifluoromethyl)benzyl biguanide,
61) N1-(4-methyl)piperidin-N5-(4-trifluoromethyl)benzyl biguanide,
62) N1-(3,5-dimethyl)piperidin-N5 (4-trifluoromethoxy)phenyl biguanide,
63) N1-(3,5-dimethyl)piperidin-N5-(4-trifluoromethyl)phenyl biguanide,
64) N1-(3,5-dimethyl)piperidin-N5-(4-fluoro)phenyl biguanide,
65) N1-(3,5-dimethyl)piperidin-N5-(3-trifluoromethyl-4-fluoro)phenyl biguanide,
66) N1-2,5-dihydro-1H-pyrrol-N5-pyridin-3-yl biguanide,
67) N1-2,5-dihydro-1H-pyrrol-N5-2,5-dihydro-1H-pyrrole biguanide,
68) N1-1,2,3,6-tetrahydropyridin-N5-1,2,3,6-tetrahydropyridine biguanide,
69) N1-(4-methyl)piperidin-N5-(4-aminoethyl)phenyl biguanide,
70) N1-pyrrolidin-N5-(4-acetyl)phenyl biguanide,
71) N1-piperidin-N5-(4-morpholin-4-yl)phenyl biguanide,
72) N1-pyrrolidin-N5-(4-bromo)phenyl biguanide,
74) N1-piperidin-N5-(2-propyl)phenyl biguanide,
75) N1-pyrrolidin-N5-(2-trifluoromethyl)phenyl biguanide,
76) N1-pyrrolidin-N5-(2-chloro-5-trifluoromethyl)phenyl biguanide,
77) N1-pyrrolidin-N5-(2-chloro-4-fluoro)phenyl biguanide,
78) N1-pyrrolidin-N5-(2,3-dichloro)phenyl biguanide,
79) N1-pyrrolidin-N5-(4-trifluoromethylthio)phenyl biguanide,
80) N1-pyrrolidin-N5-(2,6-difluoro)phenyl biguanide,
81) (3-(3-(imino(piperidin-1-yl)methyl)guanidino)benzyl)triphenylphosphonium chloride,
82) N1-pyrrolidin-N5-methyl-N5-(4-trifluoromethoxy) phenyl biguanide,
83) N1-pyrrolidin-N5-(4-phenoxy)phenyl biguanide,
90) N1-(4,4-difluoro)piperidin-N5-(3,4-dichloro)phenyl biguanide,
91) N1-(4,4-difluoro)piperidin-N5-5,6,7,8-tetrahydronaphthalen-2-yl,
99) N1-piperidin-N2-(2-thiophen-2-yl)ethyl biguanide,
105) N1-(4-trifluoromethoxy)phenyl-N2-methyl-N5-pyrrolidine biguanide,
106) N1-methyl-N1-(4-trifluoromethoxy)phenyl-N2-methyl-N5-pyrrolidine biguanide,
127) N1-4-(pyridin-2-yl)piperazine biguanide,
151) N-(6,6-dimethyl-4-oxo-1,4,5,6-tetrahydropyrimidin-2-yl)piperid in-1-carboximidamide,
153) N-(1,4,5,6-tetrahydropyrimidin-2-yl)piperidin-1-carboximidamide,
154) N-(6-methyl-4-oxo-1,4,5,6-tetrahydropyrimidin-2-yl)piperidin-1-carboximidamide,
155) N-(5-methyl-4-oxo-1,4,5,6-tetrahydropyrimidin-2-yl)piperidin-1-carboximidamide,
156) N-(4-oxo-1,4,5,6-tetrahydropyrimidin-2-yl)piperidin-1-carboximidamide,
157) N-(6-cyclopropyl-4-oxo-1,4,5,6-tetrahydropyrimidin-2-yl)piperidin-1-carboximidamide hydrochloride,
158) N-(5-methyl-1,4,5,6-tetrahydropyrimidin-2-yl)piperidin-1-carboximidamide,
159) N-(6-isopropyl-4-oxo-1,4,5,6-tetrahydropyrimidin-2-yl)piperidin-1-carboximidamide,
161) N-(6-isobutyl-4-oxo-1,4,5,6-tetrahydropyrimidin-2-yl)piperidin-1-carboximidamide,
162) N-(4-methyl-1,4,5,6-tetrahydropyrimidin-2-yl)piperidin-1-carboximidamide,
163) N-(6-propyl-4-oxo-1,4,5,6-tetrahydropyrimidin-2-yl)piperidin-1-carboximidamide, and
165) N-(4-ethyl-1,4,5,6-tetrahydropyrimidin-2-yl)piperidin-1-carboximidamide;
or a pharmaceutically acceptable salt thereof.
2. The compound of claim 1 or a pharmaceutically acceptable salt thereof wherein the pharmaceutically acceptable salt is a salt with an acid selected from the group consisting of formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, benzenesulfonic acid, p-toluenesulfonic acid, methanesulfonic acid, dichloroacetic acid, aminooxy acetic acid, hydrochloric acid, hydrobromic acid, sulfuric acid, phosphoric acid, nitric acid, carbonic acid, and boric acid.

3. A composition comprising the compound of claim 1 or a pharmaceutically acceptable salt of the compound of claim 1, and a carrier.

4. The composition of claim 3, wherein the the carrier is a pharmaceutically acceptable carrier.

5. A method for or treating colorectal cancer or lung cancer comprising administering a therapeutically effective amount of the compound of claim 1 or a pharmaceutically acceptable salt thereof to a subject in need thereof.

* * * * *

UNITED STATES PATENT AND TRADEMARK OFFICE
CERTIFICATE OF CORRECTION

PATENT NO. : 11,572,341 B2
APPLICATION NO. : 16/820860
DATED : February 7, 2023
INVENTOR(S) : Hong Woo Kim et al.

It is certified that error appears in the above-identified patent and that said Letters Patent is hereby corrected as shown below:

In the Claims

Column 74, Lines 27-28, Claim 1, replace "91) N1-(4,4-difluoro)piperidin-N5-5,6,7,8-tetrahydronaphthalen-2-yl," with --91) N1-(4,4-difluoro)piperidin-N5-5,6,7,8-tetrahydronaphthalen-2-yl biguanide,--;
Line 35-36, replace "tetrahydropyrimidin-2-yl)piperid in-1-carboximidamide," with --tetrahydropyrimidin-2-yl)piperidin-1-carboximidamide,--.

Column 75, Line 11, Claim 5, replace "5. A method for or treating colorectal cancer or lung" with --5. A method for treating colorectal cancer or lung--.

Signed and Sealed this
Twenty-eighth Day of March, 2023

Katherine Kelly Vidal
*Director of the United States Patent and Trademark Office*